US012178862B2

(12) United States Patent
Binder

(10) Patent No.: US 12,178,862 B2
(45) Date of Patent: Dec. 31, 2024

(54) ZONAL AND TARGETED METHODS AND USES FOR TREATING A MIGRAINE DISORDER

(71) Applicant: Miotox, LLC, Beverly Hills, CA (US)

(72) Inventor: William J. Binder, Beverly Hills, CA (US)

(73) Assignee: Miotox, LLC, Beverly Hills, CA (US)

( * ) Notice: Subject to any disclaimer, the term of this patent is extended or adjusted under 35 U.S.C. 154(b) by 0 days.

(21) Appl. No.: 17/338,388

(22) Filed: Jun. 3, 2021

(65) Prior Publication Data

US 2021/0379166 A1    Dec. 9, 2021

Related U.S. Application Data

(60) Provisional application No. 63/034,215, filed on Jun. 3, 2020.

(51) Int. Cl.
*A61K 38/48*    (2006.01)
*A61K 9/00*    (2006.01)
*A61P 25/06*    (2006.01)

(52) U.S. Cl.
CPC ........ *A61K 38/4893* (2013.01); *A61K 9/0019* (2013.01); *A61P 25/06* (2018.01)

(58) Field of Classification Search
CPC .... A61K 38/4893; A61K 9/0019; A61P 25/06
See application file for complete search history.

(56) References Cited

U.S. PATENT DOCUMENTS

| 5,714,468 A | 2/1998 | Binder |
| 7,655,244 B2 | 2/2010 | Blumenfeld |

(Continued)

FOREIGN PATENT DOCUMENTS

| CA | 2596366 A1 | 8/2006 |
| WO | 2004084839 A2 | 10/2004 |

(Continued)

OTHER PUBLICATIONS

Choi, II, and Sang Ryong Jeon. "Neuralgias of the head: occipital neuralgia." Journal of Korean Medical Science 31.4 (2016): 479-488. (Year: 2016).*

(Continued)

*Primary Examiner* — Louise W Humphrey
*Assistant Examiner* — Candice Lee Swift
(74) *Attorney, Agent, or Firm* — UltimatEdge IP Law Group, P.C.; Dean G. Stathakis

(57) ABSTRACT

The present specification discloses methods and uses for treating a migraine disorder. The disclosed method comprising extramuscularly administering a Botulinum toxin to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual. The disclosed methods and uses further comprise extramuscularly administering a Botulinum toxin to one or more nerve exit points and/or one or more subcutaneous locations in the head and neck as well as one or more sites of an epicranial aponeurosis. The disclosed methods and uses further comprise intramuscularly administering a Botulinum toxin to one or more locations within the left and right Splenius Capitus muscle, the left and right Masseter muscles, the left and right Trapezius muscles, or any combination thereof.

35 Claims, 5 Drawing Sheets

(56) References Cited

U.S. PATENT DOCUMENTS

| | | | |
|---|---|---|---|
| 7,704,511 | B2 | 4/2010 | Turkel et al. |
| 7,749,515 | B2 | 7/2010 | Blumenfeld |
| 8,420,106 | B1 | 4/2013 | Binder |
| 8,491,917 | B1 | 7/2013 | Bender |
| 8,617,569 | B2 | 12/2013 | Binder |
| 8,722,060 | B2 | 5/2014 | Binder |
| 8,883,143 | B2 | 11/2014 | Binder |
| 10,111,938 | B2 | 10/2018 | Blumenfeld et al. |
| 10,201,497 | B2 | 2/2019 | Binder |
| 10,406,213 | B2 | 9/2019 | Turkel et al. |
| 2005/0147626 | A1 | 7/2005 | Blumenfeld |
| 2005/0191320 | A1 | 9/2005 | Turkel et al. |
| 2008/0069841 | A1 | 3/2008 | Panjwani et al. |
| 2008/0279895 | A1 | 11/2008 | Blumenfeld |
| 2009/0252764 | A1 | 10/2009 | Blumenfeld |
| 2009/0263426 | A1 | 10/2009 | Turkel et al. |
| 2010/0189655 | A1 | 7/2010 | Turkel et al. |
| 2011/0200639 | A1 | 8/2011 | Blumenfeld |
| 2017/0088612 | A1 | 3/2017 | Bigal |
| 2019/0060423 | A1 | 2/2019 | Blumenfeld et al. |
| 2019/0240299 | A1 | 8/2019 | Blumenfeld |
| 2019/0256607 | A1 | 8/2019 | Sun et al. |
| 2020/0000892 | A1 | 1/2020 | Turkel et al. |

FOREIGN PATENT DOCUMENTS

| | | |
|---|---|---|
| WO | 2005084705 A1 | 9/2005 |
| WO | 2006083455 A1 | 8/2006 |
| WO | 2010135538 A1 | 11/2010 |
| WO | 2013137969 A1 | 9/2013 |
| WO | 2018175696 A1 | 9/2018 |

OTHER PUBLICATIONS

Biologydictionary.net Editors. "Zygomatic Arch." Biology Dictionary, Biologydictionary.net, Apr. 5, 2017, https://biologydictionary.net/zygomatic-arch/. (Year: 2017).*

Advanced Anatomy 2nd Ed; https://pressbooks.bccampus.ca/advancedanatomy1sted/chapter/muscles/#:~:text=Epicranial%20Aponeurosis%20also%20referred%20to,bones%20to%20the%20lambdoid%20suture; Accessed Dec. 22, 2022 (Year: 2018).*

Biologydictionary.net Editors. "Occipital Bone." Biology Dictionary, Biologydictionary.net, Jun. 11, 2020, https://biologydictionary.net/occipital-bone/. (Year: 2020).*

Breeland G, Aktar A, Patel BC. Anatomy, Head and Neck, Mandible. [Updated Jun. 11, 2022]. In: StatPearls [Internet]. Treasure Island (FL): StatPearls Publishing; Jan. 2022—Available from: https://www.ncbi.nlm.nih.gov/books/NBK532292/ (Year: 2022).*

Yu M, Wang SM. Anatomy, Head and Neck, Occipital Nerves. [Updated Oct. 31, 2022]. In: StatPearls [Internet]. Treasure Island (FL): StatPearls Publishing; Jan. 2022—Available from: https://www.ncbi.nlm.nih.gov/books/NBK542213/ (Year: 2022).*

Glenesk NL, Kortz MW, Lopez PP. Anatomy, Head and Neck, Posterior Cervical Nerve Plexus. [Updated Jul. 25, 2022]. In: StatPearls [Internet]. Treasure Island (FL): StatPearls Publishing; Jan. 2022—Available from: https://www.ncbi.nlm.nih.gov/books/NBK538514/ (Year: 2022).*

Brown TM, Drake TM, Krishnamurthy K. Anatomy, Head and Neck, Procerus Muscle. [Updated Aug. 8, 2022]. In: StatPearls [Internet ]. Treasure Island (FL): StatPearls Publishing; Jan. 2022—Available from: https://www.ncbi.nlm.nih.gov/books/NBK534763/ (Year: 2022).*

Zito PM, Chauhan PR. Anatomy, Head and Neck, Supratrochlear. [Updated Jul. 25, 2022]. In: StatPearls [Internet]. Treasure Island (FL): StatPearls Publishing; Jan. 2022—Available from: https://www.ncbi.nlm.nih.gov/books/NBK557549/ (Year: 2022).*

Bordoni B, Varacallo M. Anatomy, Head and Neck, Sternocleidomastoideole. [Updated Apr. 5, 2022]. In: StatPearls [Internet]. Treasure Island (FL): StatPearls Publishing; Jan. 2022—Available from: https://www.ncbi.nlm.nih.gov/books/NBK532881/ (Year: 2022).*

Gatt A, Agarwal S, Zito PM. Anatomy, Fascia Layers. Jul. 25, 2022. In: StatPearls [Internet]. Treasure Island (FL): StatPearls Publishing; Jan. 2023—PMID: 30252294. (Year: 2022).*

Tajran J, Gosman AA. Anatomy, Head and Neck, Scalp. [Updated Jul. 25, 2022]. In: StatPearls [Internet]. Treasure Island (FL): StatPearls Publishing; Jan. 2023—Available from: https://www.ncbi.nlm.nih.gov/books/NBK551565/ (Year: 2023).*

Kaye, Rachel, William J. Binder, and Andrew Blitzer. "Botox for migraine headaches and facial pain." Diagnosis and Management of Head and Face Pain: A Practical Approach (2018): 171-186. (Year: 2018).*

Luvisetto, Siro, et al. "Botulinum toxin type a as a therapeutic agent against headache and related disorders." Toxins 7.9 (2015):3818-3844. (Year: 2015).*

Albanese, Terminology for Preparations of Botulinum Neurotoxins: What a Difference Makes, JAMA 305:89-90 (2011).

Allergan, Botox Product Information (url: https://hcp.botoxcosmetic.com/) (Downloaded 2016).

Allergan, Injection Workbook for Chronic Migraine (2015).

Anonymous, PTSD—Does anyone else deal with chronic daily headache from PTSD, how do you treat them? URL: https://www.drugs.com/answers/post-traumatic-stress-disorder-does-anyone-else-408139.html (Downloaded Dec. 1, 2016).

Bach-Rojecky, et al., Central origin of the antinociceptive action of botulinum toxin type A, Pharmacology, Biochemistry and Behavior 94: 234-238 (2009).

Bahl, et al., Local Anethesia in Dentistry, Anesth Prog 51:138-142 (2004).

Binder, et al., Botulinum toxin type A (Botox) for treatment of migraine headaches: An open-label study, Otolaryngology—Head and Neck Surgery 123: 669-676 (2000).

Binder, et al., Treatment of migraine headache with botulinum toxin type A, Facial Plastic Surgery Clinics of North America 11: 465-475 (2003).

Blumenfeld, et al., Insights into the Functional Anatomy Behind the Preempt Injection Paradigm: Guidance on Achieving Optimal Outcomes, Headache 57:766-777 (2017).

Blumenfeld, et al., Method of Injection of OnabotulinumtoxinA for Chronic Migraine: A Safe, Well-Tolerated, and Effective Treatment Paradigm Based on the Preempt Clinical Program, Headache 50: 1406-1418 (2010).

Blumenfeld, et al., Procedures for Administering Botulinum Toxin Type A for Migraine and Tension-type Headache, Headache 43:884-891 (2003).

Blumenfeld, et al., The Emerging Role of Botulinum Toxin A in Headache Prevention, Operative Techniques in Otolaryngology—Head and Neck Surgery 15(2):90-96 (2004).

Channell, et al., Management of Chronic Posttraumatic Headache: A Multidisciplinary Approach, JAOA 109: 509-513 (2009).

Day, Sphenopalantine Ganglion Analgesia, Curr Rev Pain. 3:342-347 (1999).

EPO, Extended Search Report for European Patent Application Serial No. EP13760304.9 pp. 7 (Mar. 13, 2015).

Gerwin, Treatment of Chronic Migraine Headache with OnabotulinumtoxinA, Curr Rev Pain. 15: 336-338 (2011).

Goadsby, Sphenopalatine (pterygopalatine) ganglion stimulation and cluster headache: New hope for ye who enter here, Cephalagia 33: 813-815 (2013).

Malamed, et al., Intraoral Maxillary Nerve Block: an anatomical and clinical study, Anesthesia Progress, 30: 44-48 (1983).

Niamtu, Local Anesthetic Blocks of the Head and Neck for Cosmetic Facial Surgery, III: Techniques for the Maxillary Nerve, Cosmetic Dermatology 17:645-647 (2004).

Peterlin, et al., Post-Traumatic Stress Disorder in Migraine, Headache 49:541-551 (2009).

Peterlin, et al., Post-Traumatic Stress Disorder in Episodic and Chronic Migraine, Headache 48:517-522 (2008).

Robertson, et al., Critical analysis of the use of OnabotulinumtoxinA (botulinum toxin type A) in migraine, Neuropsychiatric Disease and Treatment 8:35-48 (2012).

Shone, et al., Peptide substrate specificty and properties of the zinc-endopeptidase activity of botulinum type B neurotoxin, Eur. J. Biochem 225: 263-270 (1994).

(56) References Cited

OTHER PUBLICATIONS

WIPO, PCT Form IB373, International Preliminary Report on Patentability for International Patent Application Serial No. PCT/US2013/000131, pp. 7 (Sep. 16, 2014).

WIPO, PCT Form ISA210, International Search Report for International Patent Application Serial No. PCT/US2013/000131, pp. 2 (Aug. 6, 2013).

WIPO, PCT Form ISA210, International Search Report for International Patent Application Serial No. PCT/US2021/035736, pp. 3 (Sep. 27, 2021).

WIPO, PCT Form ISA237, Written Opinion for International Patent Application Serial No. PCT/US2013/000131, pp. 5 (Aug. 6, 2013).

WIPO, PCT Form ISA237, Written Opinion for International Patent Application Serial No. PCT/US2021/035736, pp. 5 (Sep. 27, 2021).

Arcilla, et al., Neuroanatomy, Unmyelinated Nerve Fibers, pp. 7, StatPearls, (2023).

Argyriou, et al., OnabotulinumtoxinA Add-On to Monoclonal Anti-CGRP Antibodies in Treatment-Refractory Chronic Migraine, Toxins 14(12): 847-857 (2022).

Barba, et al., Learning Curve of Botulinum Toxin Bladder Injection for the Treatment of Refractory Overactive Bladder, Int. J. Womens Health 14: 1-7 (2022).

Burstein, et al., Mechanism of Action of OnabotulinumtoxinA in Chronic Migraine: A Narrative Review, Headache, 60: 1259-1271 (2020).

Crawford, et al., Functional Anatomy of the Sensory Nervous System: Updates from the Neuroscience Bench, 48 (1): 174-189 (2020).

Ginsberg, et al., Great Auricular Nerve: Anatomy and Imaging in a Case of Perineural Tumor Spread, Am. J. Neuroradiol. 21: 568-571 (2000).

Glenesk, et al., Anatomy, Head and Neck, Posterior Cervical Nerve Plexus, StatPearls, pp. 4 (2023).

Greenberg, et al., Anatomy, Head and Neck: Auriculotemporal Nerve, StatPearls, pp. 4 (2023).

Grujicic, Occipital Nerves, pp. 4, KenHub at https://www.kenhub.com/en/library/anatomy/occipital-nerves (2023).

Huff, et al., Neuroanatomy, Cranial Nerve 5 (Trigeminal), StatPearls, pp. 7 (2022).

Iyengar, et al., CGRP and the Trigeminal System in Migraine, Headache 59: 659-681 (2019).

Ko, et al., Retrospective Observational Study of Treatment Patterns and Efficacy of onabotulinumtoxinA Therapy in Patients with Refractory Overactive Bladder in Clinical Practice, Toxins 15(5): 338-251 (2023).

Napier, et al., Supraorbital Nerve Block, StatPearls, pp. 7 (2023).

Nguyen, et al., Anatomy, Head and Neck: Face, StatPearls, pp. 10 (2023).

Patel, et al., Neuroanatomy, Spinal Trigeminal Nucleus, StatPearls, pp. 7 (2022).

Sendic, Greater Auricular Nerve, pp. 3, KenHub at https://www.kenhub.com/en/library/anatomy/greater-auricular-nerve (2023).

Shafique, et al., Anatomy, Head and Neck, Maxillary Nerve, StatPearls, pp. 7 (2023).

Stathakios, et al., Anatomy, Head and Neck, Posterior Cervical Region, StatPearls, pp. 7 (2023).

Stathakios, et al., Anatomy, Head and Neck, Neck Triangle, StatPearls, pp. 10 (2023).

Veerapaneni, et al., Trigeminal Neuropathy, StatPearls, pp. 15 (2023).

Yu, et al., Anatomy, Head and Neck, Zygomatic, StatPearls, pp. 5 (2023).

Yu, et al., Anatomy, Head and Neck, Occipital Nerves, StatPearls, pp. 10 (2023).

Zito, et al., Anatomy, Head and Neck, Supratrochlear, StatPearls, pp. 8 (2023).

Luvisetto, Botulinum Neurotoxins in Central Nervous System: An Overview from Animal Models to Human Therapy, Toxins 13: 751-767 (2021).

Melo-Carrillo, et al., Combined OnabotulinumtoxinA/Atogepant Treatment Blocks Activation/Sensitization of High-Threshold and Wide-Dynamic Range Neurons, Cephalagia, 41(1) 17-32 (2021).

Yam, et al., General Pathways of Pain Sensation and the Major Neurotransmitters Involved in Pain Regulation, Int. J. Mol. Sci. 19: 2164-2186 (2018).

* cited by examiner

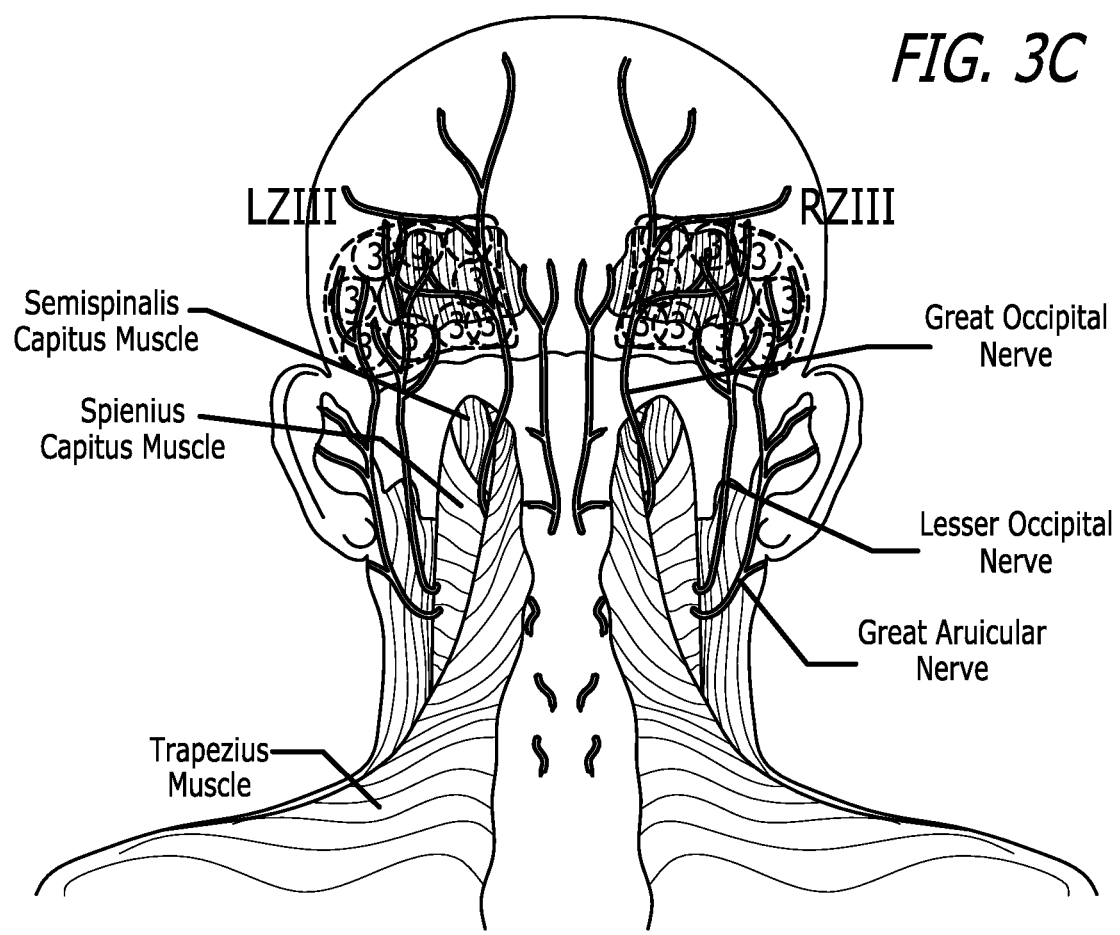

ZONAL AND TARGETED METHODS AND USES FOR TREATING A MIGRAINE DISORDER

This application claims the benefit of priority and is entitled to the filing date pursuant to 35 U.S.C. § 119(e) of U.S. Provisional Patent Application 63/034,215, filed Jun. 3, 2020, the content of which is hereby incorporated by reference in its entirety.

A migraine disorder is a neurological condition that can cause multiple symptoms. It is frequently characterized by intense, debilitating headaches made worse by movement. Symptoms may include nausea, vomiting, difficulty in speaking, numbness and tingling and sensitivity to light and sound. Chronic posttraumatic migraine headaches and persistent post-traumatic headache with migraine disorder features as defined by the International Headache classification (ICHD-3), has a similar high disability and is one of the most disabling medical conditions.

Persistent post-traumatic headache is often part of and contributory to post traumatic syndrome (PTS or PTSD) which can also include post-traumatic stress, anxiety, and depression. Reports indicate that nearly 40% of soldiers had migraines or probable migraines during their tours of duty, but few had a history of migraines before their deployments. In accordance with the present invention, a patient group can be identified by survey or investigation. For example, 19% of the 2,687 soldiers surveyed upon return from duty met the criteria for definite migraines, 18% had probable migraines, and 11% non-migraine-type headaches. Those with definite migraines had an average of 3.5 migraine days/month. Just 5% of the soldiers had a history of migraine headaches prior to their deployments to Iraq.

As an example, after returning home from Iraq, soldiers are sent through a medical processing site. Members of one brigade completed a validated 17-question survey about headaches. Based on their survey responses, soldiers were divided into three groups: definite migraines, probable migraines, or non-migraine headaches, a system of classification similar to that used in the American Migraine Study. The mean age of respondents was 27. The group was 95% male and 5% female. Soldiers rated their migraine headaches as a mean 6.5 on a 10-point severity scale, lasting an average of 5.2 hours. Yet only 2% received medications such as triptans, a recommended standard of care for the treatment of acute migraines.

The present specification discloses methods and uses to safely and effectively treat a migraine disorder using a Botulinum toxin A. The methods and uses employ higher Botulinum toxin dosing for the treatment of migraine, including chronic post-traumatic migraines attributed to a traumatic injury to the head or whiplash and symptoms of Post-Traumatic Stress Disorder (PTSD), that are commonly associated with the results of posttraumatic migraine.

SUMMARY

The present specification discloses methods and uses for treating a migraine disorder. The disclosed methods and uses comprising extramuscularly administering a Botulinum toxin to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual. The one or more areas of the fronto-fascial layer include a left frontal nerve cluster zone and a right frontal nerve cluster zone. The one of more areas of the temporoparietal-fascial layer include a left temporal nerve cluster zone and a right temporal nerve cluster zone. The one or more areas the occipito-fascial layer include a left occipital nerve cluster zone and a right occipital nerve cluster zone. The disclosed methods and uses comprise extramuscular administering about 20 units to about 30 units of a Botulinum toxin to one or more sites within each of the left and right frontal nerve cluster zones, about 20 units to about 35 units of the Botulinum toxin to one or more sites within each of the left and right temporal nerve cluster zones, and about 30 units to about 55 units of the Botulinum toxin to one or more sites within each of the left and right occipital nerve cluster zones, each of the one or more sites is administered 5 units of the Botulinum toxin. The concentration of the Botulinum toxin administered is from about 5 units/100 µL to about 5 units/200 µL. Examples of migraine disorders treated by the disclosed methods and uses include, without limitation, is a chronic migraine, an episodic migraine, a migraine associated with traumatic brain injury, a migraine associated with a post-traumatic head injury, a migraine associated with whiplash.

Aspects of the present specification also indicate that the disclosed methods and uses further comprise extramuscularly administering a Botulinum toxin to one or more nerve exit points in the head and neck including one or more nerve exit points of a Supraorbital nerve, a Supratrochlear nerve, a medial branch of a Supratrochlear Nerve, a Greater Auricular nerve, a Cervical Nerve Plexus, a Supraclavicular nerve, or any combination thereof. Each of the one or more nerve exit points is administered 5 units of the Botulinum toxin. The concentration of the Botulinum toxin administered is from about 5 units/100 µL to about 5 units/200 µL.

The disclosed methods and uses further comprise extramuscularly administering a Botulinum toxin to one or more sites of an epicranial aponeurosis. Each of the one or more sites is administered 5 units of the Botulinum toxin. The concentration of the Botulinum toxin administered is from about 5 units/100 µL to about 5 units/200 µL.

The disclosed methods and uses further optionally comprise intramuscularly administering a Botulinum toxin to one or more locations within the left and right Splenius Capitus muscle, the left and right Masseter muscles, the left and right Sternocleidomastoid and Trapezius muscles, or any combination thereof. Each of the one or more locations is administered 5 units of the Botulinum toxin. The concentration of the Botulinum toxin administered is from about 5 units/100 µL to about 5 units/200 µL.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIGS. 3A-C show an exemplary embodiment of occipital nerve cluster zones of the occipito-fascial layer from a method and use disclosed herein with FIG. 3A showing exemplary left and right occipital nerve cluster zones LZIII and RZIII, fixed and additional extramuscular administration sites as well as optional intramuscular administration sites, FIG. 3B showing exemplary administration sites of one embodiment located within left and right occipital nerve cluster zones LZIII and RZIII and FIG. 3C showing exemplary administration sites of another embodiment located within left and right occipital nerve cluster zones LZIII and RZIII;

DETAILED DESCRIPTION

Figure 1A:
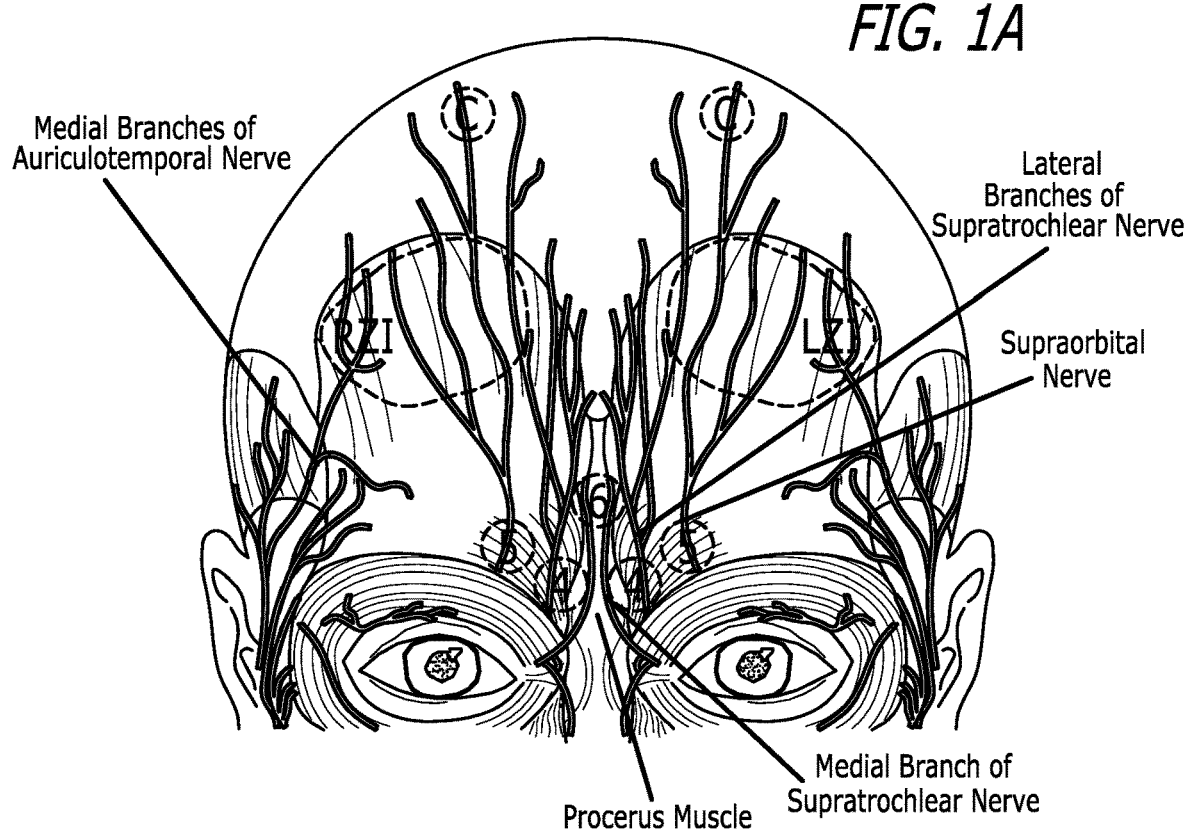
FIGS. 1A-B show an exemplary embodiment of frontal nerve cluster zones of the fronto-fascial layer from a method and use disclosed herein with FIG. 1A showing exemplary left and right frontal nerve cluster zones LZI and RZI as well as fixed and additional extramuscular administration sites located in the forehead, and FIG. 1B showing exemplary administration sites located within left and right frontal nerve cluster zones LZI and RZI.

Current methods employing a Botulinum toxin to treat migraines use a low total dose and low administration volume of the toxin. For example, in the current FDA-approved treatment for a migraine, 31 sites in the head and neck are intramuscularly administered with a Botulinum toxin, with each site being administered 5 units/100 µL of the Botulinum toxin for a total of 155 units. Table 1 below shows the seven muscle locations and doses administered.

signal and other symptoms associated with migraine innervate a larger area of the head and neck. As such, another disadvantage associated with the current approved protocol is that it simply does not provide enough toxin to effectively treat all the nerves and sties of the branching, interdigitating and overlapping nerve zonal areas of pain symptoms. This leads to incomplete and potentially ineffective treatment of the migraine.

Yet another problem associated with the current FDA-approved protocol is that administration is intramuscular. Intramuscular administration of a Botulinum toxin does not necessarily target the sensory nerves responsible for the underlying symptoms of the migraine, but instead, the toxin is directed into the muscle and synaptic sites of motor neurons innervating the muscles causing undesirable consequences of muscle paralysis.

Thus, there is a need to develop a method and use of treating a migraine disorder that address the sporadic coverage and limited areas accessed with the currently available method for treating a migraine disorder which exhibit ineffective efficacy and unwanted associated side effects.

The present specification discloses methods and uses of treating a migraine disorder using higher total dosing and larger volumes of a Botulinum toxin. The disclosed methods and uses administer Botulinum toxin at most sites to nerves located in subcutaneous regions that are more superficial and extramuscular rather than into regions within the underlying muscle which are deep and intramuscular. In addition, the disclosed methods use a higher total dose of a Botulinum toxin as well as larger volumes at more extramuscular sites to ensure uniform coverage of all the sensory nerves responsible for the underlying symptoms of a migraine disorder. The disclosed methods and uses further include targeting of specific muscles associated with posttraumatic migraine

TABLE 1

FDA-Approved Migraine Treatment Using 5 units/100 µL of a Botulinum Toxin

| Site No. | Site Location | Targeted Nerve | Site Distribution | Site Total | Total Dose (Units) |
|---|---|---|---|---|---|
| 1 | Medial Corrugator Muscle | Supraorbital and Supratrochlear Nerves | 1 site/side | 2 | 10 |
| 2 | Procerus Muscle | Supraorbital Nerve | 1 | 1 | 5 |
| 3 | Frontalis Muscle | Supraorbital and Supratrochlear Nerves | 2 sites/side | 4 | 20 |
| 4 | Temporalis Muscle | Auriculotemporal Nerve | 4 sites/side | 8 | 40 |
| 5 | Occipitalis Muscle | Greater Occipital and Lesser Occipital Nerves | 3 sites/side | 6 | 30 |
| 6 | Cervical Paraspinal Muscle | Cervical Plexus | 2 sites/side | 4 | 20 |
| 7 | Trapezius Muscle | Supraclavicular Nerve | 3 sites/side | 6 | 30 |

One problem associated with the current FDA-approved protocol is that only 100 µL is used per injection site. The use of such a low administration volume per site is done in order to minimize diffusion of the toxin from the injection site, thereby reducing unwanted side effects such as paralysis unwanted adjacent muscles. The disadvantage of using a lower administration volume is that it limits exposure of the toxin to the nerves that are carry the pain signals within the designated areas and other symptoms associated with migraine. This leads to sporadic treatment coverage of the sensory nerves responsible for the migraine.

Another problem associated with the current FDA-approved protocol is that only 155 units are dosed. It is now known that the nerves responsible for carrying the pain headache leading to a more effective treatment while at the same time reducing the unwanted side effects of such a treatment of excessive and unwanted muscle paralysis. The disclosed methods and uses can further include administration of a Botulinum toxin to certain nerve exit point sites, which can be administered either intramuscularly or extramuscularly.

Aspects of the present specification disclose, in part, a method for treating a migraine disorder. As used herein, "treating" or "treatment" means to reduce or eliminate one or more physiological conditions or symptoms associated with a migraine disorder being experienced by an individual, either temporarily or permanently. This can include prophylactic applications to retard or prevent one or more physiological conditions or symptoms associated with a migraine disorder from manifesting in an individual, either temporarily or permanently.

In some embodiments, methods and uses for treating a migraine disorder disclosed herein comprise extramuscularly administering a Botulinum toxin to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual. In some embodiments, methods and uses for treating a migraine disorder disclosed herein further comprise extramuscularly administering a Botulinum toxin to one or more nerve exit points in the head and neck, one or more sites along a Supraclavicular nerve and/or a Cervical Nerve Plexus, one or more sites of an epicranial aponeurosis, or any combination thereof. In some embodiments, methods and uses for treating a migraine disorder disclosed herein further comprise intramuscularly administering a Botulinum toxin to one or more locations within a Splenius Capitus muscle, a Masseter muscle, a Trapezius muscle, a Sternocliedomastoid muscle or any combination thereof. As used herein, the term "extramuscular" or "extramuscularly" refers to a specific route of administration that avoids direct delivery of a Botulinum toxin into muscle tissue.

In some embodiments, methods and uses for treating a migraine disorder disclosed herein comprise subcutaneously administering a Botulinum toxin to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual. In some embodiments, methods and uses for treating a migraine disorder disclosed herein further comprise subcutaneously administering a Botulinum toxin to one or more nerve exit points in the head and neck, one or more sites along a Supraclavicular nerve and/or a Cervical Nerve Plexus, one or more sites of an epicranial aponeurosis, or any combination thereof. In some embodiments, methods and uses for treating a migraine disorder disclosed herein further comprise intramuscularly administering a Botulinum toxin to one or more locations within a Splenius Capitus muscle, a Masseter muscle, a Trapezius muscle, a Sternocleidomastoid muscle or any combination thereof. As used herein, the term "subcutaneous" or "subcutaneously" refers to a specific type of an extramuscularly administration that delivers a Botulinum toxin directly into the hypodermis (also known as the subcutis or superficial facia), a layer of tissue directly below the dermis.

In some embodiments, methods and uses disclosed herein do not intramuscularly administering a Botulinum toxin to an individual. In some embodiments, methods and uses disclosed herein intramuscularly administer a Botulinum toxin to an individual at one or more locations within a Splenius Capitus muscle, a Masseter muscle, a Trapezius muscle, a Sternocleidomastoid muscle or any combination thereof, but at no other intramuscular location. As used herein, the term "intramuscular" or "intramuscularly" refers to a specific route of administration where a Botulinum toxin is delivered directly into muscle tissue.

Aspects of the present specification disclose, in part, a Botulinum toxin. A Botulinum toxin is a neurotoxin produced by *Clostridium botulinum*, as well as a botulinum toxin (or the light chain or the heavy chain thereof) made recombinantly. A botulinum toxin encompasses a botulinum toxin complex, (for example, the 300 kDa, 600 kDa and 900 kDa complexes), as well as the neurotoxic component of the botulinum toxin (150 kDa) that is unassociated with the complex proteins. As used herein, the term "Botulinum toxin" excludes non-neurotoxins, such as the cytotoxic Botulinum toxin serotype C2 (Botulinum C2 toxin) and Botulinum toxin serotype C3 (Botulinum C3 toxin). In some embodiments, a Botulinum toxin includes a Botulinum toxin serotype A (Botulinum A toxin), a Botulinum toxin serotype B (Botulinum B toxin), a Botulinum toxin serotype C1 (Botulinum C1 toxin), a Botulinum toxin serotype D (Botulinum D toxin), a Botulinum toxin serotype E (Botulinum E toxin), a Botulinum toxin serotype F (Botulinum F toxin), a Botulinum toxin serotype G (Botulinum G toxin), or any combination thereof. In some embodiments, a Botulinum toxin includes a modified botulinum toxin of any one of serotype A, B, C1, D, E, F, or G, a re-engineered botulinum toxin of any one of serotype A, B, C1, D, E, F, or G, or an analog, a derivative, a homolog, a part, a sub-part, a variant, or a version of a modified botulinum toxin or a re-engineered botulinum toxin. Commercially available Botulinum toxins include BOTOX® (onabotulinumtoxinA), a Botulinum toxin type A neurotoxin complex, CS-BOT, (Japanese BTX-A), a Botulinum toxin type A neurotoxin, DYSPORT® (abobotulinumtoxinA), JEUVEAU® (prabotulinumtoxinA), a Botulinum toxin type A neurotoxin complex, a Botulinum toxin type A neurotoxin complex, MYOBLOC®, a Botulinum toxin type B neurotoxin complex, PROSIGNE® (Chinese BTX-A), a Botulinum toxin type A neurotoxin, and XEOMIN® (incobotulinumtoxinA), a 150 kDa botulinum toxin type A toxin.

The amount of a Botulinum toxin is administered in units. As used herein, the term "unit" or "units" refers to the potency or activity ascribed to a Botulinum toxin in internationally standardized mouse units (MU) based on U.S. Federal Drug Administration (FDA)-approved tests such as the mouse intraperitoneal (ip) $LD_{50}$ test. The units disclosed herein refer to units ascribed to onabotulinumtoxinA. However, because manufacturing methods differ, the units ascribed to other commercially available Botulinum toxins can vary from onabotulinumtoxinA. As a guide, OnabotulinumtoxinA has a potency that is 1) equivalent to incobotulinumtoxinA; 2) equivalent to prabotulinumtoxinA; 3) about 2.5 to 3 times greater than abobotulinumtoxinA; and 4) about 50 times greater than MYOBLOC®. Thus, incobotulinumtoxinA and prabotulinumtoxinA are each administered in the disclosed methods in an amount comparable to onabotulinumtoxinA amount while abobotulinumtoxinA is administered in the disclosed methods and uses in an amount that is about 2.5 to 3 times more than the onabotulinumtoxinA amount. MYOBLOC® is administered in the disclosed methods and uses in an amount that is about 50 times more than the onabotulinumtoxinA amount.

In some embodiments, the total dose of a Botulinum toxin administered to an individual using methods and uses disclosed herein is in the range of 195 units to 240 units. In some embodiments, the concentration of a Botulinum toxin administered to an individual using methods and uses disclosed herein is in the range of 100 units/2 mL to 100 units/4 mL of a Botulinum toxin, i.e., 5 units/100 µL to 5 units/200 µL of a Botulinum toxin. A Botulinum toxin is prepared by diluting 100 units of Botulinum toxin with 2 mL of a diluent (5 units/100 µL) or alternatively with 4 mL of a diluent (5 units/200 µL). Typically, a Botulinum toxin is diluted using water, preservative-free normal saline, non-preservative-free normal saline, or other suitable diluent.

In some embodiments, a Botulinum toxin includes Botulinum A toxin. In some embodiments, the total dose of a Botulinum A toxin administered to an individual using methods and uses disclosed herein is in the range of 195 units to 240 units. In some embodiments, the concentration of a Botulinum toxin A administered to an individual using methods and uses disclosed herein is in the range of 100 units/2 mL to 100 units/4 mL of a Botulinum toxin A, i.e., 5 units/100 μL to 5 units/200 μL of a Botulinum toxin A. A Botulinum toxin A is prepared by diluting 100 units of Botulinum toxin A with 2 mL of a diluent (5 units/100 μL) or alternatively with 4 mL of a diluent (5 units/200 μL). Typically, a Botulinum A toxin is diluted using water, preservative-free normal saline, non-preservative-free normal saline, or other suitable diluent.

In some embodiments, a Botulinum A toxin includes OnabotulinumtoxinA. In some embodiments, the total dose of an OnabotulinumtoxinA administered to an individual using methods and uses disclosed herein is in the range of 195 units to 240 units. In some embodiments, the concentration of an OnabotulinumtoxinA administered to an individual using methods and uses disclosed herein is in the range of 100 units/2 mL to 100 units/4 mL units of an OnabotulinumtoxinA, i.e., 5 units/100 μL to 5 units/200 μL of an OnabotulinumtoxinA. An OnabotulinumtoxinA is prepared by diluting 100 units of an OnabotulinumtoxinA with 2 mL of a diluent (5 units/100 μL) or alternatively with 4 mL of a diluent (5 units/200 μL). Typically, an OnabotulinumtoxinA is diluted using water, preservative-free normal saline, non-preservative-free normal saline, or other suitable diluent.

Aspects of the present specification disclose, in part, administration of a Botulinum toxin to a fronto-fascial layer, a temporoparietal-fascial layer, and/or an occipital-fascial layer. The fronto-, temporoparietal-, and/or occipital-fascial layers have running within them nerves that supply sensation to the head and neck. It is at these superficial, extramuscular locations where the nerves terminate in branches that overlap and interdigitate to form a network of nerves localized and concentrated in areas described as cluster zones. In these broader neuronal networks which underly the areas of migraine pain, larger volume and/or more administration sites along with a larger dose is delivered to "saturate" or flood the areas associated with a migraine disorder. In aspects of these embodiments, the disclosed methods and uses subcutaneously administer a Botulinum toxin to the fronto-, temporoparietal-, and occipital-fascial layers within which run the nerves that supply sensation to the head and neck.

In some embodiments, and as shown in FIG. 1A, methods and uses disclosed herein comprises extramuscularly administering a Botulinum toxin to symmetrical left and right frontal nerve cluster zones (LZI and RZI) located in an area of the fronto-fascial layer of the forehead. The extra-muscular fronto-fascial layer overlies the Frontalis muscle which is thin and quadrilateral in form and originates from the epicranial aponeurosis and attaches distally to the skin of the forehead and eyebrow. It is noted that the lower one-third of the Frontalis muscle is responsible for most of the elevation of the eyebrow. The muscle fibers from the Corrugator and Frontalis muscles interdigitate within the region of the medial brow.

Still referring to FIG. 1A, a left frontal nerve cluster zone is defined by a closed area having a first left frontal horizontal boundary, a second left frontal horizontal boundary, a first left frontal vertical boundary, and a second left frontal vertical boundary. The first left frontal horizontal boundary follows a scalp line and is located about 4.5 cm to 7.5 cm above and parallel to a left supraorbital ridge. The second left frontal horizontal boundary is located about 2 cm to about 3 cm below the first left frontal horizontal boundary. The first left frontal vertical boundary is located about 0.5 to about 1 cm laterally left from the midline of the forehead. The second left frontal vertical boundary is located in-line with a medial inferior edge of the left superior orbital ridge. A right frontal nerve cluster zone is defined by a closed area having a first right frontal horizontal boundary, a second right frontal horizontal boundary, a first right frontal vertical boundary, and a second right frontal vertical boundary. The first right frontal horizontal boundary follows a scalp line and is located about 4.5 cm to 7.5 cm above and parallel to a right supraorbital ridge. The second right frontal horizontal boundary is located about 2 cm to about 3 cm below the first right frontal horizontal boundary. The first right frontal vertical boundary is located about 0.5 to about 1 cm laterally right from the midline of the forehead. The second right frontal vertical boundary is located in-line with a medial inferior edge of the right superior orbital ridge. Each frontal nerve cluster zone comprise branches from the Supraorbital nerve, lateral branches of the Supratrochlear nerve and antero-medial branches of the auriculotemporal nerve which anatomize to form a network of nerves in each frontal nerve cluster zone. The right frontal nerve cluster zone (RZI) includes branches from the right Supraorbital, lateral branches of the right Supratrochlear nerves, antero-medial branches of the right auriculotemporal nerves. The left frontal nerve cluster zone (LZI) includes branches from the left Supraorbital and lateral branches of the left Supratrochlear nerves and anterio-medial branches of the left auriculotemporal nerves In aspects of this embodiment, methods and uses disclosed herein comprise extramuscularly administering 15 units of a Botulinum toxin to a right frontal nerve cluster zone of the fronto-fascial layer and 15 units of a Botulinum toxin to a left frontal nerve cluster zone of the fronto-fascial layer wherein the concentration of the Botulinum toxin is 5 units/100 μL. In other aspects of this embodiment, methods and uses disclosed herein comprise extramuscularly administering 20 units of a Botulinum toxin to a right frontal nerve cluster zone of the fronto-fascial layer and 20 units of a Botulinum toxin to a left frontal nerve cluster zone of the fronto-fascial layer wherein the concentration of the Botulinum toxin is 5 units/100 μL. In yet other aspects of this embodiment, methods and uses disclosed herein comprise extramuscularly administering 25 units of a Botulinum toxin to a right frontal nerve cluster zone of the fronto-fascial layer and 25 units of a Botulinum toxin to a left frontal nerve cluster zone of the fronto-fascial layer wherein the concentration of the Botulinum toxin is 5 units/100 μL. In still other aspects of this embodiment, methods and uses disclosed herein comprise extramuscularly administering 30 units of a Botulinum toxin to a right frontal nerve cluster zone of the fronto-fascial layer and 30 units of a Botulinum toxin to a left frontal nerve cluster zone of the fronto-fascial layer wherein the concentration of the Botulinum toxin is 5 units/100 μL.

In aspects of this embodiment, methods and uses disclosed herein comprise subcutaneously administering 15 units of a Botulinum toxin to a right frontal nerve cluster zone of the fronto-fascial layer and 15 units of a Botulinum toxin to a left frontal nerve cluster zone of the fronto-fascial layer wherein the concentration of the Botulinum toxin is 5 units/100 μL. In other aspects of this embodiment, methods and uses disclosed herein comprise subcutaneously administering 20 units of a Botulinum toxin to a right frontal nerve cluster zone of the fronto-fascial layer and 20 units of a Botulinum toxin to a left frontal nerve cluster zone of the fronto-fascial layer wherein the concentration of the Botulinum toxin is 5 units/100 μL. In yet other aspects of this embodiment, methods and uses disclosed herein comprise subcutaneously administering 25 units of a Botulinum toxin to a right frontal nerve cluster zone of the fronto-fascial layer and 25 units of a Botulinum toxin to a left frontal nerve cluster zone of the fronto-fascial layer wherein the concentration of the Botulinum toxin is 5 units/100 μL. In still other aspects of this embodiment, methods and uses disclosed herein comprise subcutaneously administering 30 units of a Botulinum toxin to a right frontal nerve cluster zone of the fronto-fascial layer and 30 units of a Botulinum toxin to a left frontal nerve cluster zone of the fronto-fascial layer wherein the concentration of the Botulinum toxin is 5 units/100 μL.

In aspects of this embodiment, methods and uses disclosed herein comprise extramuscularly administering 15 units of a Botulinum toxin to a right frontal nerve cluster zone of the fronto-fascial layer and 15 units of a Botulinum toxin to a left frontal nerve cluster zone of the fronto-fascial layer wherein the concentration of the Botulinum toxin is 5 units/200 μL. In other aspects of this embodiment, methods and uses disclosed herein comprise extramuscularly administering 20 units of a Botulinum toxin to a right frontal nerve cluster zone of the fronto-fascial layer and 20 units of a Botulinum toxin to a left frontal nerve cluster zone of the fronto-fascial layer wherein the concentration of the Botulinum toxin is 5 units/200 μL. In yet other aspects of this embodiment, methods and uses disclosed herein comprise extramuscularly administering 25 units of a Botulinum toxin to a right frontal nerve cluster zone of the fronto-fascial layer and 25 units of a Botulinum toxin to a left frontal nerve cluster zone of the fronto-fascial layer wherein the concentration of the Botulinum toxin is 5 units/200 μL. In still other aspects of this embodiment, methods and uses disclosed herein comprise extramuscularly administering 30 units of a Botulinum toxin to a right frontal nerve cluster zone of the fronto-fascial layer and 30 units of a Botulinum toxin to a left frontal nerve cluster zone of the fronto-fascial layer wherein the concentration of the Botulinum toxin is 5 units/200 μL.

In aspects of this embodiment, methods and uses disclosed herein comprise subcutaneously administering 15 units of a Botulinum toxin to a right frontal nerve cluster zone of the fronto-fascial layer and 15 units of a Botulinum toxin to a left frontal nerve cluster zone of the fronto-fascial layer wherein the concentration of the Botulinum toxin is 5 units/200 μL. In other aspects of this embodiment, methods and uses disclosed herein comprise subcutaneously administering 20 units of a Botulinum toxin to a right frontal nerve cluster zone of the fronto-fascial layer and 20 units of a Botulinum toxin to a left frontal nerve cluster zone of the fronto-fascial layer wherein the concentration of the Botulinum toxin is 5 units/200 μL. In yet other aspects of this embodiment, methods and uses disclosed herein comprise subcutaneously administering 25 units of a Botulinum toxin to a right frontal nerve cluster zone of the fronto-fascial layer and 25 units of a Botulinum toxin to a left frontal nerve cluster zone of the fronto-fascial layer wherein the concentration of the Botulinum toxin is 5 units/200 μL. In still other aspects of this embodiment, methods and uses disclosed herein comprise subcutaneously administering 30 units of a Botulinum toxin to a right frontal nerve cluster zone of the fronto-fascial layer and 30 units of a Botulinum toxin to a left frontal nerve cluster zone of the fronto-fascial layer wherein the concentration of the Botulinum toxin is 5 units/200 μL.

Figure 1B:
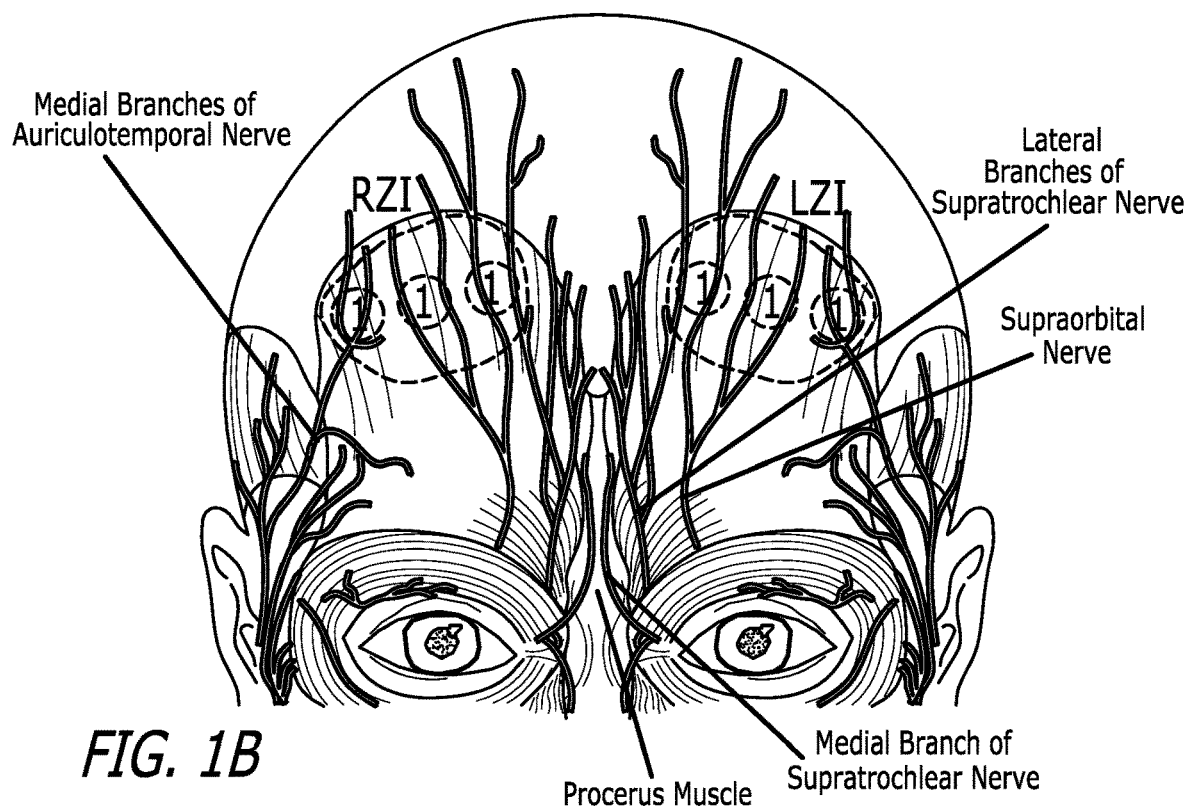

In some embodiment, and as shown in FIG. 1B, methods and uses disclosed herein comprise extramuscularly administering a Botulinum toxin at three locations within each of left and right frontal nerve cluster zones (LZI and RZI) located in an area of the fronto-fascial layer of the forehead. The three sites are located by dividing each frontal nerve cluster zone into three, equally spaced apart regions with an administration site located centrally within each region (labelled 1 in FIG. 1B). Each administration site within the left and right frontal nerve cluster zone of the fronto-fascial layer is administered 5 units of a Botulinum toxin. In aspects of this embodiment, each site within the left and right frontal nerve cluster zone of the fronto-fascial layer is extramuscularly administered 5 units/100 μL of a Botulinum toxin. In other aspects of this embodiment, each site within the left and right frontal nerve cluster zone of the fronto-fascial layer is subcutaneously administered 5 units/100 μL of a Botulinum toxin. In other aspects of this embodiment, each site within the left and right frontal nerve cluster zone of the fronto-fascial layer is extramuscularly administered 5 units/200 μL of a Botulinum toxin. In other aspects of this embodiment, each site within the left and right frontal nerve cluster zone of the fronto-fascial layer is subcutaneously administered 5 units/200 μL of a Botulinum toxin.

Figure 2A:
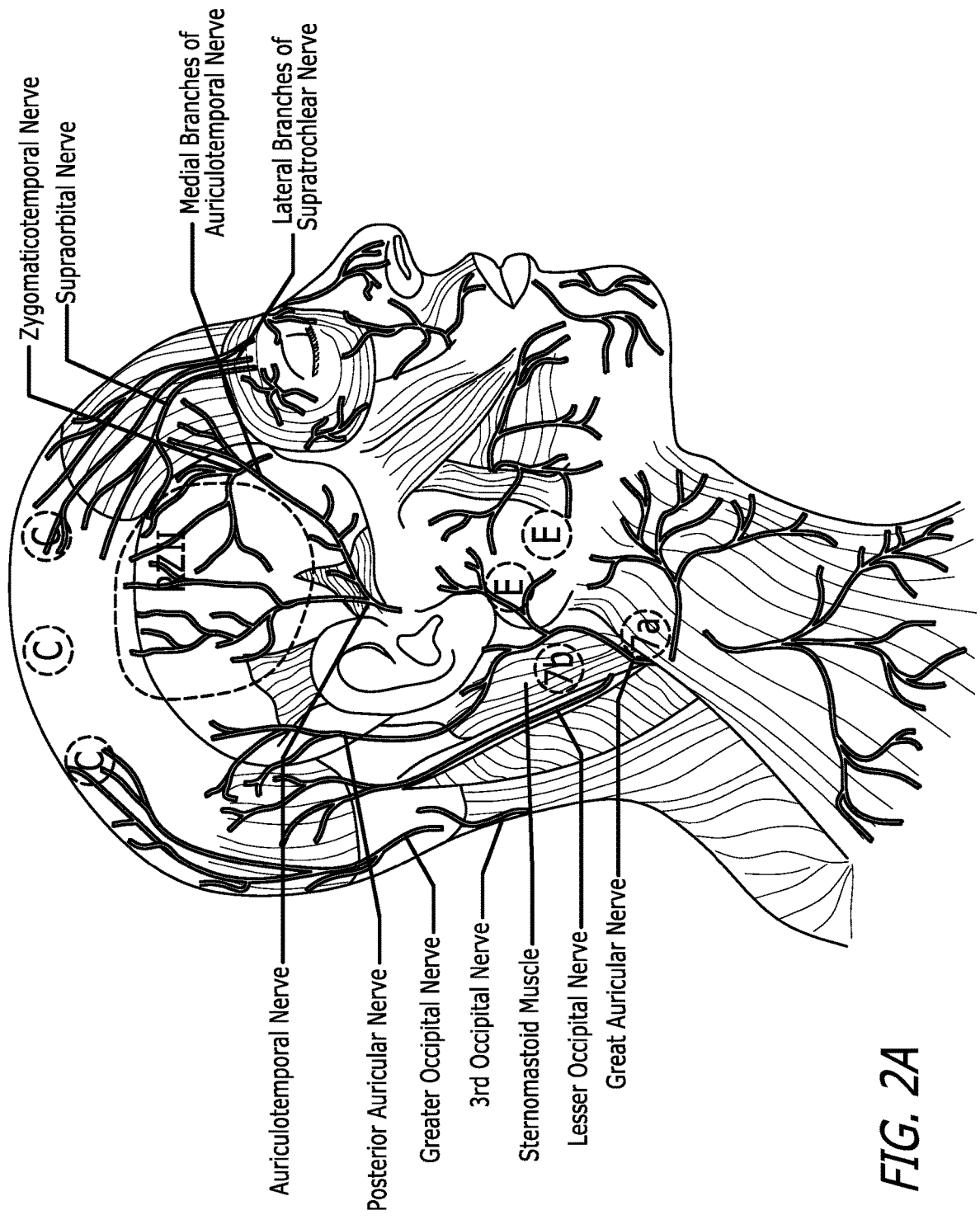
FIGS. 2A-B show an exemplary embodiment of a right temporal nerve cluster zone of the temporoparietal-fascial layer from a method and use disclosed herein with FIG. 2A showing exemplary right temporal nerve cluster zone RZII, fixed and additional extramuscular administration sites as well as optional intramusccular administration sites, and FIG. 2B showing exemplary administration sites located within right temporal nerve cluster zone RZII.

In some embodiments, and as shown in FIG. 2A, methods and uses disclosed herein comprise extramuscularly administering a Botulinum toxin to symmetrical left and right temporal nerve cluster zones (LZII and RZII) located in an area of the temporoparietal-fascial layer of the temples. The extramuscular temporoparietal-fascial layer overlies the Temporalis muscle is a broad fan shaped in form and originates from the temporal fossa and deep layer of the temporal fascia and inserts into the top and medial surface of the coronoid process of the mandible. Clenching the teeth helps locate the anterior perimeter of the temporal area.

Still referring to FIG. 2A, a left temporal nerve cluster zone is defined by a closed area having a first left temporal horizontal boundary, a second left temporal horizontal boundary, a first left temporal vertical boundary, and a second left temporal vertical boundary. The first left temporal horizontal boundary is in-line with and follows a curvature of a left superior temporal line. The second left temporal horizontal boundary is located about 1.5 cm to about 2 cm above and follows a superior aspect of a left zygomatic arch and a curvature of an outside edge of a left crux and a superior portion of a left helical rim of a left ear, The first left temporal vertical boundary is positioned in line with an outer dorsal edge of the left helical rim of the left ear. The second left temporal vertical boundary is positioned in line with a ventral edge of a head of a left condylar process of a left mandibular ramus. A right temporal nerve cluster zone is defined by a closed area having a first right temporal horizontal boundary, a second right temporal horizontal boundary, a first right temporal vertical boundary, and a second right temporal vertical boundary. The first right temporal horizontal boundary is in-line with and follows a curvature of a right superior temporal line. The second right temporal horizontal boundary is located about 1.5 cm to about 2 cm above and follows a superior aspect of a right zygomatic arch and a curvature of an outside edge of a right crux and a superior portion of a right helical rim of a right ear. The first right temporal vertical boundary is positioned in line with an outer dorsal edge of the right helical rim of the right ear. The second right temporal vertical boundary is positioned in line with a ventral edge of a head of a right condylar process of a right mandibular ramus. Each temporal nerve cluster zone comprises branches from the Auriculotemporal nerves, the posterior branches of the Supraorbital nerve, and some branches of the zygomaticotemporal nerve (V2) which anatomize to form a network of nerves in each temporal nerve cluster zone. The right temporal nerve cluster zone (RZII) includes branches of the right Auriculotemporal nerves as well as posterior branches of the right Supraorbital nerve, and some branches of the right zygomaticotemporal nerve (V2). The left temporal nerve cluster zone (LZII) includes branches of the left Auriculotemporal nerves as well as posterior branches of the left Supraorbital nerve, and some branches of the left zygomaticotemporal nerve (V2).

In aspects of this embodiment, methods and uses disclosed herein comprise extramuscularly administering 20 units of a Botulinum toxin to a right temporal nerve cluster zone of the temporoparietal-fascial layer and 20 units of a Botulinum toxin to a left temporal nerve cluster zone of the temporoparietal-fascial layer wherein the concentration of the Botulinum toxin is 5 units/100 µL. In other aspects of this embodiment, methods and uses disclosed herein comprise extramuscularly administering 25 units of a Botulinum toxin to a right temporal nerve cluster zone of the temporoparietal-fascial layer and 25 units of a Botulinum toxin to a left temporal nerve cluster zone of the temporoparietal-fascial layer wherein the concentration of the Botulinum toxin is 5 units/100 µL. In yet other aspects of this embodiment, methods and uses disclosed herein comprise extramuscularly administering 30 units of a Botulinum toxin to a right temporal nerve cluster zone of the temporoparietal-fascial layer and 30 units of a Botulinum toxin to a left temporal nerve cluster zone of the temporoparietal-fascial layer wherein the concentration of the Botulinum toxin is 5 units/100 µL. In still other aspects of this embodiment, methods and uses disclosed herein comprise extramuscularly administering 35 units of a Botulinum toxin to a right temporal nerve cluster zone of the temporoparietal-fascial layer and 35 units of a Botulinum toxin to a left temporal nerve cluster zone of the temporoparietal-fascial layer wherein the concentration of the Botulinum toxin is 5 units/100 µL. In some embodiments, extramuscular administration as disclosed herein within the right and left temporal nerve cluster zone avoids administration to the temporal branch of the facial nerve or in the vicinity of the zygomaticotemporal nerve branches of the facial nerve where such administration would impair the motor function of the zygomaticotemporal nerve branches of the facial nerve (7th Cranial Nerve—CNVII).

In aspects of this embodiment, methods and uses disclosed herein comprise subcutaneously administering 20 units of a Botulinum toxin to a right temporal nerve cluster zone of the temporoparietal-fascial layer and 20 units of a Botulinum toxin to a left temporal nerve cluster zone of the temporoparietal-fascial layer wherein the concentration of the Botulinum toxin is 5 units/100 µL. In other aspects of this embodiment, methods and uses disclosed herein comprise subcutaneously administering 25 units of a Botulinum toxin to a right temporal nerve cluster zone of the temporoparietal-fascial layer and 25 units of a Botulinum toxin to a left temporal nerve cluster zone of the temporoparietal-fascial layer wherein the concentration of the Botulinum toxin is 5 units/100 µL. In yet other aspects of this embodiment, methods and uses disclosed herein comprise subcutaneously administering 30 units of a Botulinum toxin to a right temporal nerve cluster zone of the temporoparietal-fascial layer and 30 units of a Botulinum toxin to a left temporal nerve cluster zone of the temporoparietal-fascial layer wherein the concentration of the Botulinum toxin is 5 units/100 µL. In still other aspects of this embodiment, methods and uses disclosed herein comprise subcutaneously administering 35 units of a Botulinum toxin to a right temporal nerve cluster zone of the temporoparietal-fascial layer and 35 units of a Botulinum toxin to a left temporal nerve cluster zone of the temporoparietal-fascial layer wherein the concentration of the Botulinum toxin is 5 units/100 µL. In some embodiments, extramuscular administration as disclosed herein within the right and left temporal nerve cluster zone avoids administration to the temporal branch of the facial nerve or in the vicinity of the zygomatico-temporal nerve branches of the facial nerve where such administration would impair the motor function of the zygomatico-temporal nerve branches of the facial nerve (7th Cranial Nerve—CNVII).

In aspects of this embodiment, methods and uses disclosed herein comprise extramuscularly administering 20 units of a Botulinum toxin to a right temporal nerve cluster zone of the temporoparietal-fascial layer and 20 units of a Botulinum toxin to a left temporal nerve cluster zone of the temporoparietal-fascial layer wherein the concentration of the Botulinum toxin is 5 units/200 µL. In other aspects of this embodiment, methods and uses disclosed herein comprise extramuscularly administering 25 units of a Botulinum toxin to a right temporal nerve cluster zone of the temporoparietal-fascial layer and 25 units of a Botulinum toxin to a left temporal nerve cluster zone of the temporoparietal-fascial layer wherein the concentration of the Botulinum toxin is 5 units/200 µL. In yet other aspects of this embodiment, methods and uses disclosed herein comprise extramuscularly administering 30 units of a Botulinum toxin to a right temporal nerve cluster zone of the temporoparietal-fascial layer and 30 units of a Botulinum toxin to a left temporal nerve cluster zone of the temporoparietal-fascial layer wherein the concentration of the Botulinum toxin is 5 units/200 µL. In still other aspects of this embodiment, methods and uses disclosed herein comprise extramuscularly administering 35 units of a Botulinum toxin to a right temporal nerve cluster zone of the temporoparietal-fascial layer and 35 units of a Botulinum toxin to a left temporal nerve cluster zone of the temporoparietal-fascial layer wherein the concentration of the Botulinum toxin is 5 units/200 µL. In some embodiments, extramuscular administration as disclosed herein within the right and left temporal nerve cluster zone avoids administration to the temporal branch of the facial nerve or in the vicinity of the zygomatico-temporal nerve branches of the facial nerve where such administration would impair the motor function of the zygomatico-temporal nerve branches of the facial nerve ($7^{th}$ Cranial Nerve—CNVII).

In aspects of this embodiment, methods and uses disclosed herein comprise subcutaneously administering 20 units of a Botulinum toxin to a right temporal nerve cluster zone of the temporoparietal-fascial layer and 20 units of a Botulinum toxin to a left temporal nerve cluster zone of the temporoparietal-fascial layer wherein the concentration of the Botulinum toxin is 5 units/200 µL. In other aspects of this embodiment, methods and uses disclosed herein comprise subcutaneously administering 25 units of a Botulinum toxin to a right temporal nerve cluster zone of the temporoparietal-fascial layer and 25 units of a Botulinum toxin to a left temporal nerve cluster zone of the temporoparietal-fascial layer wherein the concentration of the Botulinum toxin is 5 units/200 µL. In yet other aspects of this embodiment, methods and uses disclosed herein comprise subcutaneously administering 30 units of a Botulinum toxin to a right temporal nerve cluster zone of the temporoparietal-fascial layer and 30 units of a Botulinum toxin to a left temporal nerve cluster zone of the temporoparietal-fascial layer wherein the concentration of the Botulinum toxin is 5 units/200 µL. In still other aspects of this embodiment, methods and uses disclosed herein comprise subcutaneously administering 35 units of a Botulinum toxin to a right temporal nerve cluster zone of the temporoparietal-fascial layer and 35 units of a Botulinum toxin to a left temporal nerve cluster zone of the temporoparietal-fascial layer wherein the concentration of the Botulinum toxin is 5 units/200 µL. In some embodiments, extramuscular administration as disclosed herein within the right and left temporal nerve cluster zone avoids administration to the temporal branch of the facial nerve or in the vicinity of the zygomatico-temporal nerve branches of the facial nerve where such administration would impair the motor function of the zygomatico-temporal nerve branches of the facial nerve (7th Cranial Nerve—CNVII).

Figure 2B:
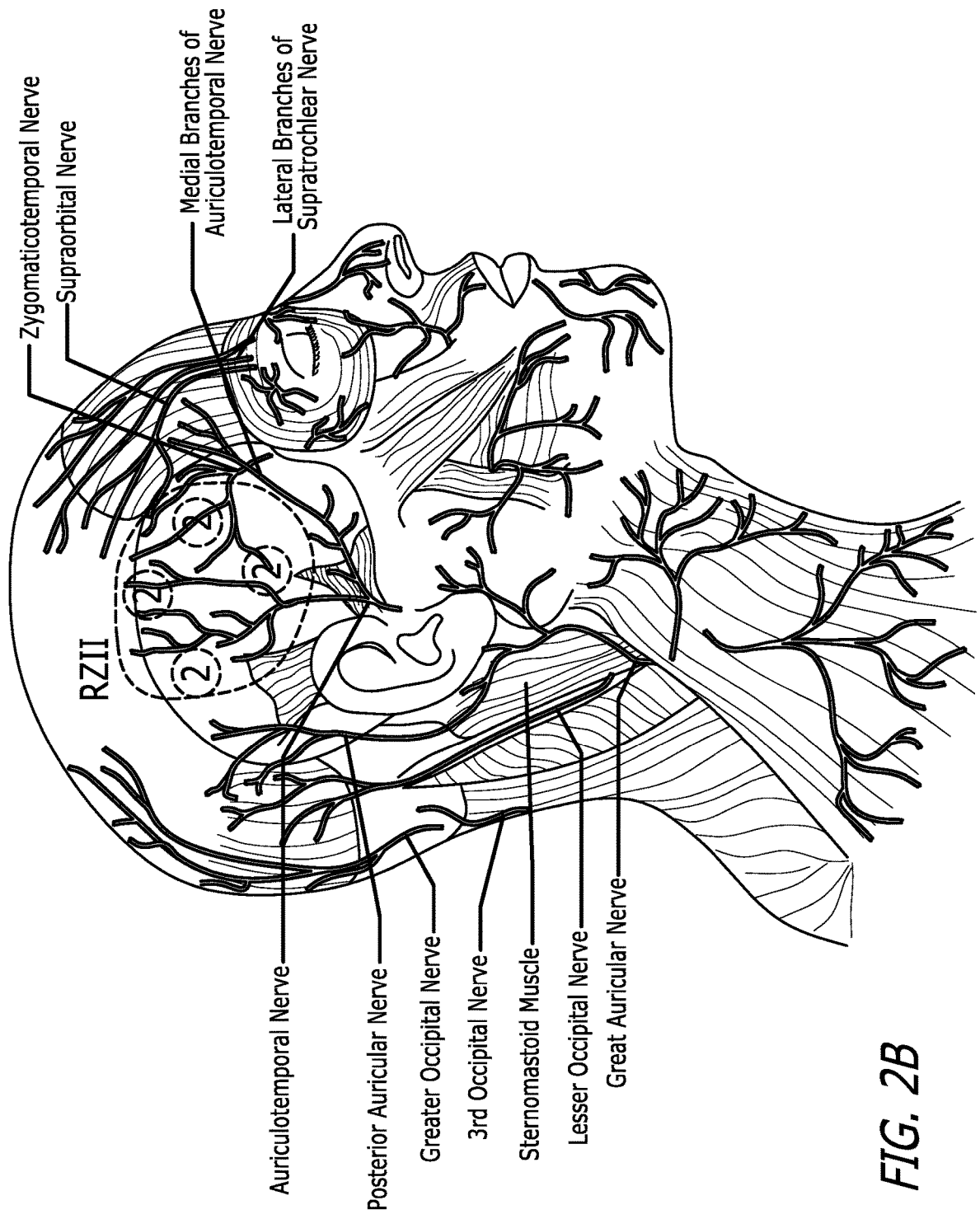

In some embodiment, and as shown in FIG. 2B methods and uses disclosed herein comprise extramuscularly administering a Botulinum toxin at four locations within each of left and right temporal nerve cluster zones (LZII and RZII) located in an area of the temporoparietal-fascial layer of the temple. In aspects of this embodiment, the four sites are located by divided each temporal nerve cluster zone into four, equally spaced apart quadrants with an administration site located in a centrally within each region (labelled 2 in FIG. 2B). In other aspects of this embodiment, four sites follow the path of the Auriculotemporal nerve, with the first site located about 2 cm to about 2.5 cm superior (cranial) and about 2 cm to about 2.5 cm ventral from the superior helical rim of the ear, the second site located about 1.5 cm to 2 cm above the first injection site, the third site located above a bulge of the anterior aspect of the temporalis muscle created when a person's teeth are clenched, and the fourth site located about 4.0 cm superior (cranial) to the superior helical rim of the ear (or about 1.5 cm dorsal and about 0.5 cm inferior (caudal) from the second injection site. Each administration site within the left and right temporal nerve cluster zone of the temporoparietal-fascial layer is administered 5 units of a Botulinum toxin. In aspects of this embodiment, each site within the left and right temporal nerve cluster zone of the temporoparietal-fascial layer is extramuscularly administered 5 units/100 µL of a Botulinum toxin. In other aspects of this embodiment, each site within the left and right temporal nerve cluster zone of the temporoparietal-fascial layer is subcutaneously administered 5 units/100 µL of a Botulinum toxin. In other aspects of this embodiment, each site within the left and right temporal nerve cluster zone of the temporoparietal-fascial layer is extramuscularly administered 5 units/200 µL of a Botulinum toxin. In other aspects of this embodiment, each site within the left and right temporal nerve cluster zone of the temporoparietal-fascial layer is subcutaneously administered 5 units/200 µL of a Botulinum toxin.

Figure 3A:
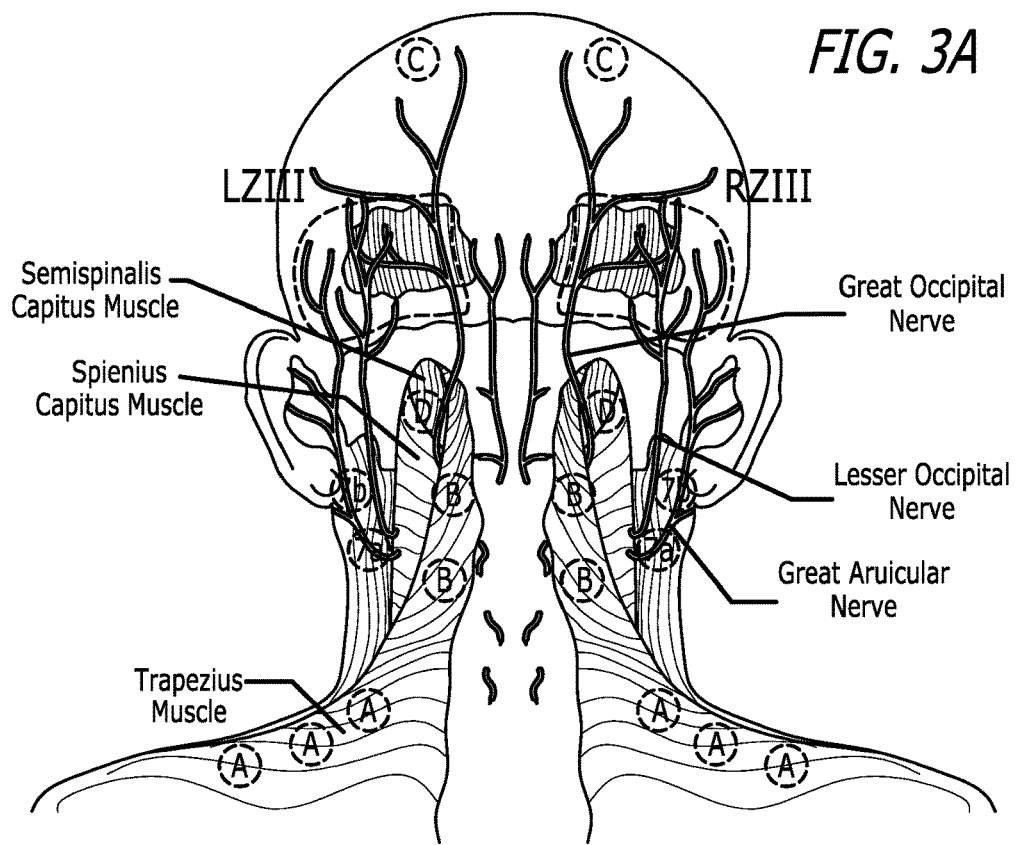

In some embodiments, and as shown in FIG. 3A, methods and uses disclosed herein comprise extramuscularly administering a Botulinum toxin to symmetrical left and right occipital nerve cluster zones (LZIII and RZIII) located in an area of the occipito-fascial layer of the back of the head. The extra-muscular occipito-fascial layer overlies the Occipitalis muscle is thin and quadrilateral in form and arises from tendinous fibers from the lateral two-thirds of the superior nuchal line of the occipital bone and from the mastoid process of the temporal bone and ends in the epicranial aponeurosis.

Still referring to FIG. 3A, a left occipital nerve cluster zone is defined by a closed area having a first left occipital horizontal boundary, a second left occipital horizontal boundary, a first left occipital vertical boundary, and a second left occipital vertical boundary. The first left occipital horizontal boundary is located about 3 cm above and runs parallel to a left superior aspect of a nuchal ridge. The second left occipital horizontal boundary is located in-line with the left superior aspect of the nuchal ridge. The first left occipital vertical boundary is located about 0.5 cm laterally left from an external occipital crest. The second left occipital vertical boundary is positioned in line with a left mastoid process and a dorsal portion of a left superior temporal line. A right occipital nerve cluster zone is defined by a closed area having a first right occipital horizontal boundary, a second right occipital horizontal boundary, a first right occipital vertical boundary, and a second right occipital vertical boundary. The first right occipital horizontal boundary is located about 3 cm above and follows a right superior aspect of the nuchal ridge. The second right occipital horizontal boundary is located in-line with the right superior aspect of the nuchal ridge. The first right occipital vertical boundary is located about 0.5 cm laterally right from the external occipital crest. The second right occipital vertical boundary is positioned in line with a right mastoid process and a dorsal portion of a right superior temporal line. Each occipital nerve cluster zone comprises branches from the Lesser Occipital nerve, lateral (peripheral) branches of the Greater Occipital nerve as well as posterior branches from the Posterior Auricular nerve (a branch of the Greater Auricular nerve) which anatomize to form a network of nerves in each occipital nerve cluster zone. The right occipital nerve cluster zone (RZIII) includes branches from the right Lesser Occipital nerve, lateral (peripheral) branches of the right Greater Occipital nerve as well as posterior branches from the right posterior auricular nerve (a branch of the right Greater Auricular nerve). The left occipital nerve cluster zone (LZIII) includes branches from the left Lesser Occipital nerve, lateral (peripheral) branches of the left Greater Occipital nerve as well as posterior branches from the left Posterior Auricular Nerve (a branch of the left Greater Auricular nerve).

In aspects of this embodiment, methods and uses disclosed herein comprise extramuscularly administering 30 units of a Botulinum toxin to a right occipital nerve cluster zone of the occipito-fascial layer and 30 units of a Botulinum toxin to a left occipital nerve cluster zone of the occipito-fascial layer wherein the concentration of the Botulinum toxin is 5 units/100 µL. In other aspects of this embodiment, methods and uses disclosed herein comprise extramuscularly administering 35 units of a Botulinum toxin to a right occipital nerve cluster zone of the occipito-fascial layer and 35 units of a Botulinum toxin to a left occipital nerve cluster zone of the occipito-fascial layer wherein the concentration of the Botulinum toxin is 5 units/100 µL.

In aspects of this embodiment, methods and uses disclosed herein comprise extramuscularly administering 40 units of a Botulinum toxin to a right occipital nerve cluster zone of the occipito-fascial layer and 40 units of a Botulinum toxin to a left occipital nerve cluster zone of the occipito-fascial layer wherein the concentration of the Botulinum toxin is 5 units/100 µL. In other aspects of this embodiment, methods and uses disclosed herein comprise extramuscularly administering 45 units of a Botulinum toxin to a right occipital nerve cluster zone of the occipito-fascial layer and 45 units of a Botulinum toxin to a left occipital nerve cluster zone of the occipito-fascial layer wherein the concentration of the Botulinum toxin is 5 units/100 µL. In yet other aspects of this embodiment, methods and uses disclosed herein comprise extramuscularly administering 50 units of a Botulinum toxin to a right occipital nerve cluster zone of the occipito-fascial layer and 50 units of a Botulinum toxin to a left occipital nerve cluster zone of the occipito-fascial layer wherein the concentration of the Botulinum toxin is 5 units/100 µL. In still other aspects of this embodiment, methods and uses disclosed herein comprise extramuscularly administering 55 units of a Botulinum toxin to a right occipital nerve cluster zone of the occipito-fascial layer and 55 units of a Botulinum toxin to a left occipital nerve cluster zone of the occipito-fascial layer wherein the concentration of the Botulinum toxin is 5 units/100 µL.

In aspects of this embodiment, methods and uses disclosed herein comprise subcutaneously administering 30 units of a Botulinum toxin to a right occipital nerve cluster zone of the occipito-fascial layer and 30 units of a Botulinum toxin to a left occipital nerve cluster zone of the occipito-fascial layer wherein the concentration of the Botulinum toxin is 5 units/100 µL. In other aspects of this embodiment, methods and uses disclosed herein comprise subcutaneously administering 35 units of a Botulinum toxin to a right occipital nerve cluster zone of the occipito-fascial layer and 35 units of a Botulinum toxin to a left occipital nerve cluster zone of the occipito-fascial layer wherein the concentration of the Botulinum toxin is 5 units/100 µL.

In aspects of this embodiment, methods and uses disclosed herein comprise subcutaneously administering 40 units of a Botulinum toxin to a right occipital nerve cluster zone of the occipito-fascial layer and 40 units of a Botulinum toxin to a left occipital nerve cluster zone of the occipito-fascial layer wherein the concentration of the Botulinum toxin is 5 units/100 µL. In other aspects of this embodiment, methods and uses disclosed herein comprise subcutaneously administering 45 units of a Botulinum toxin to a right occipital nerve cluster zone of the occipito-fascial layer and 45 units of a Botulinum toxin to a left occipital nerve cluster zone of the occipito-fascial layer wherein the concentration of the Botulinum toxin is 5 units/100 µL. In yet other aspects of this embodiment, methods and uses disclosed herein comprise subcutaneously administering 50 units of a Botulinum toxin to a right occipital nerve cluster zone of the occipito-fascial layer and 50 units of a Botulinum toxin to a left occipital nerve cluster zone of the occipito-fascial layer wherein the concentration of the Botulinum toxin is 5 units/100 µL. In still other aspects of this embodiment, methods and uses disclosed herein comprise subcutaneously administering 55 units of a Botulinum toxin to a right occipital nerve cluster zone of the occipito-fascial layer and 55 units of a Botulinum toxin to a left occipital nerve cluster zone of the occipito-fascial layer wherein the concentration of the Botulinum toxin is 5 units/100 µL.

In aspects of this embodiment, methods and uses disclosed herein comprise extramuscularly administering 30 units of a Botulinum toxin to a right occipital nerve cluster zone of the occipito-fascial layer and 30 units of a Botulinum toxin to a left occipital nerve cluster zone of the occipito-fascial layer wherein the concentration of the Botulinum toxin is 5 units/200 µL. In other aspects of this embodiment, methods and uses disclosed herein comprise extramuscularly administering 35 units of a Botulinum toxin to a right occipital nerve cluster zone of the occipito-fascial layer and 35 units of a Botulinum toxin to a left occipital nerve cluster zone of the occipito-fascial layer wherein the concentration of the Botulinum toxin is 5 units/200 µL.

In aspects of this embodiment, methods and uses disclosed herein comprise extramuscularly administering 40 units of a Botulinum toxin to a right occipital nerve cluster zone of the occipito-fascial layer and 40 units of a Botulinum toxin to a left occipital nerve cluster zone of the occipito-fascial layer wherein the concentration of the Botulinum toxin is 5 units/200 µL. In other aspects of this embodiment, methods and uses disclosed herein comprise extramuscularly administering 45 units of a Botulinum toxin to a right occipital nerve cluster zone of the occipito-fascial layer and 45 units of a Botulinum toxin to a left occipital nerve cluster zone of the occipito-fascial layer wherein the concentration of the Botulinum toxin is 5 units/200 µL. In yet other aspects of this embodiment, methods and uses disclosed herein comprise extramuscularly administering 50 units of a Botulinum toxin to a right occipital nerve cluster zone of the occipito-fascial layer and 50 units of a Botulinum toxin to a left occipital nerve cluster zone of the occipito-fascial layer wherein the concentration of the Botulinum toxin is 5 units/200 µL. In still other aspects of this embodiment, methods and uses disclosed herein comprise extramuscularly administering 55 units of a Botulinum toxin to a right occipital nerve cluster zone of the occipito-fascial layer and 55 units of a Botulinum toxin to a left occipital nerve cluster zone of the occipito-fascial layer wherein the concentration of the Botulinum toxin is 5 units/200 µL.

In aspects of this embodiment, methods and uses disclosed herein comprise subcutaneously administering 30 units of a Botulinum toxin to a right occipital nerve cluster zone of the occipito-fascial layer and 30 units of a Botulinum toxin to a left occipital nerve cluster zone of the occipito-fascial layer wherein the concentration of the Botulinum toxin is 5 units/200 µL. In other aspects of this embodiment, methods and uses disclosed herein comprise subcutaneously administering 35 units of a Botulinum toxin to a right occipital nerve cluster zone of the occipito-fascial layer and 35 units of a Botulinum toxin to a left occipital nerve cluster zone of the occipito-fascial layer wherein the concentration of the Botulinum toxin is 5 units/200 µL.

In aspects of this embodiment, methods and uses disclosed herein comprise subcutaneously administering 40 units of a Botulinum toxin to a right occipital nerve cluster zone of the occipito-fascial layer and 40 units of a Botulinum toxin to a left occipital nerve cluster zone of the occipito-fascial layer wherein the concentration of the Botulinum toxin is 5 units/200 µL. In other aspects of this embodiment, methods and uses disclosed herein comprise subcutaneously administering 45 units of a Botulinum toxin to a right occipital nerve cluster zone of the occipito-fascial layer and 45 units of a Botulinum toxin to a left occipital nerve cluster zone of the occipito-fascial layer wherein the concentration of the Botulinum toxin is 5 units/200 µL. In yet other aspects of this embodiment, methods and uses disclosed herein comprise subcutaneously administering 50 units of a Botulinum toxin to a right occipital nerve cluster zone of the occipito-fascial layer and 50 units of a Botulinum toxin to a left occipital nerve cluster zone of the occipito-fascial layer wherein the concentration of the Botulinum toxin is 5 units/200 µL. In still other aspects of this embodiment, methods and uses disclosed herein comprise subcutaneously administering 55 units of a Botulinum toxin to a right occipital nerve cluster zone of the occipito-fascial layer and 55 units of a Botulinum toxin to a left occipital nerve cluster zone of the occipito-fascial layer wherein the concentration of the Botulinum toxin is 5 units/200 µL.

Figure 3B:
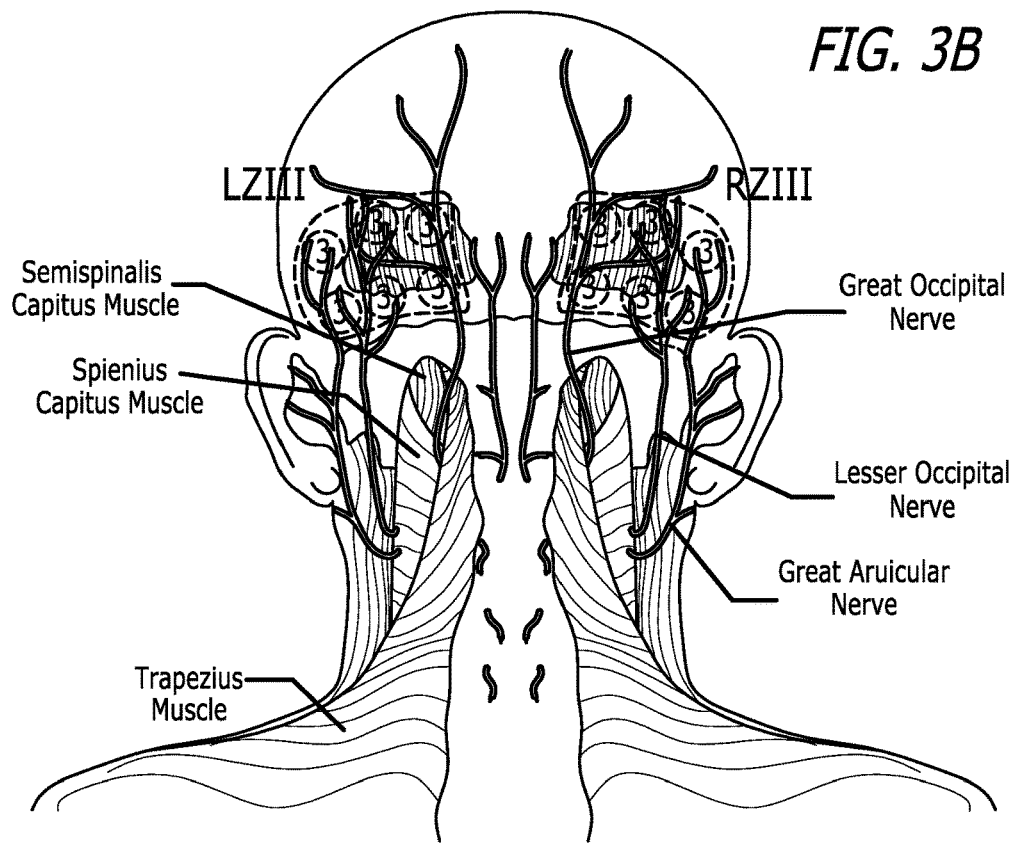

In some embodiment, and as shown in FIG. 3B, methods and uses disclosed herein comprise extramuscularly administering a Botulinum toxin at six locations within each of left and right occipital nerve cluster zones (LZIII and RZIII) located in an area of the occipito-fascial layer of the back of the head (labelled 3 in FIG. 3B). In aspects of this embodiment, the six sites are located in two rows of three with the first row located about 1 cm above the superior aspect of the nuchal ridge, with each site equally spaced apart from one another by about 1 cm from the lateral mastoid-temporal line and the midline occipital crest boundaries and the second row located about 2 cm above the superior aspect of the nuchal ridge, with each site equally spaced apart from one another by about 1 cm and the mastoid-temporal line and the occipital crest boundaries (i.e., about 1 cm above each of the three administration sites of the first row). Each administration site within the left and right occipital nerve cluster zone of the occipito-fascial layer is administered 5 units of a Botulinum toxin. In aspects of this embodiment, each site within the left and right occipital nerve cluster zone of the occipito-fascial layer is extramuscularly administered 5 units/100 µL of a Botulinum toxin. In other aspects of this embodiment, each site within the left and right occipital nerve cluster zone of the occipito-fascial layer is subcutaneously administered 5 units/100 µL of a Botulinum toxin. In other aspects of this embodiment, each site within the left and right occipital nerve cluster zone of the occipito-fascial layer is extramuscularly administered 5 units/200 µL of a Botulinum toxin. In other aspects of this embodiment, each site within the left and right occipital nerve cluster zone of the occipito-fascial layer is subcutaneously administered 5 units/200 µL of a Botulinum toxin.

In some embodiment, and as shown in FIG. 3C, methods and uses disclosed herein comprise extramuscularly administering a Botulinum toxin at eight locations within each of left and right occipital nerve cluster zones (LZIII and RZIII) located in an area of the occipito-fascial layer of the back of the head (labelled 3 in FIG. 3C). In aspects of this embodiment, the eight sites are located in two rows of four with the first row located about 1 cm above the superior aspect of the nuchal ridge, with each site equally spaced apart from one another by about 0.75 to about 1.0 cm and the mastoid-temporal line and the occipital crest boundaries and the second row located about 2 cm above the superior aspect of the nuchal ridge, with each site equally spaced apart from one another by about 0.75 to about 1.0 cm and the mastoid-temporal line and the occipital crest boundaries (i.e., about 1 cm above each of the four administration sites of the first row). Each administration site within the left and right occipital nerve cluster zone of the occipito-fascial layer is administered 5 units of a Botulinum toxin. In aspects of this embodiment, each site within the left and right occipital nerve cluster zone of the occipito-fascial layer is extramuscularly administered 5 units/100 µL of a Botulinum toxin. In other aspects of this embodiment, each site within the left and right occipital nerve cluster zone of the occipito-fascial layer is subcutaneously administered 5 units/100 µL of a Botulinum toxin. In other aspects of this embodiment, each site within the left and right occipital nerve cluster zone of the occipito-fascial layer is extramuscularly administered 5 units/200 µL of a Botulinum toxin. In other aspects of this embodiment, each site within the left and right occipital nerve cluster zone of the occipito-fascial layer is subcutaneously administered 5 units/200 µL of a Botulinum toxin.

Aspects of the present specification disclose, in part, administration of a Botulinum toxin to one or more nerve exit points in the head and neck, one or more sites along a Supraclavicular nerve and/or a Cervical Nerve Plexus, one or more sites of an epicranial aponeurosis, or any combination thereof. In some embodiments, and as shown in FIGS. 1A, 2A & 3A, methods and uses disclosed herein comprise extramuscularly administering a Botulinum toxin to additional sites in the head and neck. For example, additional administration site include one or more nerve exit points. These additional extramuscular administration sites are located outside of left and right frontal nerve cluster zones (LZI and RZI), left and right temporal nerve cluster zones (LZII and RZII), and left and right occipital nerve cluster zones (LZIII and RZIII).

As shown in FIG. 1A, the paired nerve exit points of Supraorbital and Supratrochlear nerves are located at the left and right Supraorbital and Supratrochlear foramen (labeled 4 and 5 respectively in FIG. 1A), the openings in the frontal bone located at the superior aspect of the left and right supraorbital margin. After exiting the foremen, the Supraorbital and Supratrochlear nerves immediately branch traveling superiorly through the Corrugator muscle, then medially over the Procerus muscle and then superiorly over the Frontalis muscle continuing to branch but doing so at a superficial level within the fascial layer superficial to the muscle. The corrugator muscle attaches to the nasal frontal bone medially and then to the skin of the eyebrow laterally. It is a medial brow depressor, pulling the medial one-half of the eyebrow downward. Contraction of these muscles creates vertical lines between the brows. Injection in this area will relax the corrugator and provide some elevation to the medial aspect of the eyebrow. By pressing upward and compressing the tissue at the bony superior orbital ridge, the Corrugator muscle will elevate exposing the Supraorbital and Supratrochlear foramen. Administration of a Botulinum toxin should be done by pointing the syringe and needle upward at a 45-degree angle to prevent inferior migration of toxin from the superior orbital rim to the upper eyelid thereby eliminating the potential for inferior spread of solution and thus preventing eyelid ptosis. In addition, the Corrugator muscles are relatively thin and a superficial administration of a Botulinum toxin over the mid aspect of these muscles will target most of the exiting nerve plexus of the supratrochlear and supraorbital nerves. Administration of a Botulinum toxin should be done with needle bevel up and pointing away from the skin which keeps the toxin, as it exits the point of the needle, within the more superficial plane of the fascia versus the underlying muscle. In addition, a slow delivery rate reduces spread of the solution to tissues and thus reduces pain of injection. As such, use of a 32-gauge needle is preferred in this location (lower areas of the forehead) as it reduces the rapid rate of delivery and prevents extravasation of diluent to other surrounding areas and keeps the solution within the desired areas. Each administration site of the paired nerve exit points of the Supraorbital and Supratrochlear nerves is administered 5 units of a Botulinum toxin. In aspects of this embodiment, each site of the paired nerve exit points of the Supraorbital and Supratrochlear nerves is extramuscularly administered 5 units/100 µL of a Botulinum toxin. In other aspects of this embodiment, each site of the paired nerve exit points of the Supraorbital and Supratrochlear nerves is subcutaneously administered 5 units/100 µL of a Botulinum toxin. In other aspects of this embodiment, each site of the paired nerve exit points of the Supraorbital and Supratrochlear nerves is extramuscularly administered 5 units/200 µL of a Botulinum toxin. In other aspects of this embodiment, each site of the paired nerve exit points of the Supraorbital and Supratrochlear nerves is subcutaneously administered 5 units/200 μL of a Botulinum toxin.

As shown in FIG. 1A, medial branches of the left and right Supratrochlear Nerves converge above the Procerus muscle (labelled 6 at FIG. 1A). The Procerus muscle is a small pyramidal slip of muscle that arises from the tendinous fibers of the fascia covering the lower part of the nasal bone and upper part of the lateral nasal cartilage. It is inserted into the skin over the lower part of the forehead between the two eyebrows on either side of the midline, its fibers merging with those of the Frontalis muscle. In some embodiments, and as shown in FIG. 1A, methods and uses disclosed herein comprise extramuscularly administering 5 units of a Botulinum toxin at a single location near the medial branches of the left and right Supratrochelar Nerve located subcutaneously above the central part of the procerus muscle. In aspects of this embodiment, a single location near the medial branches of the left and right Supratrochelar Nerve located subcutaneously above the central part of the procerus muscle is extramuscularly administered 5 units/100 μL of a Botulinum toxin. In other aspects of this embodiment, a single location near the medial branches of the left and right Supratrochelar Nerve located subcutaneously above the central part of the procerus muscle is subcutaneously administered 5 units/100 μL of a Botulinum toxin. In other aspects of this embodiment, a single location near the medial branches of the left and right Supratrochelar Nerve located subcutaneously above the central part of the procerus muscle is extramuscularly administered 5 units/200 μL of a Botulinum toxin. In other aspects of this embodiment, a single location near the medial branches of the left and right Supratrochelar Nerve located subcutaneously above the central part of the procerus muscle is subcutaneously administered 5 units/200 μL of a Botulinum toxin.

As shown in FIGS. 2A & 3A, the Greater Auricular nerve is located subcutaneously above the posterior edge of the midpoint of the left and right Sternocleidomastoid muscles. It is at this point that the Greater Auricula nerve enters into the subcutaneous region of the neck from deep within the neck region; in essence this is a nerve exit point. The sternocleidomastoid muscle is one of the largest and most superficial cervical muscles and originates at the manubrium of the sternum and the clavicle, and has an insertion at the mastoid process of the temporal bone of the skull. In some embodiment, methods and uses disclosed herein comprise extramuscularly administering a Botulinum toxin at an exit location of left and right Greater Auricular nerve (labelled 7a in FIGS. 2A & 3A) located subcutaneously above the posterior edge of the midpoint of the left and right Sternocleidomastoid muscles. In some embodiments, methods and uses disclosed herein comprise extramuscularly administering a Botulinum toxin at an optional second location along each of left and right Greater Auricular nerves located subcutaneously at a position midway between the mastoid process and a line drawn at the midpoint of the Sternocleidomastoid muscle (labelled 7b in FIGS. 2A & 3A). Each administration at an exit location or a location along the Greater Auricular nerve is administered 5 units of a Botulinum toxin. In aspects of this embodiment, each exit location and location along the left and right Greater Auricular nerves is extramuscularly administered 5 units/100 μL of a Botulinum toxin. In other aspects of this embodiment, each exit location and location along the left and right Greater Auricular nerves is subcutaneously administered 5 units/100 μL of a Botulinum toxin. In other aspects of this embodiment, each exit location and location along the left and right Greater Auricular nerves is extramuscularly administered 5 units/200 μL of a Botulinum toxin. In other aspects of this embodiment, each exit location and location along the left and right Greater Auricular nerves is subcutaneously administered 5 units/200 μL of a Botulinum toxin.

In aspects of this embodiment, methods and uses disclosed herein comprise extramuscularly administering a Botulinum toxin to one or more nerve exit points of the Supratrochlear nerve and the Supraorbital nerve, a location near the medial branches of the left and right Supratrochelar Nerve located subcutaneously above the central part of the procerus muscle, an exit location of the Greater Auricular nerve located subcutaneously above the posterior edge of the midpoint of the left and right Sternocleidomastoid muscles, and optionally one or more locations along the Greater Auricular nerve located subcutaneously above a position midway between the mastoid process and a line drawn at the midpoint of the Sternocleidomastoid muscle, or any combination thereof. Each of the one or more administration sites of 1) the one or more nerve exit points of the Supratrochlear nerve and the Supraorbital nerve, 2) a location near the medial branches of the left and right Supratrochelar Nerves located subcutaneously above the central part of the procerus muscle, and 3) an exit location of the Greater Auricular nerve located subcutaneously above the posterior edge of the midpoint of the left and right Sternocleidomastoid muscles, and 4) optionally one or more locations along the Greater Auricular nerve located subcutaneously above a position midway between the mastoid process and a line drawn at the midpoint of the Sternocleidomastoid muscle is administered 5 units of a Botulinum toxin.

In aspects of this embodiment, each of the one or more nerve exit points of the Supratrochlear nerve and the Supraorbital nerve, a location near the medial branches of the left and right Supratrochelar Nerves located subcutaneously above the central part of the procerus muscle, an exit location of the Greater Auricular nerve located subcutaneously above the posterior edge of the midpoint of the left and right Sternocledomastoid muscles, and optionally one or more locations along the Greater Auricular nerve located subcutaneously above a position midway between the mastoid process and a line drawn at the midpoint of the Sternoclidomastoid muscle is extramuscularly administered 5 units/100 μL of a Botulinum toxin. In other aspects of this embodiment, each of the one or more nerve exit points of the Supratrochlear nerve and the Supraorbital nerve, a location near the medial branches of the left and right Supratrochelar Nerves located subcutaneously above the central part of the procerus muscle, an exit location of the Greater Auricular nerve located subcutaneously above the posterior edge of the midpoint of the left and right Sternocledomastoid muscles, and optionally one or more locations along the Greater Auricular nerve located subcutaneously above a position midway between the mastoid process and a line drawn at the midpoint of the Sternoclidomastoid muscle is subcutaneously administered 5 units/100 μL of a Botulinum toxin. In other aspects of this embodiment, each of the one or more nerve exit points of the Supratrochlear nerve and the Supraorbital nerve, a location near the medial branches of the left and right Supratrochelar Nerves located subcutaneously above the central part of the procerus muscle, an exit location of the Greater Auricular nerve located subcutaneously above the posterior edge of the midpoint of the left and right Sternocledomastoid muscles, and optionally one or more locations along the Greater Auricular nerve located subcutaneously above a position midway between the mastoid process and a line drawn at the midpoint of the Sternoclidomastoid muscle is extramuscularly administered 5 units/200 µL of a Botulinum toxin. In other aspects of this embodiment, each of the one or more nerve exit points of the Supratrochlear nerve and the Supraorbital nerve, a location near the medial branches of the left and right Supratrochelar Nerves located subcutaneously above the central part of the procerus muscle, an exit location of the Greater Auricular nerve located subcutaneously above the posterior edge of the midpoint of the left and right Sternocledomastoid muscles, and optionally one or more locations along the Greater Auricular nerve located subcutaneously above a position midway between the mastoid process and a line drawn at the midpoint of the Sternoclidomastoid muscle is subcutaneously administered 5 units/200 µL of a Botulinum toxin.

In some embodiments, methods and uses disclosed herein further and optionally comprise extramuscularly administering a Botulinum toxin to one or more additional administration sites in the head and neck. In aspects of these embodiment, about 20 to 25 units of a Botulinum toxin is administered to one or more additional administration sites in the head and neck. Each of the one or more additional administration sites in the head and neck is administered 5 units of a Botulinum toxin. In aspects of this embodiment, each of the one or more additional administration sites in the head and neck is extramuscularly administered 5 units/100 µL of a Botulinum toxin. In other aspects of this embodiment, each of the one or more additional administration sites in the head and neck is subcutaneously administered 5 units/100 µL of a Botulinum toxin. In other aspects of this embodiment, each of the one or more additional administration sites in the head and neck is extramuscularly administered 5 units/200 µL of a Botulinum toxin. In other aspects of this embodiment, each of the one or more additional administration sites in the head and neck is subcutaneously administered 5 units/200 µL of a Botulinum toxin.

In some embodiment, methods and uses disclosed herein further and optionally comprise extramuscularly administering a Botulinum toxin to one or more additional administration sites by following the pain or other symptoms of a migraine disorder. As such, these additional administration sites are symptomatic sites where pain or other symptom of a migraine disorder manifest. Each of the one or more additional administration sites following the pain or other symptoms of a migraine disorder is administered 5 units of a Botulinum toxin. In aspects of this embodiment, each of the one or more additional administration sites following the pain or other symptoms of a migraine disorder is extramuscularly administered 5 units/100 µL of a Botulinum toxin. In other aspects of this embodiment, each of the one or more additional administration sites following the pain or other symptoms of a migraine disorder is subcutaneously administered 5 units/100 µL of a Botulinum toxin. In other aspects of this embodiment, each of the one or more additional administration sites following the pain or other symptoms of a migraine disorder is extramuscularly administered 5 units/ 200 µL of a Botulinum toxin. In other aspects of this embodiment, each of the one or more additional administration sites following the pain or other symptoms of a migraine disorder is subcutaneously administered 5 units/ 200 µL of a Botulinum toxin.

In some embodiments, methods and uses disclosed herein further and optionally comprise extramuscularly administering a Botulinum toxin to one or more additional administration sites located within the left and right frontal nerve clusters, the left and right temporal nerve clusters and the left and right occipital nerve clusters disclosed herein. In aspects of these embodiment, about 10 to 25 units of a Botulinum toxin is administered to one or more additional administration sites located within the left and right frontal nerve clusters, the left and right temporal nerve clusters and the left and right occipital nerve clusters disclosed herein. Each of the one or more additional administration sites located within the left and right frontal nerve clusters, the left and right temporal nerve clusters and the left and right occipital nerve clusters is administered 5 units of a Botulinum toxin. In aspects of this embodiment, each of the one or more additional administration sites located within the left and right frontal nerve clusters, the left and right temporal nerve clusters and the left and right occipital nerve clusters is extramuscularly administered 5 units/100 µL of a Botulinum toxin. In other aspects of this embodiment, each of the one or more additional administration sites located within the left and right frontal nerve clusters, the left and right temporal nerve clusters and the left and right occipital nerve clusters is subcutaneously administered 5 units/100 µL of a Botulinum toxin. In other aspects of this embodiment, each of the one or more additional administration sites located within the left and right frontal nerve clusters, the left and right temporal nerve clusters and the left and right occipital nerve clusters is extramuscularly administered 5 units/200 µL of a Botulinum toxin. In other aspects of this embodiment, each of the one or more additional administration sites located within the left and right frontal nerve clusters, the left and right temporal nerve clusters and the left and right occipital nerve clusters is subcutaneously administered 5 units/200 µL of a Botulinum toxin.

In some embodiment, methods and uses disclosed herein further and optionally comprise extramuscularly administering a Botulinum toxin to one or more additional administration sites located along the Supraclavicular nerve. As shown in FIG. 3A, the Supraclavicular nerve is located subcutaneously at the apical ridge of the superior portion of the left and right Trapezius muscles (labelled A at FIG. 3A). The Trapezius muscle is a large paired surface muscle that extends longitudinally from the occipital bone to the lower thoracic vertebrae of the spine and laterally to the spine of the scapula. The Supraclavicular nerves arise from the third and fourth Cervical nerves; they emerge beneath the posterior border of the Sternocleidomastoid muscle, and descend in the posterior triangle of the neck beneath the platysma and deep cervical fascia. In some embodiments, methods and uses disclosed herein comprise extramuscularly administering a Botulinum toxin at three paired sites along the left and right Supraclavicular nerve located subcutaneously at the apical ridge of the superior portion of the left and right Trapezius muscle. In aspects of these embodiments, methods and uses disclosed herein comprise administering a Botulinum toxin at three paired sites along the left and right Supraclavicular nerve located subcutaneously at the apical ridge of the superior portion of the left and right Trapezius muscle with the first site located at a point midway in the apical ridge of the superior portion of the left and right Trapezius muscle, the second site located at a point midway from the first site and acromion, and the third site located at a point midway from the first site and the necklace line. Each administration site of the paired sites along the left and right Supraclavicular nerve is administered 5 units of a Botulinum toxin. In aspects of this embodiment, each site of the paired sites along the left and right Supraclavicular nerve is extramuscularly administered 5 units/100 µL of a Botulinum toxin. In other aspects of this embodiment, each site of the paired sites along the left and right Supraclavicular nerve is subcutaneously administered 5 units/100 µL of a Botulinum toxin. In other aspects of this embodiment, each site of the paired sites along the left and right Supraclavicular nerve is extramuscularly administered 5 units/200 μL of a Botulinum toxin. In other aspects of this embodiment, each site of the paired sites along the left and right Supraclavicular nerve is subcutaneously administered 5 units/200 μL of a Botulinum toxin.

In some embodiment, methods and uses disclosed herein further and optionally comprise extramuscularly administering a Botulinum toxin to one or more additional administration sites located along the Cervical Nerve Plexus. The paired sites along the Cervical Nerve Plexus are located subcutaneously above the cervical vertebrae insertion sites of left and right Longissimus capitis and Longissimus cervicis muscles of the paraspinal muscle group. The longissimus cervicis (transversalis cervicis), situated medial to the longissimus thoracis, arises by long, thin tendons from the summits of the transverse processes of thoracic vertebrae 1-5, and is inserted by similar tendons into the posterior tubercles of the transverse processes of cervical vertebrae 2-6. The longissimus capitis (trachelomastoid muscle) lies medial to the longissimus cervicis, between it and the semispinalis capitis. It arises by tendons from the transverse processes of the upper four or five thoracic vertebrae, and the articular processes of the lower three or four cervical vertebrae, and is inserted into the posterior margin of the mastoid process, beneath the splenius capitis and sternocleidomastoid. The Cervical Nerve Plexus includes cutaneous branches of the Lesser Occipital nerve, the Greater Auricular nerve, the Transverse Cervical nerve and the Supraclavicular nerve. In some embodiments, and as shown in FIG. 3A, methods and uses disclosed herein comprise extramuscularly administering a Botulinum toxin t two sites on the left side of the Cervical Nerve Plexus and two sites on the right side of the Cervical Nerve Plexus above the cervical vertebrae insertion sites of left and right Longissimus capitis and Longissimus cervicis muscles (labelled B at FIG. 3A). This first site is located subcutaneously about 1 cm laterally from the spinal midline at the level of second cervical vertebrae. This second site is located subcutaneously about 1 cm laterally from the spinal midline at the level of third cervical vertebrae. Each administration site of the paired sites along the Cervical Nerve Plexus is administered 5 units of a Botulinum toxin. In aspects of this embodiment, each site of the paired sites along the Cervical Nerve Plexus is extramuscularly administered 5 units/100 μL of a Botulinum toxin. In other aspects of this embodiment, each site of the paired sites along the Cervical Nerve Plexus is subcutaneously administered 5 units/100 μL of a Botulinum toxin. In other aspects of this embodiment, each site of the paired sites along the Cervical Nerve Plexus is extramuscularly administered 5 units/200 μL of a Botulinum toxin. In other aspects of this embodiment, each site of the paired sites along the Cervical Nerve Plexus is subcutaneously administered 5 units/200 μL of a Botulinum toxin.

In some embodiments, additional administration sites include one or more locations along the Supraclavicular nerve, the Cervical Nerve Plexus, or any combination thereof. In aspects of these embodiment, about 10 to 25 units of a Botulinum toxin is administered to the one or more additional administration sites include one or more locations along the Supraclavicular nerve and the Cervical Nerve Plexus. Each of the one or more additional administration sites include one or more locations along the Supraclavicular nerve and the Cervical Nerve Plexus is administered 5 units of a Botulinum toxin. In aspects of this embodiment, each of the one or more additional administration sites include one or more locations along the Supraclavicular nerve and the Cervical Nerve Plexus is extramuscularly administered 5 units/100 μL of a Botulinum toxin. In other aspects of this embodiment, each of the one or more additional administration sites include one or more locations along the Supraclavicular nerve, and the Cervical Nerve Plexus is subcutaneously administered 5 units/100 μL of a Botulinum toxin. In other aspects of this embodiment, each of the one or more additional administration sites include one or more locations along the Supraclavicular nerve and the Cervical Nerve Plexus is extramuscularly administered 5 units/200 μL of a Botulinum toxin. In other aspects of this embodiment, each of the one or more additional administration sites include one or more locations along the Supraclavicular nerve and the Cervical Nerve Plexus is subcutaneously administered 5 units/200 μL of a Botulinum toxin.

In some embodiment, methods and uses disclosed herein further and optionally comprise extramuscularly administering a Botulinum toxin to one or more additional administration sites peripheral to the left and right frontal nerve cluster zones (LZI and RZI), the left and right temporal nerve cluster zones (LZII and RZII), and/or the left and right occipital nerve cluster zones (LZIII and RZIII). In aspects of these embodiment, about 10 units to 25 units of a Botulinum toxin is administered to the one or more administration sites peripheral to the left and right frontal nerve cluster zones (LZI and RZI), the left and right temporal nerve cluster zones (LZII and RZII), and/or the left and right occipital nerve cluster zones (LZIII and RZIII). Each of the one or more peripheral administration sites is administered 5 units of a Botulinum toxin. In aspects of this embodiment, each of the one or more peripheral sites is extramuscularly administered 5 units/100 μL of a Botulinum toxin. In other aspects of this embodiment, each of the one or more peripheral sites is subcutaneously administered 5 units/100 μL of a Botulinum toxin. In other aspects of this embodiment, each of the one or more peripheral sites is extramuscularly administered 5 units/200 μL of a Botulinum toxin. In other aspects of this embodiment, each of the one or more peripheral sites is subcutaneously administered 5 units/200 μL of a Botulinum toxin. One non-limiting example of such peripheral administration sites are located in the epicranial aponeurosis.

In some embodiment, methods and uses disclosed herein further and optionally comprise extramuscularly administering a Botulinum toxin to one or more additional administration sites in the epicranial aponeurosis (labelled C in FIGS. 1A, 2A & 3A). The epicranial aponeurosis (aponeurosis epicranialis, galea aponeurotica) is a tough layer of dense fibrous tissue which covers the upper part of the cranium and connects the Occipitalis and Frontalis muscles. Branches from the Supraorbital, Supratrochlear, Lesser Occipital, Greater Occipital, and Auriculotemporal Nerves run through the epicranial aponeurosis. In aspects of these embodiment, about 10 units to 25 units of a Botulinum toxin is administered to the one or more administration sites of the epicranial aponeurosis. Each of the one or more administration sites of the epicranial aponeurosis is administered 5 units of a Botulinum toxin. In aspects of this embodiment, each of the one or more sites of the epicranial aponeurosis is extramuscularly administered 5 units/100 μL of a Botulinum toxin. In other aspects of this embodiment, each of the one or more sites of the epicranial aponeurosis is subcutaneously administered 5 units/100 μL of a Botulinum toxin. In other aspects of this embodiment, each of the one or more sites of the epicranial aponeurosis is extramuscularly administered 5 units/200 μL of a Botulinum toxin. In other aspects of this embodiment, each of the one or more sites of the epicranial aponeurosis is subcutaneously administered 5 units/200 μL of a Botulinum toxin.

A botulinum toxin is administered locally and parenterally. A local administration of a Botulinum toxin is an administration to or in the vicinity of a symptomatic site in an individual by a non-systemic route. Thus, local administration excludes systemic routes of administration, such as intravenous or oral administration. In some embodiments, a Botulinum toxin disclosed herein is extramuscular or subcutaneous administer by injection as a bolus. A Botulinum toxin disclosed herein may be delivered to an individual by injection using a pre-filled syringe or autoinjector containing a Botulinum toxin disclosed herein. In some embodiments, a Botulinum toxin disclosed herein is extramuscular or subcutaneous administer by injection using a 30-gauge or 32-gauge, half-inch needle, and a 1 mL syringe. The volume and location of injections are designed to concentrate treatment to the target areas of the fascial layers within which run the nerves that supply sensation to the head and neck and are correlated with areas most often associated with post-traumatic headache and migraine pain. In aspects of this embodiment, extramuscular or subcutaneous administration to sites in the forehead is achieved using 32-gauge needle whereas extramuscular or subcutaneous administration to sites located in the other areas of the head, neck and/or shoulder is achieved using 30-gauge needle. In other aspects of this embodiment, extramuscular or subcutaneous administration to sites at the nerve exit points at Supratrochlear foramen, Supraorbital foramen, and above Procerus muscle as well as sites in the left and right frontal nerve clusters of the fronto-fascial layer is achieved using 32-gauge needle whereas extramuscular or subcutaneous administration to sites in the other areas of the head, neck and/or shoulder is achieved using 30-gauge needle. In yet other aspects of this embodiment, extramuscular or subcutaneous administration to sites at the nerve exit points at the Supratrochlear foramen, the Supraorbital foramen, and above the Procerus muscle as well as sites in the left and right frontal nerve clusters of the fronto-fascial layer is achieved using 32-gauge needle whereas extramuscular or subcutaneous administration to sites in the left and right temporal nerve clusters of temporoparietal-fascial layer, the left and right occipital nerve clusters of the occipito-fascial layer and sites at the nerve exit points above the Sternocleidomastoid muscle and the Trapezius muscle is achieved using 30-gauge needle. In still other aspects of this embodiment, extramuscular or subcutaneous administration to sites at the nerve exit points at Supratrochlear foramen, Supraorbital foramen, and above Procerus muscle as well as sites in the left and right frontal nerve clusters of the fronto-fascial layer is achieved using 32-gauge needle whereas extramuscular or subcutaneous administration to sites in the left and right temporal nerve clusters of temporoparietal-fascial layer, the left and right occipital nerve clusters of the occipito-fascial layer and sites at the nerve exit points above the Sternocleidomastoid muscle and the Splenius Capitus muscle is achieved using 30-gauge needle.

Aspects of the present specification disclose, in part, methods and uses disclosed herein further and optionally comprising intramuscular administration of a Botulinum toxin to one or more locations within the head and neck. Such optional intramuscular administrations would be employed only if necessary, in order to complete or enhance a therapy. In some embodiments, methods and uses disclosed herein further and optionally comprise intramuscular administration of a Botulinum toxin to one or more locations within a Splenius Capitus muscle, a Masseter muscle, a Trapezius muscle, a Sternocleidomastoid muscle or any combination thereof. In some embodiments, and as shown in FIGS. 2A & 3A, additional intramuscular administration site include one or more locations within the left and right Splenius Capitus muscle, the left and right Masseter muscles, the left and right Trapezius muscles, the left and right sternocleidomastoid muscles, or any combination thereof. Such intramuscular administration if typically employed when treating a whiplash component either alone or in association with a posttraumatic migraine disorder. These additional intramuscular administration sites are located outside of left and right frontal nerve cluster zones (LZI and RZI), left and right temporal nerve cluster zones (LZII and RZII), and left and right occipital nerve cluster zones (LZIII and RZIII).

In some embodiment, methods and uses disclosed herein further and optionally comprise intramuscularly administering a Botulinum toxin to one or more additional administration sites in the left and right Splenius Capitus muscles. This intramuscular administration site of a Botulinum toxin is typically performed on an individual suffering from post-traumatic migraine disorder attributed, at least in part, to whiplash or similar neck sprain or strain. As shown in FIG. 3A, the paired nerve exit points of the Cervical Nerve Plexus is located subcutaneously above the soft triangular depression just cranially of the superior edge of left and right Splenius Capitus muscles. The Splenius Capitus muscle is a paired, broad, straplike muscle in the back of the neck and arises from the lower half of the nuchal ligament, from the spinous process of the seventh cervical vertebra, and from the spinous processes of the upper three or four thoracic vertebrae. It pulls on the base of the skull from the vertebrae in the neck and upper thorax. It is involved in movements such as shaking the head and is often implicated in stiff neck and involved in head trauma associated with whiplash. The Cervical Nerve Plexus includes cutaneous branches of the Lesser Occipital nerve, the Greater Auricular nerve, the Transverse Cervical nerve and the Supraclavicular nerve. In some embodiments, and as shown in FIG. 3A, methods and uses disclosed herein comprise intramuscularly administering a Botulinum toxin at a single location at each of left and right Splenius Capitus muscles in the vicinity of the nerve exit point of the Cervical Nerve Plexus (labelled D at FIG. 3A). This site is located at a soft triangular depression about 1 cm below the nuchal ridge and between the insertion of the Trapezius muscle and the insertion of the Sternomastoid muscles at the base of the skull. Each paired administration site of the left and right Splenius Capitus muscles is administered 5 units of a Botulinum toxin. In aspects of this embodiment, each paired site of the left and right Splenius Capitus muscles is intramuscularly administered 5 units/100 μL of a Botulinum toxin. In other aspects of this embodiment, each paired site of the left and right Splenius Capitus muscles is intramuscularly administered 5 units/200 μL of a Botulinum toxin.

In some embodiment, methods and uses disclosed herein further and optionally comprise intramuscularly administering a Botulinum toxin to one or more additional administration sites in the left and right Masseter muscles. The paired nerve exit points of the Mandibular nerve (branch of Trigeminal Nerve) is located subcutaneously above the left and right Masseter muscles near the angle of the mandibular ramus of the mandible. The masseter muscles are a thick, somewhat quadrilateral in shaped, consisting of two heads. The superficial head arises by a thick, tendinous aponeurosis from the temporal process of the zygomatic bone, and from the anterior two-thirds of the inferior border of the zygomatic arch. Its fibers pass inferior and posterior, whereby they insert into the angle of the mandible and inferior half of the lateral surface of the ramus of the mandible. The deep head arises from the posterior third of the lower border and from the whole of the medial surface of the zygomatic arch. Its fibers pass downward and forward, whereby they insert into the upper half of the ramus as high as the coronoid process of the mandible. A branch of the left and right Trigeminal nerves, the large sensory root of the left and right Mandibular nerves exits the cranial cavity through the foramen ovale, and each gives rise to the Buccal branch, the Auriculotemporal branch and the Lingual branch. In some embodiments, as shown in FIG. 2A, methods and uses disclosed herein comprise intramuscularly administering a Botulinum toxin at two paired sites of the left and right Masseter muscles near the angle of the mandibular ramus of the mandible (labelled E at FIG. 2A). The first site is located about 0.5 cm ventrally and about 0.5 cm above (cranially) from the angle of the mandibular ramus of the mandible. The second site is located about 1.5 cm ventrally and about 0.5 cm above (cranially) from the angle of the mandibular ramus of the mandible. Each administration site of the paired Masseter muscles is administered 5 units of a Botulinum toxin. In aspects of this embodiment, each of the left and right Masseter muscles is intramuscularly administered 5 units/100 µL of a Botulinum toxin. In other aspects of this embodiment, each of the left and right Masseter muscles is intramuscularly administered 5 units/ 200 µL of a Botulinum toxin.

In some embodiment, methods and uses disclosed herein further and optionally comprise intramuscularly administering a Botulinum toxin to one or more additional administration sites in the left and right Trapezius muscles. Generally, these intramuscular administration sites are located in the same vicinity as the extramuscular administration sites located along the Supraclavicular nerve. In aspects of these embodiments, methods and uses disclosed herein comprise administering a Botulinum toxin at three paired intramuscular sites of the left and right Trapezius muscles with the first site located at a point midway in the apical ridge of the superior portion of the left and right Trapezius muscle, the second site located at a point midway from the first site and acromion, and the third site located at a point midway from the first site and the necklace line (labelled A in FIG. 3A). Each intramuscularly administration site of the paired Trapezius muscles is administered 5 units of a Botulinum toxin. In aspects of this embodiment, each of the left and right Trapezius muscles is intramuscularly administered 5 units/ 100 µL of a Botulinum toxin. In other aspects of this embodiment, each of the left and right Trapezius muscles is intramuscularly administered 5 units/200 µL of a Botulinum toxin.

In some embodiment, methods and uses disclosed herein further and optionally comprise intramuscularly administering a Botulinum toxin to one or more additional administration sites in the left and right Sternocleidomastoid muscles. Generally, these intramuscular administration sites are located in the same vicinity as the extramuscular administration sites located along the Greater Auricular nerve. In aspects of these embodiments, methods and uses disclosed herein comprise administering a Botulinum toxin at three paired intramuscular sites of the left and right Sternocleidomastoid muscles located subcutaneously at a position midway between the mastoid process and a line drawn at the midpoint of the Sternocleidomastoid muscle (labelled 7b in FIGS. 2A & 3A). Each intramuscularly administration site of the paired Sternocleidomastoid muscles is administered 5 units of a Botulinum toxin. In aspects of this embodiment, each of the left and right Sternocleidomastoid muscles is intramuscularly administered 5 units/100 µL of a Botulinum toxin. In other aspects of this embodiment, each of the left and right Sternocleidomastoid muscles is intramuscularly administered 5 units/200 µL of a Botulinum toxin.

In some embodiments, methods and uses for treating a migraine disorder disclosed herein can comprise a single Botulinum toxin therapy or a repeated Botulinum toxin therapy. In some embodiments, disclosed methods and uses can be periodically repeated to maintain the therapeutic and beneficial effects of a Botulinum toxin therapy. In some embodiments, methods and uses disclosed herein administer a Botulinum toxin disclosed herein to the individual multiple times per year. In aspects of these embodiments, methods and uses disclosed herein administer a Botulinum toxin disclosed herein to the individual, e.g., once every month, once every two months, once every three months, once every four months, once every five months, once every six months, once every seven months, once every eight months, once every nine months, once every ten months, once every eleven months, once every twelve months, or any combination thereof.

In some embodiments, methods and uses disclosed herein administer a Botulinum toxin disclosed herein to the individual at a dose sufficient to reduce or eliminate one or more physiological conditions or symptoms associated with a migraine disorder experienced by an individual. In some embodiments, methods and uses disclosed herein administer a Botulinum toxin disclosed herein to the individual at a dose sufficient to reduce or eliminate one or more physiological conditions or symptoms associated with a migraine disorder experienced by an individual as compared to one or more symptoms associated with a migraine disorder experienced by another matched individual not receiving the Botulinum toxin disclosed herein (i.e., a control individual). A Botulinum toxin disclosed herein is administered in a dose sufficient to treat a migraine disorder. As used herein, the term "dose sufficient" included "amount sufficient", "effective amount", "effective dose", "therapeutically effective amount" or "therapeutically effective dose" and refers to the minimum amount of a Botulinum toxin disclosed herein necessary to achieve the desired therapeutic effect and includes an amount sufficient to reduce one or more physiological conditions or symptom associated with a migraine disorder.

In aspects of this embodiment, methods and uses disclosed herein administer a Botulinum toxin disclosed herein to the individual at a dose sufficient to reduce or eliminate one or more physiological conditions or symptoms associated with a migraine disorder by, e.g., at least 10%, at least 20%, at least 30%, at least 40%, at least 50%, at least 60%, at least 70%, at least 80%, at least 90% or at least 95% or more. In other aspects of this embodiment, methods and uses disclosed herein administer a Botulinum toxin disclosed herein to the individual at a dose sufficient to reduce or eliminate one or more physiological conditions or symptoms associated with a migraine disorder by, e.g., at most 10%, at most 20%, at most 30%, at most 40%, at most 50%, at most 60%, at most 70%, at most 80%, at most 90% or at most 100%. In yet other aspects of this embodiment, methods and uses disclosed herein administer a Botulinum toxin disclosed herein to the individual at a dose sufficient to reduce or eliminate one or more physiological conditions or symptoms associated with a migraine disorder by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, methods and uses disclosed herein administer a Botulinum toxin disclosed herein to the individual at a dose sufficient to reduce or eliminate one or more physiological conditions or symptoms associated with a migraine disorder for, e.g., at least one week, at least one month, at least two months, at least three months, at least four months, at least five months, at least six months, at least seven months, at least eight months, at least nine months, at least ten months, at least eleven months, or at least twelve months.

In some embodiments, methods and uses disclosed herein administer a Botulinum toxin disclosed herein to the individual at a dose sufficient to reduce the number of migraine days experienced by an individual over the course of a month as compared to the number of monthly migraine days experienced by the individual prior to administration of the Botulinum toxin disclosed herein (i.e. individual's pre-treatment baseline) and/or the number of monthly migraine days experienced by another matched individual not receiving the Botulinum toxin disclosed herein (i.e., a control individual). A migraine day is any calendar day or a portion of a calendar day during which an individual experiences the onset, continuation, or recurrence of a migraine disclosed herein with or without aura lasting greater than 30 minutes. A migraine includes a headache associated with nausea or vomiting or sensitivity to light or sound and/or a headache characterized by at least two of the following pain features: unilateral pain, throbbing pain, moderate to severe pain intensity, or pain exacerbated by physical activity. The pre-treatment baseline can be established by determining the relevant parameter (e.g. number of migraine days) in one, two, three, four, five, or six or more months prior to administration of a Botulinum toxin disclosed herein. In some embodiments, the pre-treatment baseline is established based on the measurement of the particular parameter in the three months prior to administration of a Botulinum toxin disclosed herein. In some embodiments, a dose sufficient to reduce the number of monthly migraine days in an individual in need thereof is about 195 units to about 240 units.

In aspects of these embodiments, methods and uses disclosed herein administer a Botulinum toxin disclosed herein to the individual at a dose that reduces the number of monthly migraine days experienced by the individual by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine days experienced by the individual by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that reduces the number of monthly migraine days experienced by the individual by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that reduces the number of monthly migraine days experienced by the individual by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine days experienced by the individual by at least 75% following administration of a Botulinum toxin disclosed herein as compared to a pre-treatment baseline and/or a control individual.

In some embodiments, methods and uses disclosed herein administer a Botulinum toxin disclosed herein to the individual at a dose sufficient to reduce the number of migraine hours experienced by an individual over the course of a month as compared to the number of monthly migraine hours experienced by the individual prior to administration of the Botulinum toxin disclosed herein (i.e. individual's pre-treatment baseline) and/or the number of monthly migraine hours experienced by another matched individual not receiving the Botulinum toxin disclosed herein (i.e., a control individual). A migraine hour is any hour or portion of an hour during which an individual experiences the onset, continuation, or recurrence of a migraine disclosed herein with or without aura. The pre-treatment baseline can be established by determining the relevant parameter (e.g. number of migraine hours) in one, two, three, four, five, or six or more months prior to administration of a Botulinum toxin disclosed herein. In some embodiments, the pre-treatment baseline is established based on the measurement of the particular parameter in the three months prior to administration of a Botulinum toxin disclosed herein. In some embodiments, a dose sufficient to reduce the number of monthly migraine hours in an individual in need thereof is about 195 units to about 240 units.

In aspects of these embodiments, methods and uses disclosed herein administer a Botulinum toxin disclosed herein to the individual at a dose that reduces the number of monthly migraine hours experienced by the individual by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine hours experienced by the individual by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that reduces the number of monthly migraine hours experienced by the individual by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that reduces the number of monthly migraine hours experienced by the individual by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine hours experienced by the individual by at least 75% following administration of a Botulinum toxin disclosed herein as compared to a pre-treatment baseline and/or a control individual.

In some embodiments, methods and uses disclosed herein administer a Botulinum toxin disclosed herein to the individual at a dose sufficient to reduce the number of migraine attacks experienced by an individual over the course of a month as compared to the number of monthly migraine attacks experienced by the individual prior to administration of the Botulinum toxin disclosed herein (i.e. individual's pre-treatment baseline) and/or the number of monthly migraine attacks experienced by another matched individual not receiving the Botulinum toxin disclosed herein (i.e., a control individual). A migraine attack refers to an episode of any migraine as defined herein. A migraine attack that is interrupted by sleep or temporarily remits and then recurs within 48 hours is generally considered to be a single attack. Similarly, a migraine attack that is successfully treated with acute migraine-specific medication but relapses within 48 hours is also considered to be a single attack.

In aspects of these embodiments, methods and uses disclosed herein administer a Botulinum toxin disclosed herein to the individual at a dose that reduces the number of monthly migraine attacks experienced by the individual by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine attacks experienced by the individual by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that reduces the number of monthly migraine attacks experienced by the individual by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that reduces the number of monthly migraine attacks experienced by the individual by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine attacks experienced by the individual by at least 75% following administration of a Botulinum toxin disclosed herein as compared to a pre-treatment baseline and/or a control individual.

In some embodiments, methods and uses disclosed herein administer a Botulinum toxin disclosed herein to the individual at a dose sufficient to reduce the number of migraine-specific medication use days experienced by an individual over the course of a month as compared to the number of monthly migraine-specific medication use days experienced by the individual prior to administration of the Botulinum toxin disclosed herein (i.e. individual's pre-treatment baseline) and/or the number of monthly migraine-specific medication use days experienced by another matched individual not receiving the Botulinum toxin disclosed herein (i.e., a control individual). A migraine-specific medication use day refers to any calendar day during which an individual took a medication that is specific for migraine. Migraine-specific medications include, but are not limited to, triptans (e.g., almotriptan, frovatriptan, rizatriptan, sumatriptan, naratriptan, eletriptan, and zolmitriptan), ergotamines (e.g., dihydroergotamine and ergotamine with caffeine), non-steroidal anti-inflammatory drugs (e.g., acetylsalicylic acid, ibuprofen, naproxen, indomethacin, and diclofenac), CGRP inhibitors, (e.g., erenumab-aooe, fremanezumab, galcanezumab-gnlm and eptinezumab-jjmr) and opioids (e.g., codeine, morphine, hydrocodone, fentanyl, meperidine, and oxycodone). In some embodiments, a dose sufficient to reduce the number of monthly migraine-specific medication use days in an individual in need thereof is about 195 units to about 240 units.

In aspects of these embodiments, methods and uses disclosed herein administer a Botulinum toxin disclosed herein to the individual at a dose that reduces the number of monthly migraine-specific medication use days experienced by the individual by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine-specific medication use days experienced by the individual by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that reduces the number of monthly migraine-specific medication use days experienced by the individual by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that reduces the number of monthly migraine-specific medication use days experienced by the individual by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine-specific medication use days experienced by the individual by at least 75% following administration of a Botulinum toxin disclosed herein as compared to a pre-treatment baseline and/or a control individual.

In some embodiments, methods and uses disclosed herein administer a Botulinum toxin disclosed herein to the individual at a dose sufficient to reduce the number of days of physical impairment due to a migraine disorder experienced by an individual over the course of a month as compared to the number of monthly migraine-specific physical impairment days experienced by the individual prior to administration of the Botulinum toxin disclosed herein (i.e. individual's pre-treatment baseline) and/or the number of monthly migraine-specific physical impairment days experienced by another matched individual not receiving the Botulinum toxin disclosed herein (i.e., a control individual). In some embodiments, methods and uses disclosed herein administer a Botulinum toxin disclosed herein to the individual at a dose sufficient to reduce the number of days of functional impairment due to a migraine disorder experienced by an individual over the course of a month as compared to the number of monthly migraine-specific functional impairment days prior to administration of the Botulinum toxin disclosed herein (i.e. pre-treatment baseline) and/or the number of monthly migraine-specific functional impairment days experienced by an individual not receiving the Botulinum toxin disclosed herein (i.e., control individual). Physical and/or functional impairment due to a migraine disorder on everyday activities of an individual can be assessed using a number of validated questionnaires as described herein. In some embodiments, a dose sufficient to reduce the number of monthly migraine-specific physical and/or functional impairment days in an individual in need thereof is about 195 units to about 240 units.

In aspects of these embodiments, methods and uses disclosed herein administer a Botulinum toxin disclosed herein to the individual at a dose that reduces the number of monthly migraine-specific physical and/or functional impairment days experienced by the individual by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine-specific physical and/or functional impairment days experienced by the individual by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that reduces the number of monthly migraine-specific physical and/or functional impairment days experienced by the individual by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that reduces the number of monthly migraine-specific physical and/or functional impairment days experienced by the individual by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that reduces the number of monthly migraine-specific physical and/or functional impairment days experienced by the individual by at least 75% following administration of a Botulinum toxin disclosed herein as compared to a pre-treatment baseline and/or a control individual.

In some embodiments, methods and uses disclosed herein administer a Botulinum toxin disclosed herein to the individual at a dose sufficient to improve a physical impairment or quality-of-life impact score reported by an individual on an impact questionnaire as compared to the a physical impairment or quality-of-life impact score reported by an individual prior to administration of the Botulinum toxin disclosed herein (i.e. individual's pre-treatment baseline) and/or the a physical impairment or quality-of-life impact score reported by another matched individual not receiving the Botulinum toxin disclosed herein (i.e., a control individual). A migraine disorder often impacts the quality of life of patients and prevent them from engaging in leisure and everyday activities as well as cause a loss of productivity in an individual's job. These effects can be assessed using validated impact questionnaires, such as, e.g., a Headache Impact Test-6 (HIT-6), a Patient Health Questionnaire (PHQ-9), a Generalized Anxiety Disorder 7 (GAD-7), a PTSD Checklist, a DSM-5 (PCL-5), a modified Migraine Disability Assessment Questionnaire (MIDAS), a Migraine-Specific Quality of Life Questionnaire (MSQ), a Migraine Functional Impact Questionnaire (MFIQ), a Migraine Physical Function Impact Diary (MPFID), or any combination thereof. Thus, the disclosed methods and uses improve one or more aspects of an individual's quality of life and/or reduce the impact of migraines on one or more aspects of an individual's physical, social, or emotional function as assessed by one or more of these impact questionnaires. In some embodiments, a dose sufficient to improve a physical impairment or quality-of-life impact score reported in an individual in need thereof is about 195 units to about 240 units.

HIT-6 is a 6-item self-administered questionnaire that screens for and measures the severity of a migraine disorder. The HIT-6 consists of six items: pain, social functioning, role functioning, vitality, cognitive functioning, and psychological distress. Individuals answer each of the six related questions using one of the following five responses: "never", "rarely", "sometimes", "very often", or "always". These responses are summed to produce a total HIT-6 score that ranges from 36 to 78, where a higher score indicates a greater impact of headache on the daily life of the respondent. In some embodiments, methods and uses disclosed herein administer a Botulinum toxin disclosed herein to the individual at a dose sufficient to improve an individual's HIT-6 score (i.e. reduces the reduces the frequency or severity of migraine) as compared to the individual's HIT-6 score prior to administration of the Botulinum toxin disclosed herein (i.e. pre-treatment baseline) and/or the HIT-6 score of an individual not receiving the Botulinum toxin disclosed herein (i.e., a control individual).

PHQ-9 is a 9-item self-administered questionnaire that screens for and measures the severity of depression. The scale uses a normative system of scoring that assigns a value to the number of days an individual was anxious over a two-week period. Individuals respond to each items using a 4-point scale: 0=not at all; 1=several days; 2=more than half the days; and 3=nearly every day. The scores are calculated as the sum of the item responses with 0-4=minimal or no depression; 5-9=mild depression; 10-14=moderate depression; 15-19=moderately severe depression (warrants active treatment with psychotherapy, medications, or combination); and 20-27=severe depression. In some embodiments, methods and uses disclosed herein administer a Botulinum toxin disclosed herein to the individual at a dose sufficient to improve an individual's PHQ-9 score (i.e. reduces the reduces the frequency or severity of depression) as compared to the individual's PHQ-9 score prior to administration of the Botulinum toxin disclosed herein (i.e. pre-treatment baseline) and/or the PHQ-9 score of an individual not receiving the Botulinum toxin disclosed herein (i.e., a control individual).

GAD-7 is a 7-item self-administered questionnaire that screens for and measures the severity of a generalized anxiety disorder. The scale uses a normative system of scoring that assigns a value to the number of days an individual was anxious over a two-week period. Individuals respond to each items using a 4-point scale: 0=not at all; 1=several days; 2=more than half the days; and 3=nearly every day. The scores are calculated as the sum of the item responses with 0-4=minimal anxiety; 5-9=mild anxiety; 10-14=moderate anxiety; and 15-21=severe anxiety. In some embodiments, methods and uses disclosed herein administer a Botulinum toxin disclosed herein to the individual at a dose sufficient to improve an individual's GAD-7 score (i.e. reduces the reduces the frequency or severity of anxiety) as compared to the individual's GAD-7 score prior to administration of the Botulinum toxin disclosed herein (i.e. pre-treatment baseline) and/or the GAD-7 score of an individual not receiving the Botulinum toxin disclosed herein (i.e., a control individual).

PCL-5 is a 20-item self-administered questionnaire that assesses the 20 DSM-5 symptoms of PTSD. The PCL-5 can be scored in different ways. A total symptom severity score (range—0-80) can be obtained by summing the scores for each of the 20 items. DSM-5 symptom cluster severity scores can be obtained by summing the scores for the items within a given cluster, i.e., cluster B (items 1-5), cluster C (items 6-7), cluster D (items 8-14), and cluster E (items 15-20). A provisional PTSD diagnosis can be made by treating each item rated as 2="Moderately" or higher as a symptom endorsed, then following the DSM-5 diagnostic rule which requires at least: 1 B item (questions 1-5), 1 C item (questions 6-7), 2 D items (questions 8-14), 2 E items (questions 15-20). In some embodiments, methods and uses disclosed herein administer a Botulinum toxin disclosed herein to the individual at a dose sufficient to improve an individual's PCL-5 score (i.e. reduces the reduces the frequency or severity of PTSD) as compared to the individual's PCL-5 score prior to administration of the Botulinum toxin disclosed herein (i.e. pre-treatment baseline) and/or the PCL-5 score of an individual not receiving the Botulinum toxin disclosed herein (i.e., a control individual).

MIDAS is a 5-item self-administered questionnaire that sums the number of productive days lost over the past month in the workplace and the home. The MIDAS also assesses disability in family, social, and leisure activities. The MIDAS score is the sum of missed days due to a headache from paid work, housework, and non-work (family, social, leisure) activities; and days at paid work or housework where productivity was reduced by at least half. The score is categorized into 4 severity grades: Grade I=0-5 (defined as minimal or infrequent disability), Grade II=6-10 (mild or infrequent disability), Grade III=11-20 (moderate disability), and Grade IV=21 and over (severe disability). In some embodiments, methods and uses disclosed herein administer a Botulinum toxin disclosed herein to the individual at a dose sufficient to improve an individual's MIDAS score (i.e. reduces the reduces the frequency or severity of disability caused by migraine) as compared to the individual's MIDAS score prior to administration of the Botulinum toxin disclosed herein (i.e. pre-treatment baseline) and/or the MIDAS score of an individual not receiving the Botulinum toxin disclosed herein (i.e., a control individual).

The MSQ is a self-administered 14-item instrument measuring (i) how migraines limit an individual's daily social and work-related activities (role function-restrictive), (ii) how migraines prevent these activities (role function-preventive), and (iii) the emotions associated with an individual's migraines (emotional function). Individuals respond to items using a 6-point scale: "none of the time," "a little bit of the time," "some of the time," "a good bit of the time," "most of the time," and "all of the time," which are assigned scores of 1 to 6, respectively. Raw dimension scores are computed as a sum of item responses and rescaled from a 0 to 100 scale such that higher scores indicate better quality of life. In some embodiments, methods and uses disclosed herein administer a Botulinum toxin disclosed herein to the individual at a dose sufficient to improve an individual's MSQ score (i.e. improves the quality of the individual's life) as compared to the individual's MSQ score prior to administration of the Botulinum toxin disclosed herein (i.e. individual's pre-treatment baseline) and/or the MSQ score of another matched individual not receiving the Botulinum toxin disclosed herein (i.e., a control individual).

The MFIQ is a self-administered 26-item instrument measuring the impact of migraine on broader functioning. Specifically, it measures the impact of an individual's migraines on physical functioning, usual activities, social functioning, and emotional functioning. Subjects respond to items using a 5-point scale assigned scores from 1 to 5, with 5 representing the greatest burden. The scores are calculated as the sum of the item responses and the sum is rescaled to a 0-100 scale, with higher scores representing greater burden. In some embodiments, methods and uses disclosed herein administer a Botulinum toxin disclosed herein to the individual at a dose sufficient to improve an individual's MFIQ score (i.e. reduces the impact of migraine on an individual's functioning) as compared to the individual's MFIQ score prior to administration of the Botulinum toxin disclosed herein (i.e. individual's pre-treatment baseline) and/or the MFIQ score of another matched individual not receiving the Botulinum toxin disclosed herein (i.e., a control individual).

The MPFID is a self-administered 13-item instrument measuring physical functioning. It assesses impact on everyday activities and physical impairment. Subjects respond to items using a 5-point scale, with difficulty items ranging from "Without any difficulty" to "Unable to do" and frequency items ranging from "None of the time" to "All of the time." These are assigned scores from 1 to 5, with 5 representing the greatest burden. Scores are calculated as the sum of the item responses and the sum is rescaled to a 0-100 scale, with higher scores representing greater impact of migraine (i.e., higher burden). In some embodiments, methods and uses disclosed herein administer a Botulinum toxin disclosed herein to the individual at a dose sufficient to improve an individual's MPFID score (i.e. reduces the impact of migraine on an individual's physical functioning or everyday activities) as compared to the individual's MPFID score prior to administration of the Botulinum toxin disclosed herein (i.e. individual's pre-treatment baseline) and/or the MPFID score of another matched individual not receiving the Botulinum toxin disclosed herein (i.e., a control individual).

In aspects of these embodiments, methods and uses disclosed herein administer a Botulinum toxin disclosed herein to the individual at a dose that improves a physical impairment or quality-of-life impact score reported by the individual using an impact questionnaire by, e.g., about 10%, about 15%, about 20%, about 25%, about 30%, about 35%, about 40%, about 45%, about 50%, about 55%, about 60%, about 65%, about 70%, about 75%, following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that improves a physical impairment or quality-of-life impact score reported by the individual using an impact questionnaire by, e.g., at least 25%, at least 50%, at least 75%, or at least 100%, following administration of a Botulinum toxin disclosed herein as compared to a pre-treatment baseline and/or a control individual. In yet other aspects of these embodiments, methods and uses disclosed herein administer a Botulinum toxin disclosed herein to the individual at a dose that improves a physical impairment or quality-of-life impact score reported by the individual using an impact questionnaire by, e.g., about 25% to about 50%, about 25% to about 75%, about 25% to about 100%, about 50% to about 75%, about 50% to about 100%, or about 75% to about 100%, following administration of a Botulinum toxin disclosed herein as compared to a pre-treatment baseline and/or a control individual. In still other aspects of these embodiments, methods and uses disclosed herein administer a Botulinum toxin disclosed herein to the individual at a dose that improves a physical impairment or quality-of-life impact score reported by the individual using an impact questionnaire by at least 50% following administration of a Botulinum toxin disclosed herein as compared to a pre-treatment baseline and/or a control individual. In other aspects of these embodiments, methods and uses disclosed herein administer a Botulinum toxin disclosed herein to the individual at a dose that improves a physical impairment or quality-of-life impact score reported by the individual using an impact questionnaire by at least 75% following administration of a Botulinum toxin disclosed herein as compared to a pre-treatment baseline and/or a control individual.

In some embodiments of the methods and uses, administration of a Botulinum toxin disclosed herein at the dosages described herein does not substantially cause an adverse side effect in an individual. In particular, administration of a Botulinum toxin disclosed herein at the dosages described herein does not substantially cause an adverse side effect associated with other migraine prophylactic treatments, including adverse side effects associated with anti-epileptics, beta-blockers, and anti-depressants and CGRP inhibitors . . . . In certain embodiments, the number and type of adverse side effects associated with administration of a Botulinum toxin disclosed herein is not statistically different than the number and type of adverse side effects associated with administration of placebo.

The present specification discloses, in part, a migraine disorder. The methods and uses disclosed herein are useful in treating multiple migraine types including chronic migraines, episodic migraine, migraines associated with traumatic brain injury, migraines associated with patients that have concurrent post-traumatic stress disorder, and migraines associated with whiplash. The methods and uses disclosed herein are useful in treating post-traumatic headache.

The methods and uses disclosed herein are useful in treating a migraine. A migraine is a primary headache disorder characterized by recurrent, moderate to severe headaches associated with autonomic symptoms. The severity of the pain, duration of the headache, and frequency of attacks are variable. Typically, the headaches affect one half of the head, are pulsating in nature, and last from a few hours to 3 days. A migraine lasting longer than 72 hours is termed status migrainosus. Associated symptoms may include nausea, vomiting, and sensitivity to light, sound, or smell. The pain is generally made worse by physical activity. About 15% to 30% of people affected have an aura, typically a short period of visual disturbance that signals that the headache will soon occur. Occasionally, an aura can occur with little or no headache following it and people who experience an aura also frequently have migraines without aura. There are four possible phases to a migraine, although not all the phases are necessarily experienced: 1) the prodrome, which occurs hours or days before the headache; 2) the aura, which immediately precedes the headache; 3) the pain phase, also known as headache phase; and 4) the postdrome, the effects experienced following the end of a migraine attack. Migraines are associated with major depression, bipolar disorder, anxiety disorders, and obsessive-compulsive disorder. These psychiatric disorders are approximately 2-5 times more common in people without aura, and 3-10 times more common in people with aura. The current American Headache Association definition of chronic migraine is when an individual with at least five lifetime attacks of migraine has 15 or more headache days per month and at least 8 of the headache days are migraine days. However, this definition (i.e. and number of migraine headache days) that define "chronic migraine" or "chronic posttraumatic migraine" may vary and change in frequency subject to any future change in its definition by the standards as set by national or international recognized organizations that determine that define the future description of the chronic migraine.

The methods and uses disclosed herein are useful in treating a migraine associated with post-traumatic brain injury (TBI). A TBI, also known as an intracranial injury, is damage to the brain resulting from external mechanical force, such as rapid acceleration or deceleration, impact, blast waves, or penetration by a projectile. TBI can be classified based on severity of the injury, anatomical features of the injury, or the mechanism (the causative forces). The Glasgow Coma Scale (GCS) is the most commonly used system for classifying TBI severity. This system grades an individual's level of consciousness on a scale of 3-15 based on verbal, motor, and eye-opening reactions to stimuli with a GCS of 13 or above being a mild TBI, 9-12 being a moderate TBI, and 8 or below being a severe TBI. Severity-related classification divides TBI into mild head injury, moderate head injury and severe head injury. Mechanism-related classification divides TBI to non-penetrating (also known as closed or blunt) head injury where the damage does not breach the cranium and the brain is not exposed to the outside environment and penetrating (also known as closed) head injury where the damage pierces the cranium to expose the brain to the outside environment. Non-limiting examples of a TBI include, without limitation, intracranial hemorrhage, intra-axial hemorrhage (including intraparenchymal hemorrhage and intraventricular hemorrhage), extra-axial hemorrhage (including subdural hematoma, epidural hematoma, subarachnoid hemorrhage), brain herniation, cerebral contusion, cerebral laceration, concussion (including post-concussion syndrome, second-impact syndrome, dementia pugilistica and chronic traumatic encephalopathy), diffuse axonal injury, abusive head trauma, and penetrating head injury. There is a high incidence of migraines in individual's who experienced a traumatic brain injury and a traumatic brain injury worsens migraines, in terms of frequency of onset and severity of pain and other symptoms.

The methods and uses disclosed herein are useful in treating a migraine associated with post-traumatic stress disorder (PTSD or PTS). PTSD can occur as a result of exposure to traumatic stressors that arouse feelings of intense fear, helplessness, and horror in an individual who previously was exposed to head trauma and subsequent symptoms of migraine headache. As a result of these stressors the individual's response characteristically involves emotionally re-experiencing the event, numbing of affect, and avoidance of stimuli, which are associated with the event, as well as increased arousal. Although PTSD is shown to have a high incidence and be highly prevalent as a sequela of Posttraumatic migraine, PTSD has also been shown to worsen migraines, in terms of frequency of onset and severity of pain and other symptoms. Similarly, this can lead to a downward spiraling "feedback loop" whereby the debilitating symptoms of migraine then worsens the symptoms associated with PTSD. If both combine to become severe enough, (also associated with opioid treatment) it can contribute to one of the known causes of suicide related deaths associated with PTSD.

The methods and uses disclosed herein are useful in treating a migraine associated with whiplash. Whiplash is a non-medical term describing a range of injuries to the neck caused by or related to a sudden distortion of the neck associated with extension, although the exact injury mechanisms remain unknown. "Cervical acceleration-deceleration" (CAD) describes the mechanism of the injury, while the term "whiplash associated disorders" (WAD) describes the injury sequelae and symptoms. Symptoms include, without limitation, pain and aching to the neck and back, referred pain to the shoulders, sensory disturbance (such as pins and needles) to the arms and legs, and headaches. Symptoms can appear directly after the injury, but often are not felt until days afterwards.

The methods and uses disclosed herein are useful in treating a post-traumatic headache. A post-traumatic headache requires that the headache start within one week of the trauma. If the headache persists for less than 3 months after this it is referred to as an acute post-traumatic headache. If the headache persists for longer than 3 months it is referred to as a chronic post-traumatic headache. These headaches are further sub-divided into mild, moderate or severe depending on the extent of the injury that caused the headache. A post-traumatic headache can be caused by, without limitation, a closed head injury, including blast injuries; an open head injury, with or without intra-parenchymal lesions such as hematomas and contusions, a post craniotomy with trauma secondary to surgical effects; a psychological trauma, such as depression, anxiety and post-traumatic stress disorder; and a whiplash injury as well as other soft tissue injuries around the head and neck area.

Aspects of the present specification may also be described by the following embodiments:

1. A method for treating a migraine disorder, the method comprising extramuscularly administering a Botulinum toxin to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual.

2. The method of embodiment 1, wherein the one or more areas the fronto-fascial layer includes a left frontal nerve cluster zone and a right frontal nerve cluster zone, the left frontal nerve cluster zone located in a left portion of the frontal head region and the right frontal nerve cluster zone located in a right portion of the frontal head region.

3. The method of embodiment 2, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 to about 1 cm laterally right from the midline of the forehead, and the second right frontal vertical boundary being located in-line with a medial inferior edge of the right superior orbital ridge.

4. The method of any one of embodiments 1-3, wherein the one of more areas the temporoparietal-fascial layer includes a left temporal nerve cluster zone and a right temporal nerve cluster zone, the left temporal nerve cluster zone located in a left temporal head region and the right temporal nerve cluster zone located in a right temporal head region.

5. The method of embodiment 4, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.

6. The method of any one of embodiments 1-5, wherein the one of more areas the occipito-fascial layer includes a left occipital nerve cluster zone and a right occipital nerve cluster zone, the left occipital nerve cluster zone located in a left portion of the occipital head region and the right occipital nerve cluster zone located in a right portion of the occipital head region.

7. The method of embodiment 6, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm laterally right from the external occipital crest and the second right occipital vertical boundary being positioned in line with a right mastoid process and a dorsal portion of a right superior temporal line.

8. The method of any one of embodiments 1-7, wherein the concentration of the Botulinum toxin is 5 units/100 µL.

9. The method of any one of embodiments 1-7, wherein the concentration of the Botulinum toxin is 5 units/200 µL.

10. The method of any one of embodiments 1-9, wherein 40 units to 60 units of the Botulinum toxin are administered to one or more sites within the fronto-fascial layer, wherein each of the one or more sites is administered 5 units of the Botulinum toxin.

11. The method of any one of embodiments 1-10, wherein 40 units to 70 units of the Botulinum toxin are administered to one or more sites within the temporoparietal-fascial layer, wherein each of the one or more sites is administered 5 units of the Botulinum toxin.

12. The method of any one of embodiments 1-10, wherein 60 units to 110 units of the Botulinum toxin are administered to one or more sites within the occipito-fascial layer, wherein each of the one or more sites is administered 5 units of the Botulinum toxin.

13. The method of any one of embodiments 2-12, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.

14. The method of any one of embodiments 4-13, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.

15. The method of any one of embodiments 6-14, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.

16. The method of any one of embodiments 1-15 further comprising extramuscularly administering a Botulinum toxin to one or more nerve exit points in the head and neck.

17. The method of embodiment 16, wherein the Botulinum toxin is extramuscularly administered to one or more nerve exit points of a Supraorbital nerve, a Supratrochlear nerve, or any combination thereof.

18. The method of embodiment 17, wherein the one or more nerve exit points of the Supraorbital nerve include the left and right Supraorbital foramen.

19. The method of embodiment 17 or 18, wherein the one or more nerve exit points of the Supratrochlear nerve include the left and right Supratrochlear foramen.

20. The method of any one of embodiments 16-19, wherein the Botulinum toxin is extramuscularly administered to a location along a medial branch of a Supertrochelar Nerve located subcutaneously above the central part of the procerus muscle.

21. The method of any one of embodiments 16-20, wherein the Botulinum toxin is extramuscularly administered to an exit location of the Greater Auricular nerve located subcutaneously above the posterior edge of the midpoint of the left Sternocleidomastoid muscle and to an exit location of the Greater Auricular nerve located subcutaneously above the posterior edge of the midpoint of the left Sternocleidomastoid muscle.

22. The method of embodiment 21 further comprising extramuscularly administered of the Botulinum toxin to a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.

23. The method of any one of embodiments 16-22, wherein each of the one or more nerve exit points is administered 5 units of the Botulinum toxin.

24. The method of any one of embodiments 16-23, wherein the concentration of the Botulinum toxin is 5 units/100 μL.

25. The method of any one of embodiments 16-23, wherein the concentration of the Botulinum toxin is 5 units/200 μL.

26. The method of any one of embodiments 1-25 further comprising extramuscularly administering a Botulinum toxin to one or more sites along a Supraclavicular nerve, a Cervical Nerve Plexus, or any combination thereof.

27. The method of embodiment 26, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.

28. The method of embodiment 26 or 27, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.

29. The method of any one of embodiments 26-28, wherein each of the one or more nerve exit points is administered 5 units of the Botulinum toxin.

30. The method of any one of embodiments 26-29, wherein the concentration of the Botulinum toxin is 5 units/100 μL.

31. The method of any one of embodiments 26-29, wherein the concentration of the Botulinum toxin is 5 units/200 μL.

32. The method of any one of embodiments 1-31 further comprising extramuscularly administering a Botulinum toxin to one or more sites of an epicranial aponeurosis.

33. The method of embodiment 32, wherein each of the one or more sites is administered 5 units of the Botulinum toxin.

34. The method of embodiment 32 or 33, wherein the concentration of the Botulinum toxin is 5 units/100 μL.

35. The method of embodiment 32 or 33, wherein the concentration of the Botulinum toxin is 5 units/200 μL.

36. The method of any one of embodiments 1-35 further comprising intramuscularly administering a Botulinum toxin to one or more locations within the left and right Splenius Capitus muscle, the left and right Masseter muscles, the left and right Trapezius muscles, or any combination thereof.

37. The method of embodiment 36, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.

38. The method of embodiment 36 or 37, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.

39. The method of any one of embodiments 35-38, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.

40. A method for treating a migraine disorder, the method comprising extramuscularly administering a Botulinum toxin to an individual in one of more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, and one or more areas of an occipito-fascial layer located in an occipital head region of the individual, the one of more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region.

41. The method of embodiment 40, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 cm to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 cm to about 1 cm laterally right from the midline of the forehead, and the second right frontal vertical boundary being located in-line with a medial inferior edge of the right superior orbital ridge.

42. The method of embodiment 40 or 41, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.

43. The method of any one of embodiments 40-42, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm to about 1 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm to about 1 cm laterally right from the external occipital crest and the second right occipital vertical boundary being positioned in line with a right mastoid process and a dorsal portion of a right superior temporal line.

44. The method of any one of embodiments 40-43, wherein the concentration of the Botulinum toxin is 5 units/100 μL.

45. The method of any one of embodiments 40-43, wherein the concentration of the Botulinum toxin is 5 units/200 μL.

46. The method of any one of embodiments 40-45, wherein 40 units to 60 units of the Botulinum toxin are administered to one or more sites within the fronto-fascial layer, wherein each of the one or more sites is administered 5 units of the Botulinum toxin.

47. The method of any one of embodiments 40-45, wherein 40 units to 70 units of the Botulinum toxin are administered to one or more sites within the temporo-parietal-fascial layer, wherein each of the one or more sites is administered 5 units of the Botulinum toxin.

48. The method of any one of embodiments 40-47, wherein 60 units to 110 units of the Botulinum toxin are administered to one or more sites within the occipito-fascial layer, wherein each of the one or more sites is administered 5 units of the Botulinum toxin.

49. The method of any one of embodiments 40-48, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.

50. The method of any one of embodiments 40-49, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.

51. The method of any one of embodiments 40-50, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.

52. The method of any one of embodiments 40-51 further comprising extramuscularly administering a Botulinum toxin to one or more nerve exit points in the head and neck.

53. The method of embodiment 52, wherein the Botulinum toxin is extramuscularly administered to one or more nerve exit points of a Supraorbital nerve, a Supratrochlear nerve, or any combination thereof.

54. The method of embodiment 53, wherein the one or more nerve exit points of the Supraorbital nerve include the left and right Supraorbital foramen.
55. The method of embodiment 53 or 54, wherein the one or more nerve exit points of the Supratrochlear nerve include the left and right Supratrochlear foramen.
56. The method of any one of embodiments 52-55, wherein the Botulinum toxin is extramuscularly administered to a location along a medial branch of a Supertrochelar Nerve located subcutaneously above the central part of the procerus muscle.
57. The method of any one of embodiments 52-56, wherein the Botulinum toxin is extramuscularly administered to an exit location of the Greater Auricular nerve located subcutaneously above the posterior edge of the midpoint of the left Sternocleidomastoid muscle and to an exit location of the Greater Auricular nerve located subcutaneously above the posterior edge of the midpoint of the left Sternocleidomastoid muscle.
58. The method of embodiment 57 further comprising extramuscularly administered of the Botulinum toxin to a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.
59. The method of any one of embodiments 52-58, wherein each of the one or more nerve exit points is administered 5 units of the Botulinum toxin.
60. The method of any one of embodiments 52-59, wherein the concentration of the Botulinum toxin is 5 units/100 µL.
61. The method of any one of embodiments 52-59, wherein the concentration of the Botulinum toxin is 5 units/200 µL.
62. The method of any one of embodiments 40-61 further comprising extramuscularly administering a Botulinum toxin to one or more sites along a Supraclavicular nerve, a Cervical Nerve Plexus, or any combination thereof.
63. The method of embodiment 62, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.
64. The method of embodiment 62 or 63, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.
65. The method of any one of embodiments 62-64, wherein each of the one or more nerve exit points is administered 5 units of the Botulinum toxin.
66. The method of any one of embodiments 62-65, wherein the concentration of the Botulinum toxin is 5 units/100 µL.
67. The method of any one of embodiments 62-65, wherein the concentration of the Botulinum toxin is 5 units/200 µL.
68. The method of any one of embodiments 40-67 further comprising extramuscularly administering a Botulinum toxin to one or more sites of an epicranial aponeurosis.
69. The method of embodiment 68, wherein each of the one or more sites is administered 5 units of the Botulinum toxin.
70. The method of embodiment 68 or 69, wherein the concentration of the Botulinum toxin is 5 units/100 µL.
71. The method of embodiment 68 or 69, wherein the concentration of the Botulinum toxin is 5 units/200 µL.
72. The method of any one of embodiments 40-71 further comprising intramuscularly administering a Botulinum toxin to one or more locations within the left and right Splenius Capitus muscle, the left and right Masseter muscles, the left and right Trapezius muscles, or any combination thereof.
73. The method of embodiment 72, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.
74. The method of embodiment 72 or 73, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.
75. The method of any one of embodiments 72-74, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.
76. A method for treating a migraine disorder, the method comprising extramuscularly administering a Botulinum toxin to an individual in one or more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, one or more areas of an occipito-fascial layer located in an occipital head region of the individual, the one of more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region, and one or more areas in the head and neck, the one or more areas in the head and neck including one or more nerve exit points of a Supraorbital nerve and Supratrochlear nerve, an exit location of a Greater Auricular nerve above a Sternocleidomastoid muscle, or any combination thereof.

77. The method of embodiment 76, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 cm to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 cm to about 1 cm laterally right from the midline of the forehead, and the second right frontal vertical boundary being located in-line with a medial inferior edge of the right superior orbital ridge.

78. The method of embodiment 76 or 77, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.

79. The method of any one of embodiments 76-78, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm to about 1 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm to about 1 cm laterally right from the external occipital crest and the second right occipital vertical boundary being positioned in line with a right mastoid process and a dorsal portion of a right superior temporal line.

80. The method of any one of embodiments 76-79, wherein the one or more nerve exit points of the Supraorbital nerve include the left and right Supraorbital foramen.

81. The method of any one of embodiments 76-80, wherein the one or more nerve exit points of the Supratrochlear nerve include the left and right Supratrochlear foramen.

82. The method of any one of embodiments 76-81, wherein the one or more subcutaneous locations along the medial branch of a Supratrochlear nerve is above the central part of the procerus muscle.

83. The method of any one of embodiments 76-82, wherein the one or more exit locations of the Greater Auricular nerve include an exit location of the Greater Auricular nerve above the posterior edge of the midpoint of the left Sternocleidomastoid muscle and an exit location of the Greater Auricular nerve above the posterior edge of the midpoint of the left Sternocleidomastoid muscle.

84. The method of embodiment 83, wherein the one or more subcutaneous locations along the Greater Auricular nerve include a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.

85. The method of any one of embodiments 76-84, wherein the concentration of the Botulinum toxin is 5 units/100 µL.

86. The method of any one of embodiments 76-84, wherein the concentration of the Botulinum toxin is 5 units/200 μL.
87. The method of any one of embodiments 76-86, wherein 40 units to 60 units of the Botulinum toxin are administered to one or more sites within the fronto-fascial layer, wherein each of the one or more sites is administered 5 units of the Botulinum toxin.
88. The method of any one of embodiments 76-87, wherein 40 units to 70 units of the Botulinum toxin are administered to one or more sites within the temporo-parietal-fascial layer, wherein each of the one or more sites is administered 5 units of the Botulinum toxin.
89. The method of any one of embodiments 76-88, wherein 60 units to 110 units of the Botulinum toxin are administered to one or more sites within the occipito-fascial layer, wherein each of the one or more sites is administered 5 units of the Botulinum toxin.
90. The method of any one of embodiments 76-89, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.
91. The method of any one of embodiments 76-90, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.
92. The method of any one of embodiments 76-91, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.
93. The method of any one of embodiments 76-92, wherein the one or more areas in the head and neck further comprise one or more sites along a Cervical Nerve Plexus, a Supraclavicular nerve, or any combination thereof.
94. The method of embodiment 93, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.
95. The method of embodiment 93 or 94, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.
96. The method of any one of embodiments 93-95, wherein each of the one or more sites is administered 5 units of the Botulinum toxin.
97. The method of any one of embodiments 93-96, wherein the concentration of the Botulinum toxin is 5 units/100 μL.
98. The method of any one of embodiments 93-96, wherein the concentration of the Botulinum toxin is 5 units/200 μL.
99. The method of any one of embodiments 76-98 further comprising extramuscularly administering a Botulinum toxin to one or more sites of an epicranial aponeurosis.
100. The method of embodiment 99, wherein each of the one or more sites is administered 5 units of the Botulinum toxin.
101. The method of embodiment 99 or 100, wherein the concentration of the Botulinum toxin is 5 units/100 μL.
102. The method of embodiment 99 or 100, wherein the concentration of the Botulinum toxin is 5 units/200 μL.
103. The method of any one of embodiments 76-102 further comprising intramuscularly administering a Botulinum toxin to one or more locations within the left and right Splenius Capitus muscle, the left and right Masseter muscles, the left and right Trapezius muscles, or any combination thereof.
104. The method of embodiment 103, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.
105. The method of embodiment 103 or 104, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.
106. The method of any one of embodiments 102-105, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.
107. The method of any one of embodiments 102-106, wherein each of the one or more nerve exit points is administered 5 units of the Botulinum toxin.
108. The method of any one of embodiments 102-107, wherein the concentration of the Botulinum toxin is 5 units/100 μL.
109. The method of any one of embodiments 102-107, wherein the concentration of the Botulinum toxin is 5 units/200 μL.
110. A method for treating a migraine disorder, the method comprising extramuscularly administering a Botulinum toxin to an individual in one of more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin, one or more areas of an occipito-fascial layer located in an occipital head region of the individual, the one of more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin, and one or more areas in the head and neck, the one or more areas in the head and neck including a nerve exit point of the left Supraorbital nerve located at the left Supraorbital foramen, a nerve exit point of the right Supraorbital nerve located at the right Supraorbital foramen, a nerve exit point of the left Supratrochlear nerve located at the left Supratrochlear foramen, a nerve exit point of the right Supratrochlear nerve located at the right Supratrochlear foramen, an exit location of the Greater Auricular nerve located subcutaneously above the posterior edge of the midpoint of the left Sternocleidomastoid muscle, an exit location of the Greater Auricular nerve located subcutaneously above the posterior edge of the midpoint of the left Sternocleidomastoid muscle, wherein each of the nerve exit points is administered 5 units of the Botulinum toxin.

111. The method of embodiment 110, wherein the one or more areas in the head and neck further include a location along the Greater Auricular nerve located subcutaneously above a position midway between the mastoid process and a line drawn at the midpoint of the left Sternocleidomastoid muscle and a location along the Greater Auricular nerve located subcutaneously above a position midway between the mastoid process and a line drawn at the midpoint of the right Sternocleidomastoid muscle.

112. The method of embodiment 110 or 111, wherein the one or more areas in the head and neck further comprise a site along a left side of a Cervical Nerve Plexus located subcutaneously above a soft triangular depression cranially to a superior edge of a left Splenius Capitus muscle, a site along a right side of a Cervical Nerve Plexus located subcutaneously above a soft triangular depression cranially to a superior edge of a right Splenius Capitus muscle, a site along a left Supraclavicular nerve located subcutaneously at an apical ridge of a superior portion of a left Trapezius muscle, and a site along a right Supraclavicular nerve located subcutaneously at an apical ridge of a superior portion of a right Trapezius muscle, wherein each of the nerve exit points is administered 5 units of the Botulinum toxin.

113. The method of any one of embodiments 110-112 further comprising extramuscularly administering a Botulinum toxin to a nerve exit point of a left side of a Cervical Nerve Plexus located subcutaneously above a cervical vertebrae insertion of a left Longissimus capitis muscle, a nerve exit point of a left side of a Cervical Nerve Plexus located subcutaneously above a cervical vertebrae insertion of a left Longissimus cervicis muscle, a nerve exit point of a right side of a Cervical Nerve Plexus located subcutaneously above a cervical vertebrae insertion of a right Longissimus capitis muscle, a nerve exit point of a right side of a Cervical Nerve Plexus located subcutaneously above a cervical vertebrae insertion of a right Longissimus cervicis muscle, wherein each of the nerve exit points is administered 5 units of the Botulinum toxin.

114. The method of any one of embodiments 110-113 further comprising extramuscularly administering a Botulinum toxin to one or more sites of an epicranial aponeurosis, wherein each of the one or more sites is administered 5 units of the Botulinum toxin.

115. The method of any one of embodiments 110-114 further comprising intramuscularly administering a Botulinum toxin to one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle, one or more intramuscular sites located above a left masseter muscle near an angle of a left mandibular ramus or one or more intramuscular sites located above a right masseter muscle near an angle of a right mandibular ramus, one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle, wherein each of the nerve exit points is administered 5 units of the Botulinum toxin.

116. The method of any one of embodiments 110-115, wherein the concentration of the Botulinum toxin is 5 units/100 μL.

117. The method of any one of embodiments 110-115, wherein the concentration of the Botulinum toxin is 5 units/200 μL.

118. The method of any one of embodiments 1-117, wherein the total amount of the Botulinum toxin administered is 195 units to 240 units.

119. The method of any one of embodiments 1-118, wherein the Botulinum toxin is a Botulinum A toxin a Botulinum B toxin, a Botulinum C1 toxin, a Botulinum C2 toxin, a Botulinum E toxin, a Botulinum F toxin, a Botulinum G toxin or any combination thereof.

120. The method of any one of embodiments 1-119, wherein the Botulinum toxin is a Botulinum A toxin.

121. The method of embodiment 120, wherein the Botulinum A toxin is a OnabotulinumtoxinA.

122. The method of any one of embodiments 1-121, wherein the migraine disorder is a chronic migraine, a migraine associated with traumatic brain injury, a migraine associated with a post-traumatic stress disorder, or a migraine associated with whiplash.

123. The method of any one of embodiments 1-122, wherein the migraine disorder is a chronic migraine associated with post-traumatic stress disorder.

Aspects of the present specification may also be described by the following embodiments:

1. A Botulinum toxin for use in treating a migraine disorder, use of a Botulinum toxin in treating a migraine disorder, or use of a Botulinum toxin in the manufacture of a medicament for treating a migraine disorder, wherein the Botulinum toxin is extramuscularly administered to an individual in one of more areas of a fronto-fascial layer located in a frontal head region of the individual, one of more areas of a temporoparietal-fascial layer located in a temporal head region of the individual, and one or more areas of an occipito-fascial layer located in an occipital head region of the individual.
2. The Botulinum toxin or use of embodiment 1, wherein the one or more areas the fronto-fascial layer includes a left frontal nerve cluster zone and a right frontal nerve cluster zone, the left frontal nerve cluster zone located in a left portion of the frontal head region and the right frontal nerve cluster zone located in a right portion of the frontal head region.
3. The Botulinum toxin or use of embodiment 2, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 to about 1 cm laterally right from the midline of the forehead, and the second right frontal vertical boundary being located in-line with a medial inferior edge of the right superior orbital ridge.
4. The Botulinum toxin or use of any one of embodiments 1-3, wherein the one of more areas the temporoparietal-fascial layer includes a left temporal nerve cluster zone and a right temporal nerve cluster zone, the left temporal nerve cluster zone located in a left temporal head region and the right temporal nerve cluster zone located in a right temporal head region.
5. The Botulinum toxin or use of embodiment 4, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.
6. The Botulinum toxin or use of any one of embodiments 1-5, wherein the one of more areas the occipito-fascial layer includes a left occipital nerve cluster zone and a right occipital nerve cluster zone, the left occipital nerve cluster zone located in a left portion of the occipital head region and the right occipital nerve cluster zone located in a right portion of the occipital head region.
7. The Botulinum toxin or use of embodiment 6, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm laterally right from the external occipital crest and the second right occipital vertical boundary being positioned in line with a right mastoid process and a dorsal portion of a right superior temporal line.

8. The Botulinum toxin or use of any one of embodiments 1-7, wherein the concentration of the Botulinum toxin is 5 units/100 μL.

9. The Botulinum toxin or use of any one of embodiments 1-7, wherein the concentration of the Botulinum toxin is 5 units/200 μL.
10. The Botulinum toxin or use of any one of embodiments 1-9, wherein 40 units to 60 units of the Botulinum toxin are administered to one or more sites within the fronto-fascial layer, wherein each of the one or more sites is administered 5 units of the Botulinum toxin.
11. The Botulinum toxin or use of any one of embodiments 1-10, wherein 40 units to 70 units of the Botulinum toxin are administered to one or more sites within the temporoparietal-fascial layer, wherein each of the one or more sites is administered 5 units of the Botulinum toxin.
12. The Botulinum toxin or use of any one of embodiments 1-10, wherein 60 units to 110 units of the Botulinum toxin are administered to one or more sites within the occipito-fascial layer, wherein each of the one or more sites is administered 5 units of the Botulinum toxin.
13. The Botulinum toxin or use of any one of embodiments 2-12, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.
14. The Botulinum toxin or use of any one of embodiments 4-13, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.
15. The Botulinum toxin or use of any one of embodiments 6-14, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.
16. The Botulinum toxin or use of any one of embodiments 1-15 further comprising extramuscularly administering a Botulinum toxin to one or more nerve exit points in the head and neck.
17. The Botulinum toxin or use of embodiment 16, wherein the Botulinum toxin is extramuscularly administered to one or more nerve exit points of a Supraorbital nerve, a Supratrochlear nerve, or any combination thereof.
18. The Botulinum toxin or use of embodiment 17, wherein the one or more nerve exit points of the Supraorbital nerve include the left and right Supraorbital foramen.
19. The Botulinum toxin or use of embodiment 17 or 18, wherein the one or more nerve exit points of the Supratrochlear nerve include the left and right Supratrochlear foramen.
20. The Botulinum toxin or use of any one of embodiments 16-19, wherein the Botulinum toxin is extramuscularly administered to a location along a medial branch of a Supertrochelar Nerve located subcutaneously above the central part of the procerus muscle.
21. The Botulinum toxin or use of any one of embodiments 16-20, wherein the Botulinum toxin is extramuscularly administered to an exit location of the Greater Auricular nerve located subcutaneously above the posterior edge of the midpoint of the left Sternocleidomastoid muscle and to an exit location of the Greater Auricular nerve located subcutaneously above the posterior edge of the midpoint of the left Sternocleidomastoid muscle.
22. The Botulinum toxin or use of embodiment 21 further comprising extramuscularly administered of the Botulinum toxin to a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.
23. The Botulinum toxin or use of any one of embodiments 16-22, wherein each of the one or more nerve exit points is administered 5 units of the Botulinum toxin.
24. The Botulinum toxin or use of any one of embodiments 16-23, wherein the concentration of the Botulinum toxin is 5 units/100 μL.
25. The Botulinum toxin or use of any one of embodiments 16-23, wherein the concentration of the Botulinum toxin is 5 units/200 μL.
26. The Botulinum toxin or use of any one of embodiments 1-25 further comprising extramuscularly administering a Botulinum toxin to one or more sites along a Supraclavicular nerve, a Cervical Nerve Plexus, or any combination thereof.
27. The Botulinum toxin or use of embodiment 26, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.
28. The Botulinum toxin or use of embodiment 26 or 27, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.
29. The Botulinum toxin or use of any one of embodiments 26-28, wherein each of the one or more nerve exit points is administered 5 units of the Botulinum toxin.

30. The Botulinum toxin or use of any one of embodiments 26-29, wherein the concentration of the Botulinum toxin is 5 units/100 µL.
31. The Botulinum toxin or use of any one of embodiments 26-29, wherein the concentration of the Botulinum toxin is 5 units/200 μL.
32. The Botulinum toxin or use of any one of embodiments 1-31 further comprising extramuscularly administering a Botulinum toxin to one or more sites of an epicranial aponeurosis.
33. The Botulinum toxin or use of embodiment 32, wherein each of the one or more sites is administered 5 units of the Botulinum toxin.
34. The Botulinum toxin or use of embodiment 32 or 33, wherein the concentration of the Botulinum toxin is 5 units/100 μL.
35. The Botulinum toxin or use of embodiment 32 or 33, wherein the concentration of the Botulinum toxin is 5 units/200 μL.
36. The Botulinum toxin or use of any one of embodiments 1-35 further comprising intramuscularly administering a Botulinum toxin to one or more locations within the left and right Splenius Capitus muscle, the left and right Masseter muscles, the left and right Trapezius muscles, or any combination thereof.
37. The Botulinum toxin or use of embodiment 36, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.
38. The Botulinum toxin or use of embodiment 36 or 37, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.
39. The Botulinum toxin or use of any one of embodiments 35-38, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.
40. A Botulinum toxin for use in treating a migraine disorder, use of a Botulinum toxin in treating a migraine disorder, or use of a Botulinum toxin in the manufacture of a medicament for treating a migraine disorder, wherein the Botulinum toxin is extramuscularly administered to an individual in one of more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, and one or more areas of an occipito-fascial layer located in an occipital head region of the individual, the one of more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region.
41. The Botulinum toxin or use of embodiment 40, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 cm to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 cm to about 1 cm laterally right from the midline of the forehead, and the second right frontal vertical boundary being located in-line with a medial inferior edge of the right superior orbital ridge.
42. The Botulinum toxin or use of embodiment 40 or 41, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.

43. The Botulinum toxin or use of any one of embodiments 40-42, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm to about 1 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm to about 1 cm laterally right from the external occipital crest and the second right occipital vertical boundary being positioned in line with a right mastoid process and a dorsal portion of a right superior temporal line.

44. The Botulinum toxin or use of any one of embodiments 40-43, wherein the concentration of the Botulinum toxin is 5 units/100 µL.

45. The Botulinum toxin or use of any one of embodiments 40-43, wherein the concentration of the Botulinum toxin is 5 units/200 µL.

46. The Botulinum toxin or use of any one of embodiments 40-45, wherein 40 units to 60 units of the Botulinum toxin are administered to one or more sites within the fronto-fascial layer, wherein each of the one or more sites is administered 5 units of the Botulinum toxin.

47. The Botulinum toxin or use of any one of embodiments 40-45, wherein 40 units to 70 units of the Botulinum toxin are administered to one or more sites within the temporoparietal-fascial layer, wherein each of the one or more sites is administered 5 units of the Botulinum toxin.

48. The Botulinum toxin or use of any one of embodiments 40-47, wherein 60 units to 110 units of the Botulinum toxin are administered to one or more sites within the occipito-fascial layer, wherein each of the one or more sites is administered 5 units of the Botulinum toxin.

49. The Botulinum toxin or use of any one of embodiments 40-48, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.

50. The Botulinum toxin or use of any one of embodiments 40-49, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.

51. The Botulinum toxin or use of any one of embodiments 40-50, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.

52. The Botulinum toxin or use of any one of embodiments 40-51 further comprising extramuscularly administering a Botulinum toxin to one or more nerve exit points in the head and neck.

53. The Botulinum toxin or use of embodiment 52, wherein the Botulinum toxin is extramuscularly administered to one or more nerve exit points of a Supraorbital nerve, a Supratrochlear nerve, or any combination thereof.

54. The Botulinum toxin or use of embodiment 53, wherein the one or more nerve exit points of the Supraorbital nerve include the left and right Supraorbital foramen.

55. The Botulinum toxin or use of embodiment 53 or 54, wherein the one or more nerve exit points of the Supratrochlear nerve include the left and right Supratrochlear foramen.

56. The Botulinum toxin or use of any one of embodiments 52-55, wherein the Botulinum toxin is extramuscularly administered to a location along a medial branch of a Supertrochelar Nerve located subcutaneously above the central part of the procerus muscle.

57. The Botulinum toxin or use of any one of embodiments 52-56, wherein the Botulinum toxin is extramuscularly administered to an exit location of the Greater Auricular nerve located subcutaneously above the posterior edge of the midpoint of the left Sternocleidomastoid muscle and to an exit location of the Greater Auricular nerve located subcutaneously above the posterior edge of the midpoint of the left Sternocleidomastoid muscle.

58. The Botulinum toxin or use of embodiment 57 further comprising extramuscularly administered of the Botulinum toxin to a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.

59. The Botulinum toxin or use of any one of embodiments 52-58, wherein each of the one or more nerve exit points is administered 5 units of the Botulinum toxin.

60. The Botulinum toxin or use of any one of embodiments 52-59, wherein the concentration of the Botulinum toxin is 5 units/100 μL.

61. The Botulinum toxin or use of any one of embodiments 52-59, wherein the concentration of the Botulinum toxin is 5 units/200 μL.

62. The Botulinum toxin or use of any one of embodiments 40-61 further comprising extramuscularly administering a Botulinum toxin to one or more sites along a Supraclavicular nerve, a Cervical Nerve Plexus, or any combination thereof.

63. The Botulinum toxin or use of embodiment 62, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.

64. The Botulinum toxin or use of embodiment 62 or 63, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.

65. The Botulinum toxin or use of any one of embodiments 62-64, wherein each of the one or more nerve exit points is administered 5 units of the Botulinum toxin.

66. The Botulinum toxin or use of any one of embodiments 62-65, wherein the concentration of the Botulinum toxin is 5 units/100 μL.

67. The Botulinum toxin or use of any one of embodiments 62-65, wherein the concentration of the Botulinum toxin is 5 units/200 μL.

68. The Botulinum toxin or use of any one of embodiments 40-67 further comprising extramuscularly administering a Botulinum toxin to one or more sites of an epicranial aponeurosis.

69. The Botulinum toxin or use of embodiment 68, wherein each of the one or more sites is administered 5 units of the Botulinum toxin.

70. The Botulinum toxin or use of embodiment 68 or 69, wherein the concentration of the Botulinum toxin is 5 units/100 μL.

71. The Botulinum toxin or use of embodiment 68 or 69, wherein the concentration of the Botulinum toxin is 5 units/200 μL.

72. The Botulinum toxin or use of any one of embodiments 40-71 further comprising intramuscularly administering a Botulinum toxin to one or more locations within the left and right Splenius Capitus muscle, the left and right Masseter muscles, the left and right Trapezius muscles, or any combination thereof.

73. The Botulinum toxin or use of embodiment 72, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.

74. The Botulinum toxin or use of embodiment 72 or 73, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.

75. The Botulinum toxin or use of any one of embodiments 72-74, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.

76. A Botulinum toxin for use in treating a migraine disorder, use of a Botulinum toxin in treating a migraine disorder, or use of a Botulinum toxin in the manufacture of a medicament for treating a migraine disorder, wherein the Botulinum toxin is extramuscularly administering to an individual in one of more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, one or more areas of an occipito-fascial layer located in an occipital head region of the individual, the one of more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region, and one or more areas in the head and neck, the one or more areas in the head and neck including one or more nerve exit points of a Supraorbital nerve and Supratrochlear nerve, an exit location of a Greater Auricular nerve above a Sternocleidomastoid muscle, or any combination thereof.

77. The Botulinum toxin or use of embodiment 76, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 cm to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 cm to about 1 cm laterally right from the midline of the forehead, and the second right frontal vertical boundary being located in-line with a medial inferior edge of the right superior orbital ridge.

78. The Botulinum toxin or use of embodiment 76 or 77, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crux and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crux and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus.

79. The Botulinum toxin or use of any one of embodiments 76-78, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm to about 1 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm to about 1 cm laterally right from the external occipital crest and the second right occipital vertical boundary being positioned in line with a right mastoid process and a dorsal portion of a right superior temporal line.

80. The Botulinum toxin or use of any one of embodiments 76-79, wherein the one or more nerve exit points of the Supraorbital nerve include the left and right Supraorbital foramen.

81. The Botulinum toxin or use of any one of embodiments 76-80, wherein the one or more nerve exit points of the Supratrochlear nerve include the left and right Supratrochlear foramen.

82. The Botulinum toxin or use of any one of embodiments 76-81, wherein the one or more subcutaneous locations along the medial branch of a Supratrochlear nerve is above the central part of the procerus muscle.

83. The Botulinum toxin or use of any one of embodiments 76-82, wherein the one or more exit locations of the Greater Auricular nerve include an exit location of the Greater Auricular nerve above the posterior edge of the midpoint of the left Sternocleidomastoid muscle and an exit location of the Greater Auricular nerve above the posterior edge of the midpoint of the left Sternocleidomastoid muscle.

84. The Botulinum toxin or use of embodiment 83, wherein the one or more subcutaneous locations along the Greater Auricular nerve include a location along the Greater Auricular nerve located subcutaneously above a position midway between the mastoid process and a line drawn at the midpoint of the left Sternocleidomastoid muscle and to a location along the Greater Auricular nerve located subcutaneously above a position midway between the mastoid process and a line drawn at the midpoint of the right Sternocleidomastoid muscle.

85. The Botulinum toxin or use of any one of embodiments 76-84, wherein the concentration of the Botulinum toxin is 5 units/100 μL. 86. The Botulinum toxin or use of any one of embodiments 76-84, wherein the concentration of the Botulinum toxin is 5 units/200 μL.

87. The Botulinum toxin or use of any one of embodiments 76-86, wherein 40 units to 60 units of the Botulinum toxin are administered to one or more sites within the fronto-fascial layer, wherein each of the one or more sites is administered 5 units of the Botulinum toxin.

88. The Botulinum toxin or use of any one of embodiments 76-87, wherein 40 units to 70 units of the Botulinum toxin are administered to one or more sites within the temporoparietal-fascial layer, wherein each of the one or more sites is administered 5 units of the Botulinum toxin.

89. The Botulinum toxin or use of any one of embodiments 76-88, wherein 60 units to 110 units of the Botulinum toxin are administered to one or more sites within the occipito-fascial layer, wherein each of the one or more sites is administered 5 units of the Botulinum toxin.

90. The Botulinum toxin or use of any one of embodiments 76-89, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin.

91. The Botulinum toxin or use of any one of embodiments 76-90, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin.

92. The Botulinum toxin or use of any one of embodiments 76-91, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin.

93. The Botulinum toxin or use of any one of embodiments 76-92, wherein the one or more areas in the head and neck further comprise one or more sites along a Cervical Nerve Plexus, a Supraclavicular nerve, or any combination thereof.

94. The Botulinum toxin or use of embodiment 93, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.

95. The Botulinum toxin or use of embodiment 93 or 94, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.

96. The Botulinum toxin or use of any one of embodiments 93-95, wherein each of the one or more sites is administered 5 units of the Botulinum toxin.

97. The Botulinum toxin or use of any one of embodiments 93-96, wherein the concentration of the Botulinum toxin is 5 units/100 μL.

98. The Botulinum toxin or use of any one of embodiments 93-96, wherein the concentration of the Botulinum toxin is 5 units/200 μL.

99. The Botulinum toxin or use of any one of embodiments 76-98 further comprising extramuscularly administering a Botulinum toxin to one or more sites of an epicranial aponeurosis.

100. The Botulinum toxin or use of embodiment 99, wherein each of the one or more sites is administered 5 units of the Botulinum toxin.

101. The Botulinum toxin or use of embodiment 99 or 100, wherein the concentration of the Botulinum toxin is 5 units/100 μL.

102. The Botulinum toxin or use of embodiment 99 or 100, wherein the concentration of the Botulinum toxin is 5 units/200 μL.

103. The Botulinum toxin or use of any one of embodiments 76-102 further comprising intramuscularly administering a Botulinum toxin to one or more locations within the left and right Splenius Capitus muscle, the left and right Masseter muscles, the left and right Trapezius muscles, or any combination thereof.

104. The Botulinum toxin or use of embodiment 103, wherein the one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle.

105. The Botulinum toxin or use of embodiment 103 or 104, wherein the one or more locations of the left and right Mandibular nerve include one or more intramuscular sites located above a left masseter muscle near an angle of a left mandibular ramus or one or more intramuscular sites located above a right masseter muscle near an angle of a right mandibular ramus.

106. The Botulinum toxin or use of any one of embodiments 102-105, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.

107. The Botulinum toxin or use of any one of embodiments 102-106, wherein each of the one or more nerve exit points is administered 5 units of the Botulinum toxin.

108. The Botulinum toxin or use of any one of embodiments 102-107, wherein the concentration of the Botulinum toxin is 5 units/100 μL.

109. The Botulinum toxin or use of any one of embodiments 102-107, wherein the concentration of the Botulinum toxin is 5 units/200 μL.

110. A Botulinum toxin for use in treating a migraine disorder, use of a Botulinum toxin in treating a migraine disorder, or use of a Botulinum toxin in the manufacture of a medicament for treating a migraine disorder, wherein the Botulinum toxin is extramuscularly administered to an individual in one of more areas of a fronto-fascial layer located in a frontal head region of the individual, the one or more areas the fronto-fascial layer including a left frontal nerve cluster zone and a right frontal nerve cluster zone, the left frontal nerve cluster zone located in a left portion of the frontal head region and the right frontal nerve cluster zone located in a right portion of the frontal head region, wherein 20 units to 30 units of the Botulinum toxin are administered to one or more sites within the left frontal nerve cluster zone and 20 units to 30 units of the Botulinum toxin are administered to one or more sites within the right frontal nerve cluster zone, wherein each of the one or more sites is administered 5 units of the Botulinum toxin, one of more areas of a temporoparietal-fascial layer located in a temporal head region of the individual, the one of more areas the temporoparietal-fascial layer including a left temporal nerve cluster zone and a right temporal nerve cluster zone, the left temporal nerve cluster zone located in a left temporal head region and the right temporal nerve cluster zone located in a right temporal head region, wherein 20 units to 35 units of the Botulinum toxin are administered to one or more sites within the left temporal nerve cluster zone and 20 units to 35 units of the Botulinum toxin are administered to one or more sites within the right temporal nerve cluster zone, wherein each of the one or more sites is administered 5 units of the Botulinum toxin, one or more areas of an occipito-fascial layer located in an occipital head region of the individual, the one or more areas the occipito-fascial layer including a left occipital nerve cluster zone and a right occipital nerve cluster zone, the left occipital nerve cluster zone located in a left portion of the occipital head region and the right occipital nerve cluster zone located in a right portion of the occipital head region, wherein 30 units to 55 units of the Botulinum toxin are administered to one or more sites within the left occipital nerve cluster zone and 30 units to 55 units of the Botulinum toxin are administered to one or more sites within the right occipital nerve cluster zone, wherein each of the one or more sites is administered 5 units of the Botulinum toxin, and one or more areas in the head and neck, the one or more areas in the head and neck including a nerve exit point of the left Supraorbital nerve located at the left Supraorbital foramen, a nerve exit point of the right Supraorbital nerve located at the right Supraorbital foramen, a nerve exit point of the left Supratrochlear nerve located at the left Supratrochlear foramen, a nerve exit point of the right Supratrochlear nerve located at the right Supratrochlear foramen, an exit location of the Greater Auricular nerve located subcutaneously above the posterior edge of the midpoint of the left Sternocleidomastoid muscle, an exit location of the Greater Auricular nerve located subcutaneously above the posterior edge of the midpoint of the left Sternocleidomastoid muscle, wherein each of the nerve exit points is administered 5 units of the Botulinum toxin.

111. The Botulinum toxin or use of embodiment 110, wherein the one or more areas in the head and neck further include a location along the Greater Auricular nerve located subcutaneously above a position midway between the mastoid process and a line drawn at the midpoint of the left Sternocleidomastoid muscle and a location along the Greater Auricular nerve located subcutaneously above a position midway between the mastoid process and a line drawn at the midpoint of the right Sternocleidomastoid muscle.

112. The Botulinum toxin or use of embodiment 110 or 111, wherein the one or more areas in the head and neck further comprise a site along a left side of a Cervical Nerve Plexus located subcutaneously above a soft triangular depression cranially to a superior edge of a left Splenius Capitus muscle, a site along a right side of a Cervical Nerve Plexus located subcutaneously above a soft triangular depression cranially to a superior edge of a right Splenius Capitus muscle, a site along a left Supraclavicular nerve located subcutaneously at an apical ridge of a superior portion of a left Trapezius muscle, and a site along a right Supraclavicular nerve located subcutaneously at an apical ridge of a superior portion of a right Trapezius muscle, wherein each of the nerve exit points is administered 5 units of the Botulinum toxin.

113. The Botulinum toxin or use of any one of embodiments 110-112 further comprising extramuscularly administering a Botulinum toxin to a nerve exit point of a left side of a Cervical Nerve Plexus located subcutaneously above a cervical vertebrae insertion of a left Longissimus capitis muscle, a nerve exit point of a left side of a Cervical Nerve Plexus located subcutaneously above a cervical vertebrae insertion of a left Longissimus cervicis muscle, a nerve exit point of a right side of a Cervical Nerve Plexus located subcutaneously above a cervical vertebrae insertion of a right Longissimus capitis muscle, a nerve exit point of a right side of a Cervical Nerve Plexus located subcutaneously above a cervical vertebrae insertion of a right Longissimus cervicis muscle, wherein each of the nerve exit points is administered 5 units of the Botulinum toxin.

114. The Botulinum toxin or use of any one of embodiments 110-113 further comprising extramuscularly administering a Botulinum toxin to one or more sites of an epicranial aponeurosis, wherein each of the one or more sites is administered 5 units of the Botulinum toxin.

115. The Botulinum toxin or use of any one of embodiments 110-114 further comprising intramuscularly administering a Botulinum toxin to one or more locations of the left and right Splenius Capitus muscles include an intramuscular site located above a soft triangular depression cranially to a superior edge of a left Splenius Capitus muscle or an intramuscular site located above a soft triangular depression cranially to a superior edge of a right Splenius Capitus muscle, one or more intramuscular sites located above a left masseter muscle near an angle of a left mandibular ramus or one or more intramuscular sites located above a right masseter muscle near an angle of a right mandibular ramus, one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle, wherein each of the nerve exit points is administered 5 units of the Botulinum toxin.

116. The Botulinum toxin or use of any one of embodiments 110-115, wherein the concentration of the Botulinum toxin is 5 units/100 µL.

117. The Botulinum toxin or use of any one of embodiments 110-115, wherein the concentration of the Botulinum toxin is 5 units/200 µL.

118. The Botulinum toxin or use of any one of embodiments 1-117, wherein the total amount of the Botulinum toxin administered is 195 units to 240 units.

119. The Botulinum toxin or use of any one of embodiments 1-118, wherein the Botulinum toxin is a Botulinum A toxin a Botulinum B toxin, a Botulinum C1 toxin, a Botulinum C2 toxin, a Botulinum E toxin, a Botulinum F toxin, a Botulinum G toxin or any combination thereof.

120. The Botulinum toxin or use of any one of embodiments 1-119, wherein the Botulinum toxin is a Botulinum A toxin.

121. The Botulinum toxin or use of embodiment 120, wherein the Botulinum A toxin is a OnabotulinumtoxinA.

122. The Botulinum toxin or use of any one of embodiments 1-121, wherein the migraine disorder is a chronic migraine, a migraine associated with traumatic brain injury, a migraine associated with a post-traumatic stress disorder, or a migraine associated with whiplash.

123. The Botulinum toxin or use of any one of embodiments 1-122, wherein the migraine disorder is a chronic migraine associated with post-traumatic stress disorder.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

This example describes a method disclosed herein which encompasses up to 39 administration sites with each site being injected with 5 units/200 µL of a Botulinum toxin A. As shown in Table 2, in one embodiment, 195 units of a Botulinum toxin A are administered to 39 fixed administration sites. A 32-gauge needle is used to reduce the rapid rate of injection around the orbital and frontal areas (Sites 4-6) and facilitate the slow delivery of toxin and reduce the likelihood of eyelid ptosis, while a 30-gauge needle is used over the other sites of the head and neck (Sites 1-3 and A). In an alternative embodiment, each of the 39 administration sites is injected with 5 units/100 µL of a Botulinum toxin A.

In an alternative embodiment, 155 units of a Botulinum toxin A are administered to 31 fixed administration sites (Sites 1-6 in Table 2) while 40 units of a Botulinum toxin A are optionally administered to 8 additional administration sites (Sites 7 and A) with each site being injected with 5 units/200 µL of a Botulinum toxin A. A 32-gauge needle is used to reduce the rapid rate of injection around the orbital and frontal areas (Sites 4-6) and facilitate the slow delivery of toxin and reduce the likelihood of eyelid ptosis, while a 30-gauge needle is used over the other sites of the head and neck (Sites 1-3, 7 and A). In an alternative embodiment, each of the 39 administration sites is injected with 5 units/ 100 µL of a Botulinum toxin A.

Example 2

This example describes a method disclosed herein which encompasses up to 46 administration sites with each site being injected with 5 units/200 µL of a Botulinum toxin A. As shown in Table 3 and 4, in one embodiment, 185 units of a Botulinum toxin A are administered to 37 fixed administration sites (Sites 1-7, with Site 7 being injected 1 site/side, 7a) while 40-45 units of a Botulinum toxin A are administered to 8-9 additional administration sites (Sites A-E). A 32-gauge needle is used to reduce the rapid rate of injection around the orbital and frontal areas (Sites 4-6) and facilitate the slow delivery of toxin and reduce the likelihood of eyelid ptosis, while a 30-gauge needle is used over the other sites of the head and neck (Sites 1-3, 7a, and A-E). In an alternative embodiment, each of the 45-46 administration sites is injected with 5 units/100 µL of a Botulinum toxin A.

TABLE 2

Extramuscular Sites of Method Using a Botulinum Toxin A[1]

| Site No. | Site Location | Targeted Nerve | Site Distribution | Site Total | Total Dose (Units) |
|---|---|---|---|---|---|
| 1 | Fronto-Fascial Layer | Supraorbital and Supratrochlear Nerves | 3 sites/side | 6 | 30 |
| 2 | Temporoparietal-Fascial Layer | Auriculotemporal Nerve Supraorbital Nerve | 4 sites/side | 8 | 40 |
| 3 | Occipito-Fascial Layer | Postauricular Nerve and Greater and Lesser Occipital Nerves | 6 sites/side | 12 | 60 |
| 4 | Nerve Exit Point at Supratrochlear Foramen | Supratrochlear Nerve | 1 site/side | 2 | 10 |
| 5 | Nerve Exit Point at Supraorbital Foramen | Supraorbital Nerve | 1 site/side | 2 | 10 |
| 6 | Superficial to Procerus Muscle | Medial branches of Supratrochlear Nerve | 1 | 1 | 5 |
| 7 | Superficial to Sternoclidomastoid Muscle | Greater Auricular Nerve | 1 sites/side | 2 | 10 |
| A | Superficial to Trapezius Muscle | Supraclavicular Nerve | 3 sites/side | 6 | 30 |

[1]A total dose of 195 units of a Botulinum toxin is administered.

TABLE 3

Extramuscular Sites of Method Using a Botulinum Toxin A[1]

| Site No. | Site Location | Targeted Nerve | Site Distribution | Site Total | Total Dose (Units) |
|---|---|---|---|---|---|
| 1 | Fronto-Fascial Layer | Supraorbital and Supratrochlear Nerves | 3 sites/side | 6 | 30 |
| 2 | Temporoparietal-Fascial Layer | Auriculotemporal Nerve & Supraorbital Nerve | 4 sites/side | 8 | 40 |

TABLE 3-continued

Extramuscular Sites of Method Using a Botulinum Toxin A[1]

| Site No. | Site Location | Targeted Nerve | Site Distribution | Site Total | Total Dose (Units) |
|---|---|---|---|---|---|
| 3 | Occipito-Fascial Layer | Postauricular Nerve and Greater and Lesser Occipital Nerves | 8 sites/side | 16 | 80 |
| 4 | Nerve Exit Point at Supratrochlear Foramen | Supratrochlear Nerve | 1 site/side | 2 | 10 |
| 5 | Nerve Exit Point at Supraorbital Foramen | Supraorbital Nerve | 1 site/side | 2 | 10 |
| 6 | Superficial to Procerus Muscle | Medial Branches of the Supratrochlear Nerve | 1 | 1 | 5 |
| 7a, 7b | Superficial to Sternocleidomastoid Muscle | Greater Auricular Nerve & Cervical Nerve Plexus | 1-2 sites/side | 2-4 | 10-20 |
| A-E | Optional Additional Sites | See Table 4 | See Table 4 | See Table 4 | 40-45 |

[1]A total dose of 235-240 units of a Botulinum toxin is administered; 185-195 units of a Botulinum toxin are administered to fix sites, while the remaining 40-45 units of a Botulinum toxin are optionally administered to additional sites.

TABLE 4

Optional Additional Administration Sites of Method Using a Botulinum Toxin A

| Site No. | Site Location | Targeted Nerve | Site Distribution | Site Total | Total Dose (Units) |
|---|---|---|---|---|---|
| 1-7 | Fix Sites No. 1-7 | See Table 3 | 1 to 1-4 sites/side | 1-8 | 5-40 |
| A | Superficial to Trapezius Muscle | Supraclavicular Nerve | 2-3 sites/side | 4-6 | 20-30 |
| B | Cervical Paraspinal Muscle | Cervical Nerve Plexus | 1-2 sites/side | 2-4 | 10-20 |
| C | Epicranial Aponeurosis | Branches from the Supraorbital, Supratrochlear, greater & lesser Occipital and Auriculotemporal Nerve & Greater Auricular Nerves | 2-4 sites/side | 4-8 | 20-40 |
| D | Splenius Capitus Muscle | Cervical Nerve Plexus | 1 sites/side | 2 | 10 |
| E | Masseter Muscle | Mandibular Nerve | 1-2 sites/side | 2-4 | 10-20 |
| A | Trapezius Muscle | Supraclavicular Nerve | 2-3 sites/side | 4-6 | 20-30 |

In an alternative embodiment, 195 units of a Botulinum toxin A are administered to 39 fixed administration sites (Sites 1-7 in Table 3, with Site 7 being injected 2 sites/side, 7a and 7b) while 40-45 units of a Botulinum toxin A are administered to 8-9 additional administration sites (Sites A-E) with each site being injected with 5 units/200 μL of a Botulinum toxin A. A 32-gauge needle is used to reduce the rapid rate of injection around the orbital and frontal areas (Sites 4-6) and facilitate the slow delivery of toxin and reduce the likelihood of eyelid ptosis, while a 30-gauge needle is used over the other sites of the head and neck (Sites 1-2, 7a, 7b, and A-E). In an alternative embodiment, each of the 47-48 administration sites is injected with 5 units/100 μL of a Botulinum toxin A.

Example 3

An open-label, non-randomized, clinical study is to be conducted in order to evaluate the safety and efficacy of a Botulinum Toxin A therapy for the treatment of persistent post-traumatic headaches with migraine features attributed to mild traumatic injury to the head and/or whiplash (as defined in ICHD-3 5.2.2 & 5.4) with and/or without PTSD symptoms. During the initial phase, from thirty-sixty subjects, ages 18 to 65 years, will be recruited who experience persistent post traumatic headache with migraine features attributed to mild traumatic brain injury and with or without mild or moderate PTSD symptoms. The study duration is expected to last up to 18 months (less than 40 weeks for each individual subject).

The study will be divided into a 4-week Baseline Period and a 36-week Treatment Period. During the 4-week Baseline Period, each subject will be evaluated by a PTSD screener will complete PQH 9 and PCL-5 instruments in order to determine eligibility and collect baseline data that will serve as comparative controls for the study. Eligible subjects will then receive three treatment cycles on 12-week intervals a Botulinum Toxin A therapy according to one of the administration protocols as described in Examples 1 and 2. During the 36-week Treatment Period, each subject will complete PHQ 9, GAD 7, HIT-6 instruments at Week 0, 12, 24 and 36 and complete a PCL-5 instrument at Week 36. Since this is a treatment study for chronic posttraumatic migraine headache, based on measurements over periods of months, this treatment cycle may be repeated 1-2 times depending on the N used in the initial proof of concept study and data that will be collected during and at the end of a 72 week period of time.

The primary objective of this study is to determine the efficacy and safety of a Botulinum Toxin A therapy following the paradigm described herein for the treatment of Persistent Post-Traumatic Headaches with Migraine features attributed to mild traumatic injury to the head or attributed to whiplash with and/or without PTSD symptoms. As such, the primary endpoints include 1) assessing the safety and tolerability of a Botulinum Toxin A therapy for the treatment of mild persistent post-traumatic headache with migraine features as assessed by history and AEs; and 2) assessing the change from the 4-week Baseline Period in the mean number of migraine and probable migraine days measured over a 28-day period ending at Week 18 and Week 30 of the 36-week Treatment Period.

The clinical study will assess the effect of the associated symptoms of PTS or PTSD as a consequence of the symptoms of chronic posttraumatic headache and as a consequence of the events related to chronic posttraumatic migraine headache.

The secondary objectives include 1) to assess whether subjects treated with a Botulinum Toxin A therapy will have a decrease in the frequency of migraines; 2) to assess whether subjects treated with a Botulinum Toxin A therapy will have a decrease in the frequency of headaches. As such, the secondary endpoints include 1) assessing the change from the 4-week Baseline Period in the mean number of moderate to severe headache days measured over a 28-day period ending at Week 18 and Week 30 of the 36-week Treatment Period; 2) assessing the change from the 4-week Baseline Period in the mean number of migraine or probable migraine free days measured over a 28-day period ending at Week 18 and Week 30 of the 36-week Treatment Period; and 3) assessing the change from the 4-week Baseline Period in the mean number of headache free days measured over a 28-day period ending at Week 18 and Week 30 of the 36-week Treatment Period.

The exploratory objectives include to assess whether subjects treated with a Botulinum Toxin A therapy will have a change in any one or more of the scores on the HIT-6, PHQ 9, GAD 7 and PCL-5. As such, the exploratory endpoints include 1) assessing the change from the 4-week Baseline Period in the severity category of the PHQ 9 score measured over a 28-day period ending at Week 18 and Week 30 of the 36-week Treatment Period, and 24; 2) assessing the change from the 4-week Baseline Period in the severity category of the GAD 7 score measured over a 28-day period ending at Week 18 and Week 30 of the 36-week Treatment Period; 3) assessing the change from the 4-week Baseline Period in the severity category of the HIT-6 score measured over a 28-day period ending at Week 18 and Week 30 of the 36-week Treatment Period; 4) assessing the change from the 4-week Baseline Period in the severity category of the PCL-5 score measured at Week 36 of the 36-week Treatment Period; 5) assessing the change from the 4-week Baseline Period in the use of acute headache medications over a 28-day period ending at Week 18 and Week 30 of the 36-week Treatment Period; and 6) assessing the percentage of subjects with a reduction of at least 50% in the average number of headache days over a 28-day period ending at Week 18 and Week 30 of the 36-week Treatment Period when compared to the 4-week Baseline Period.

The clinical study will show that the methods and uses disclosed herein resulted in significant improvement in the treatment of individuals suffering from persistent post-traumatic headaches with migraine features attributed to mild traumatic injury to the head or attributed to whiplash with and/or without PTSD symptoms.

Example 4

This example presents fourteen case studies demonstrating the effectiveness of the zonal and targeted methods and uses disclosed herein.

Case Study 1. A 43-year-old female with a 20-year long history or chronic migraine headaches. A positive migraine history of grandmother, brother aunt and uncle. The patient was treated by headache experts for many years using Imitrex, and other migraine medications with partial relief. Migraine headaches worsened after an automobile accident associated with head injury and a fractured jaw and then progressed to persistent chronic posttraumatic headaches with migraine symptoms which worsened over time. These headaches were then associated with symptoms of Posttraumatic stress disorder including anxiety depression, sleep disorders and difficulty in concentration. Headache frequency worsened with an increase to 4-5 migraine headaches per week with each one lasting at least 24 hours along with worsening of associated symptoms of vertigo, nausea, vomiting, photophobia and phonophobia. Pain distribution included areas behind the eye, concentrated above the right eye within the lateral frontal or forehead areas, temporal areas and back of the head in lateral occipital areas and neck over the sternomastoid and jaw in the region of the masseter muscles. The patient also had associated back pain due to the related trauma. The patient initially received OnabotulinumtoxinA injections for her headaches by several doctors and neurologists using the standard PREEMPT (Phase 3 Research Evaluating Migraine Prophylaxis) intramuscular injection site protocol, but over time with diminishing results. The symptoms of persistent posttraumatic chronic migraine headache and symptoms of Posttraumatic stress disorder (PTSD) worsened despite recurring treatments. The last PREEMPT treatment protocol was administered 5 years prior to the new treatment paradigm being used. The Zonal injection technique protocol was utilized with a dilution of both 4-cc/100 units and 2-cc/100 units. Injections included a 2-cc/100 dilution of OnabotulinumA for the medial supraorbital and supratrochlear nerves, and frontal cluster zone area over the right and left forehead. A 4-cc/100 units dilution was then used to inject the right and left temporal cluster zone and 8 sites per side over the occipital and lateral occipital areas within the aponeurotic fascia targeting the occipital cluster zone of intermingling nerve endings of the occipital and postauricular nerves. The target areas for injection of the greater auricular and mandibular nerves were directed at their exit points of the sternomastoid and masseter muscles. One injection was directed to the posterior aspect border and mid-aspect of the sternomastoid muscle to treat the greater auricular nerve and then two injection sites are directed at the masseter muscle to treat the mandibular nerve. The total initial dose for treatment targeting the cluster zones I-III and specific pain zones in the manner described was increased to 245 units versus the less than 155 units previously administered via the PREEMPT protocol. The patient was followed for 3 months post treatment with what was described by the patient as a "miracle" treatment with a complete "change of life" results. Headache frequency decreased by 70% with at least an 80% reduction in pain. Symptoms such as anxiety, sleep disorders (reduction of nightmares with sleep pattern improvement) and lack of concentration associated with posttraumatic stress disorder (PTSD) abated with the concomitant reduction in migraine attacks. The patient is now followed for a period of 4 years with the dose remaining steady at 195 units to 245 units per treatment with an increasing and sustained duration of action of between 4 to 6 months. Treatment protocols have been standardized to concentrate the injection points over the 3 cluster zones and areas over nerve exit points over the neck muscles, and including the sternomastoid, masseter and then adding 1 injection site of 5 units (2 cc/100 units) into the splenius capitus muscles, bilaterally.

Case Study 2. A 45-year-old female patient has a history of having sustained facial injuries in 1996. Following nasal surgery, the patient had been symptom free from problems in breathing secondary to the nasal injury. The patient had an early history of headaches diagnosed with migrainous features as a teenager. The patient was treated with adequate control of the migraines until the patient was involved in an automobile accident in 2003. Subsequent to the accident which included whiplash, the patient developed daily headaches with neck pain and episodes of severe posttraumatic chronic migraine headaches which became superimposed on the daily headaches occurring 2-3 times per week and lasting up to 24 hours or more. Severity registered at least 9/10 rating. The migrainous episodes included head pain (primarily left hemi-crania), neck, and lower jaw pain, accompanied by aura, severe nausea and occasional vomiting. After initial treatments including Imitrex, Maxalt, pain relievers and other migraine therapies, OnabotulinumtoxinA was administered several years later. The initial treatment included the standardized 31 injection sites including the trapezius muscles with a dilution of 2-cc/100 units and a total dosage of less than 150 units. Initially, the Botulinum toxin treatments were successful in lessening the frequency and severity of the migraine headaches. The PREEMPT paradigm treatments continued for at least 5 years with a response to a generalized treatment paradigm as well as a gradual increased duration of action from the treatment. Treatment regimen was then supplemented by Maxalt by her neurologist. The headache symptoms were controlled until a 2nd posttraumatic equestrian event occurred in 2010 for which the patient was hospitalized. The migraine headaches post trauma severely worsened with recurrence of nausea, vomiting, vertigo, photophobia and severe neck pain. Post trauma, the patient eventually developed symptoms of Post-Traumatic Stress Disorder such as moodiness, depression, difficulty in concentration, irregular sleep patterns and nightmares. PREEMPT OnabotulinumtoxinA treatment was initiated but with only partial results. Patient was lost to follow up after pregnancies. During pregnancy the headaches were improved. Subsequently the patient was seen in 2018 with recurrence and worsening of the migraine headaches. Frequency was at 3 times/week with each episode lasting more than 24 hours. The symptoms did not respond to systemic migraine treatments including recently administered CGRP/Mab (Calcitonin Gene Related Peptide/Monoclonal Antibody) inhibitor drugs. The patient was then also treated by her neurologist with standard PREEMPT protocol of Onabotulinum toxin A without significant response. She was then treated in 2018 with current Zonal high dose protocol as described. A combination of 1-cc, 2-cc and 4-cc dilution was used to treat the areas of pain that were described and injection sites targeting the 3 cluster zone areas of the head. The injections were concentrated within these 3 cluster zone areas and the neck pain was treated with injections as described over the sternomastoid muscle, the cervical neck muscles as well as the splenius capitus muscles in three treatments over a 9-month period with a total dose ranging from 195 units to 245 units. The patient responded with at least an 80% reduction in frequency and intensity of pain. The duration of benefit from the enhanced injection paradigm has increased to almost 6 months. Sleep patterns, anxiety and mood swings were notably improved.

Case Study 3. A 43-year-old woman has a history of migraines dating back to her teens. She has had a gradual progression of her headache frequency as she has gotten older. She presents with daily headache mainly in the occipital and temporal regions. She has associated nausea and photophobia. The pain can be throbbing and worsened by movement. She has significant vertigo associated with her headaches. On examination she has left occipital scalp allodynia. Her diagnosis is Chronic Migraine with Vestibular Migraine. She is injected with OnabotulinumtoxinA following the PREEMPT protocol of injection sites with 31 sites in fixed locations. She also gets the standard follow the pain site injections in the occipitalis and temporalis areas. She has two cycles of treatment 12 weeks apart. When she returns for her third treatment, she notes overall improvement: but she has ongoing pain above and behind the left ear and mid lateral occipital area. She also notes that at 10 weeks post-injection her headache frequency starts to increase back to her original baseline of headaches. The new Zonal injection protocol is used to increase efficacy and duration. She returns for her fourth treatment cycle and notes overall headache control for the full 3 months of the cycle. In addition, she notes that she no longer has scalp allodynia and her vertigo has completely resolved as well.

Case Study 4. A 24-year-old Olympic Gymnast has Chronic Migraine. Her headaches are triggered by exercise and stress. She is treated with OnabotulinumtoxinA using the PREEMPT injection protocol as she cannot use any of the standard oral preventive migraine medications that might make her tired or interfere with her coordination or physical conditioning. Two weeks following this treatment she notes neck weakness and neck pain, which diminish her ability to perform at a high level. The Zonal injection protocol (excluding neck muscles) is used to reduce head pain while reducing side effects of injecting neck muscles. This results in headache control without any side-effects such as fatigue, poor concentration, neck weakness or neck pain.

Case Study 5. A 55-year-old female patient has been suffering from a lifelong history of migraine headaches. Over the course of 15 years, the patient was treated with standard doses of migraine medications including Imitrex. Complications of systemic migraine drugs and pain relievers prevented adequate control of the migraine symptoms. OnabotulinumtoxinA treatment was also initiated 15 years ago using the standard protocols including 31 intramuscular injection sites. However, subsequently, over the past 5 years, the patient began having resistance to the therapy with increasing frequency and intensity of the chronic migraine. Having had a rear end collision with having sustained a whiplash injury, the standard doses of OnabotulinumtoxinA treatment performed at her HMO were insufficient in containing the progression of the frequency and intensity of migraine headache pain. The patient began treatment with the protocol as described with a combination of dilution in the supraorbital areas of 2-cc/100 units and 4-cc/100 units were used to flood the cluster zone areas with OnabotulinumA. The areas of the neck were treated including the posterior aspect of the sternomastoid muscle and within the 3 cluster zone areas concentrating the injection sites within the temporal areas which were noted to have the sites of most pain. Initial treatment dose was 195 units, with improvement. Subsequent treatments yielded more effective relief of migrainous symptoms for a duration of 4 months at a dosing of 245 units according to the method described.

Case Study 6. A 65-year-old female has a history that includes a lifelong battle with headaches, diagnosed as chronic migraine headaches over 20 years ago. The patient did not respond to known migraine therapy as administered by her primary care physician and then referred to her neurologist over 15 years ago. The patient did respond to OnabotulinumtoxinA therapy over a period of 12 years with lower doses of less than 100 units per treatment session. Due to insurance reimbursement issues, the patient was treated with OnabotulinumtoxinA therapy in an HMO clinic with varied success with the loser doses. 3 years ago, the patient was riding her bicycle, fell and hit her head. Although wearing a helmet, this triggered an increased frequency of headaches, dizziness, nausea and photophobia. The only relief the patient sought was isolation to a dark room with no noise. The prior PREEMPT (Phase 3 Research Evaluating Migraine Prophylaxis) protocol of Botox was again attempted at the clinic, but with limited success. Other therapies for the diagnosis of persistent posttraumatic headache with migraine features were unsuccessful. After approval of medical reimbursement, the patient was treated with the enhanced Zonal protocol using OnabotulinumtoxinA for persistent chronic posttraumatic headache with migraine features. The distribution of pain was clearly located to the frontal, temporal and occipital cluster zones. Following the administration of 195 units of OnabotulinumtoxinA the patient reported a response of a reduction in pain intensity and a reduced frequency by 80%. Duration of action lasted 3.5 months vs. a reported 2-3-month period of partial relief from prior administration of lower dosages.

Case Study 7. A 73-year-old woman has had lifelong migraine which has proved difficult to control. On examination she has soft tissue excess due to aging over the orbital rim. Secondarily, her eyebrows are elevated due to frontalis compensation for her pseudo brow ptosis. OnabotulinumtoxinA injections using the PREEMPT injection sites helps to control her headaches but after each treatment she develops worsening of the eyebrow pseudoptosis. The Zonal injection protocol (staying above the lower ⅓rd of the frontalis muscle) is used to reduce this side effect while maintaining control of her migraine headaches.

Case Study 8. A 65-year-old male patient who had been treated for almost 15 years with positive results using the PREEMPT protocol for OnabotulinumtoxinA use. With less response over the last 4 to 5 years, the treatment paradigm was shifted with treatment directed more to localization of the headache pain. With more concentrated (1-cc/100 units; 2-cc/100 units; 3-cc/100 units and 4-cc/100 units) and more numerous injection sites which were directed over the target clusters areas of the lateral occipital areas (CL III), the patient noted significantly greater relief with the current protocol described. The number of injection sites were increased to 8 per side over the occipital and postauricular areas where the pain was most concentrated. There was significant benefit (greater than 50% reduction in pain and frequency of migraine symptoms) noted over the course of 15 months with 4 injection treatments. Treatments increased the number of injection sites and dose within the target area of occipital pain located within the Cluster Zone III area as described. Injection sites were localized to the distribution and overlapping of the occipital and postauricular nerve endings including the non-muscular related areas.

Case Study 9. A 56-year-old man with long standing migraine has received OnabotulinumtoxinA injections every 3 months for the last 3 years. The PREEMPT injection protocol had been routinely used. His headaches are well controlled for 8 weeks but returned at a high frequency in the last 4 weeks of the treatment cycle. His insurance company would not cover his repeat injections any sooner than 12 weeks from the treatment. As a result, in the last 4 weeks of the treatment cycle he is unable to work or engage in social activities due to disabling headaches. His headaches return predominantly and consistently in the post-auricular and posterior/lateral occipital areas. The Zonal injection protocol was then used which then increased efficacy and the duration of the positive effect. The Zonal protocol regimen was then used for the next 3 subsequent treatments 12 weeks apart. The patient returns to report complete headache control.

Case Study 10. A 46-year-old woman has refractory Chronic Migraine with comorbid anxiety, depression and PTSD. She has a history of childhood maltreatment. Her psychiatrist has optimized her anti-depressant treatment after many different medication trials, and despite this her patient health questionnaire (PHQ 9) index score shows ongoing depression of a moderate degree with a score of 10 by her primary medical care provider. She has no suicidal ideation, but suffers with insomnia, nightmares, intrusive thoughts, and headaches daily. As a result of the complexity of this case and the high degree of disability the provider decides to use the Zonal injection protocol for Onabotulinumtoxin A to try and get her condition under some level of control as quickly as possible. She is treated with the Zonal treatment protocol using 195 units. On follow up, here primary care physician notes that she now has improved headache control, which has helped to alleviate some of her anxiety, depression and other symptoms of PTSD. She has noted that even on days when she still has a headache her sleep pattern and mood are much improved.

Case Study 11. A 64-year-old female patient has an occupation in the medical industry. In her 20's, the patient experienced mild head trauma which exacerbated a lifelong history of migraines which progressed to chronic migraine. The areas of pain were primarily confined to the frontal and temporal areas. Symptoms included aura, mostly unilateral left sided pain over the frontal area (CZ I) and temporal area (CZ II). After receiving OnabotulinumtoxinA therapy for 10 years with control of headache pain with recommended PREEMPT dilution, over time the results of treatment resulted in a reduced response rate, with a shorter duration of action and lack of positive results. Two years prior, the patient's regimen was changed. A dilution of 1-cc/100 units was used to treat the supraorbital and supratrochlear areas of pain distribution and 2-cc/100 units with increased dosage to 40 units per area was used to treat the areas over the forehead area of Zone I and increased dosage of 40 units per area over the bitemporal areas were used with a total dosage of 195 units (increased from 150 units) for the frontal areas of the head. A 12 month follow up of 3 treatments resulted in at least a 50% improvement in reduction of head pain and reduction in frequency reducing the patient's reliance on supplemental migraine therapy from which she had severe side effects.

Case Study 12. A 33-year-old executive presents with refractory disabling Chronic Migraine. She has failed to respond to antidepressants, antiseizure, and blood pressure medications. She has seen a reduction of her headaches with OnabotulinumtoxinA using the PREEMPT injection protocol, from a baseline of 20 headache days a month to 12 headache days a month. She received repeated treatments every 12 weeks for more than 3 years. A year ago she had a CGRP monoclonal antibody medication added to her OnabotulinumtoxinA treatment by her neurologist. This has produced an additional 3-4 per day reduction in her headaches, but she now returns with 8-10 headache days a month despite being on both treatments. Her CGRP monoclonal antibody dosing could not be increased by her neurologist nor reimbursed by her insurance carrier. After requests, her provider opts to allow the new Zonal injection protocol to try to increase efficacy and prolong the duration of action. After two treatment cycles she notes a headache day frequency of 1-2 days a month and these attacks respond quickly to her triptan (sumatriptan) medication and reduced the additional need for the CGRP/Mab therapy.

Case Study 13. A 70-year-old female was involved in severe automobile accident 6 years prior. History of prior mild to moderate migraine headaches localized to the temporal areas. Result of injury involved a fractured arm and crushing foot injury requiring 6 surgical repairs, a subtalar fusion of the foot and total knee replacement with lifelong disability associated with CRPS of the affected lower limb. As a result of the injury and hospitalizations, the frequency and severity of the migraine developed into a diagnosis of severe persistent posttraumatic chronic migraine headache with migraine features with episodes increasing in frequency to greater than 15-20 per month. The pain which was present prior to the trauma was concentrated to the temporal areas then developed radiation to the occipital areas and areas of the neck related to post whiplash injury. Posttraumatic symptoms included development of depression, somnolence, lack of responsiveness, with narcotic and antidepressant drug dependence which worsened the symptoms associated with posttraumatic stress disorder (PTSD) secondary to the MV accident. Although, the patient had prior administration of OnabotulinumtoxinA to the temporal and frontal areas of the head with good results prior to the accident, the treatment paradigm and dosage given prior to the accident did not create an adequate reduction in symptoms of migraine creating increased drug over usage and concurrent depression. Evaluation revealed the distribution of the pain to be concentrated over the frontal, temporal and occipital areas within Cluster Zones I, II and III. In addition, there was posttraumatic induced neck pain concentrated over the sternomastoid muscle and back of the neck within the bilateral suboccipital areas. The Zonal treatment protocol was initiated increasing the dosage and varying the concentration over the frontal, temporal and occipital areas including the sternomastoid muscle and splenius capitus, over the course of 1 year, which included 3 treatments, with the first treatment dose being 195 units, the second treatment dose being 245 units, and the last treatment dose also being 245 units. By the 3rd visit, the frequency of the headaches was reduced to a few episodes per month with need for migraine pain medication reduced by greater than 60%. With the reduction of migraine symptoms there was a significantly reduced reliance on pain and tricyclic antidepressant medication with noted improvement in mood, depression, anxiety and symptoms related to symptoms of PTSD.

Case Study 14. A 29-year-old professional football player has a persistent post-traumatic headache disorder with features of migraine. He has had many concussions in the past and has a residual headache disorder but does not want to use any medications that might limit his abilities. He wants to return to active play as soon as possible and asks his provider to give him the most reliable method of doing this without producing side effects. He is treated with the new Zonal injection protocol using an initial dose of 195 units of OnabotulinumtoxinA, to avoid systemic adverse events such as fatigue and/or cognitive effects which usual oral preventives can cause. He returns for follow up and notes that his headaches are much better, and he is subsequently able to play football without noting any negative effects.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A method for treating a migraine disorder, the method comprising extramuscularly administering a Botulinum toxin to an individual in one or more areas of a fronto-fascial layer located in a frontal head region of the individual, the one or more areas of the fronto-fascial layer including a left frontal nerve cluster zone and a right frontal nerve cluster zone, the left frontal nerve cluster zone located in a left portion of the frontal head region directly over and superficial to the left frontalis muscle and the right frontal nerve cluster zone located in a right portion of the frontal head region directly over and superficial to the right frontalis muscle, wherein the left frontal nerve cluster zone is defined by a closed area having a first left frontal horizontal boundary, a second left frontal horizontal boundary, a first left frontal vertical boundary, and a second left frontal vertical boundary, the first left frontal horizontal boundary following a scalp line and being located about 4.5 cm to 7.5 cm above and parallel to a left supraorbital ridge, the second left frontal horizontal boundary being located about 2 cm to about 3 cm below the first left frontal horizontal boundary, the first left frontal vertical boundary being located about 0.5 cm to about 1 cm laterally left from the midline of the forehead, and the second left frontal vertical boundary being located in-line with a medial inferior edge of the left superior orbital ridge, and wherein the right frontal nerve cluster zone is defined by a closed area having a first right frontal horizontal boundary, a second right frontal horizontal boundary, a first right frontal vertical boundary, and a second right frontal vertical boundary, the first right frontal horizontal boundary following a scalp line and being located about 4.5 cm to 7.5 cm above and parallel to a right supraorbital ridge, the second right frontal horizontal boundary being located about 2 cm to about 3 cm below the first right frontal horizontal boundary, the first right frontal vertical boundary being located about 0.5 cm to about 1 cm laterally right from the midline of the forehead, and the second right frontal vertical boundary being located in-line with a medial inferior edge of the right superior orbital ridge, wherein at least 25 units of the Botulinum toxin are administered to the left frontal nerve cluster zone and at least 25 units of the Botulinum toxin are administered to the right frontal nerve cluster zone, one or more areas of a temporoparietal-fascial layer located in a temporal head region of the individual, the one or more areas of the temporoparietal-fascial layer including a left temporal nerve cluster zone and a right temporal nerve cluster zone, the left temporal nerve cluster zone located in a left temporal head region directly over and superficial to the left temporalis muscle and the right temporal nerve cluster zone located in a right temporal head region directly over and superficial to the right temporalis muscle, wherein the left temporal nerve cluster zone is defined by a closed area having a first left temporal horizontal boundary, a second left temporal horizontal boundary, a first left temporal vertical boundary, and a second left temporal vertical boundary, the first left temporal horizontal boundary being in-line with and following a curvature of a left superior temporal line, the second left temporal horizontal boundary being located about 1.5 cm to about 2 cm above and following a superior aspect of a left zygomatic arch and a curvature of an outside edge of a left crus and a superior portion of a left helical rim of a left ear, the first left temporal vertical boundary being positioned in line with an outer dorsal edge of the left helical rim of the left ear, and the second left temporal vertical boundary being positioned in line with a ventral edge of a head of a left condylar process of a left mandibular ramus, and wherein the right temporal nerve cluster zone is defined by a closed area having a first right temporal horizontal boundary, a second right temporal horizontal boundary, a first right temporal vertical boundary, and a second right temporal vertical boundary, the first right temporal horizontal boundary being in-line with and following a curvature of a right superior temporal line, the second right temporal horizontal boundary being located about 1.5 cm to about 2 cm above and following a superior aspect of a right zygomatic arch and a curvature of an outside edge of a right crus and a superior portion of a right helical rim of a right ear, the first right temporal vertical boundary being positioned in line with an outer dorsal edge of the right helical rim of the right ear, and the second right temporal vertical boundary being positioned in line with a ventral edge of a head of a right condylar process of a right mandibular ramus, and one or more areas of an occipito-fascial layer located in an occipital head region of the individual, the one or more areas of the occipito-fascial layer including a left occipital nerve cluster zone and a right occipital nerve cluster zone, the left occipital nerve cluster zone located in a left portion of the occipital head region directly over and superficial to the left occipitalis muscle and the right occipital nerve cluster zone located in a right portion of the occipital head region directly over and superficial to the right occipitalis muscle, wherein the left occipital nerve cluster zone is defined by a closed area having a first left occipital horizontal boundary, a second left occipital horizontal boundary, a first left occipital vertical boundary, and a second left occipital vertical boundary, the first left occipital horizontal boundary being located about 3 cm above and following a left superior aspect of a nuchal ridge, the second left occipital horizontal boundary being located in-line with the left superior aspect of the nuchal ridge, the first left occipital vertical boundary being located about 0.5 cm to about 1 cm laterally left from an external occipital crest and the second left occipital vertical boundary being positioned in line with a left mastoid process and a dorsal portion of a left superior temporal line, and wherein the right occipital nerve cluster zone is defined by a closed area having a first right occipital horizontal boundary, a second right occipital horizontal boundary, a first right occipital vertical boundary, and a second right occipital vertical boundary, the first right occipital horizontal boundary being located about 3 cm above and following a right superior aspect of the nuchal ridge, the second right occipital horizontal boundary being located in-line with the right superior aspect of the nuchal ridge, the first right occipital vertical boundary being located about 0.5 cm to about 1 cm laterally right from the external occipital crest and the second right occipital vertical boundary being positioned in line with a right mastoid process and a dorsal portion of a right superior temporal line, wherein at least 30 units of the Botulinum toxin are administered to the left occipital nerve cluster zone and at least 30 units of the Botulinum toxin are administered to the right occipital nerve cluster zone, wherein a unit of the Botulinum toxin is defined as the potency or activity ascribed to a unit of onabotulinumtoxinA, and wherein a unit of incobotulinumtoxinA and a unit of prabotulinumtoxinA is equivalent to the unit of onabotulinumtoxinA, and wherein a unit of abobotulinumtoxinA is about 2.5 to about 3 times more than the unit of onabotulinumtoxinA.

2. The method of claim 1, wherein the Botulinum toxin is administered to each of the one or more areas of the fronto-fascial layer, each of the one of more areas of a temporoparietal-fascial layer, and each of the one or more areas of the occipito-fascial layer in a concentration of 5 units/100 μL.

3. The method of claim 1, wherein the Botulinum toxin is administered to each of the one or more areas of the fronto-fascial layer, each of the one of more areas of a temporoparietal-fascial layer, and each of the one or more areas of the occipito-fascial layer in a concentration of 5 units/200 μL.

4. The method of claim 1, wherein 40 units to 60 units of the Botulinum toxin are administered within the fronto-fascial layer, wherein 5 units of the Botulinum toxin is administered to each of the one or more sites within the one or more areas of the fronto-fascial layer.

5. The method of claim 1, wherein 40 units to 70 units of the Botulinum toxin are administered within the temporoparietal-fascial layer, wherein 5 units of the Botulinum toxin is administered to each of one or more sites within the one or more areas of the temporoparietal-fascial layer.

6. The method of claim 1, wherein 60 units to 110 units of the Botulinum toxin are administered within the occipito-fascial layer, wherein 5 units of the Botulinum toxin is administered to each of one or more sites within the one or more areas of the occipito-fascial layer.

7. The method of claim 1, wherein 25 units to 30 units of the Botulinum toxin are administered to the left frontal nerve cluster zone and 25 units to 30 units of the Botulinum toxin are administered to the right frontal nerve cluster zone, wherein 5 units of the Botulinum toxin is administered to each of one or more sites within the left frontal nerve cluster zone and the right frontal nerve cluster zone.

8. The method of claim 1, wherein 20 units to 35 units of the Botulinum toxin are administered to the left temporal nerve cluster zone and 20 units to 35 units of the Botulinum toxin are administered to the right temporal nerve cluster zone, wherein 5 units of the Botulinum toxin is administered to each of the one or more sites within the left temporal nerve cluster zone and the right temporal nerve cluster zone.

9. The method of claim 1, wherein 30 units to 55 units of the Botulinum toxin are administered to the left occipital nerve cluster zone and 30 units to 55 units of the Botulinum toxin are administered to the right occipital nerve cluster zone, wherein 5 units of the Botulinum toxin is administered to each of one or more sites within the left occipital nerve cluster zone and the right occipital nerve cluster zone.

10. The method of claim 1, further comprising extramuscularly administering a Botulinum toxin to one or more nerve exit points in the head and neck.

11. The method of claim 10, wherein the Botulinum toxin is extramuscularly administered to one or more nerve exit points of a Supraorbital nerve, a Supratrochlear nerve, or any combination thereof.

12. The method of claim 11, wherein the one or more nerve exit points of the Supraorbital nerve include the left and right Supraorbital foramen.

13. The method of claim 11, wherein the one or more nerve exit points of the Supratrochlear nerve include the left and right Supratrochlear foramen.

14. The method of claim 10, wherein the Botulinum toxin is extramuscularly administered to a location along a medial branch of a Supratrochlear nerve located subcutaneously above the central part of the procerus muscle.

15. The method of claim 10, wherein the Botulinum toxin is extramuscularly administered to an exit location of the Greater Auricular nerve located subcutaneously above the posterior edge of the midpoint of the left Sternocleidomastoideole and to an exit location of the Greater Auricular nerve located subcutaneously above the posterior edge of the midpoint of the left Sternocleidomastoideole.

16. The method of claim 15, further comprising extramuscularly administered of the Botulinum toxin to a location along the Greater Auricular nerve located subcutaneously above a position midway between the mastoid process and a line drawn at the midpoint of the left Sternocleidomastoideole and to a location along the Greater Auricular nerve located subcutaneously above a position midway between the mastoid process and a line drawn at the midpoint of the right Sternocleidomastoideole.

17. The method of claim 10, wherein each of the one or more nerve exit points is administered 5 units of the Botulinum toxin.

18. The method of claim 10, wherein the Botulinum toxin is administered to each of the one or more nerve exit points in the head and neck in a concentration of 5 units/100 µL.

19. The method of claim 10, wherein the Botulinum toxin is administered to each of the one or more nerve exit points in the head and neck in a concentration of 5 units/200 µL.

20. The method of claim 1, further comprising extramuscularly administering a Botulinum toxin to one or more sites along a Supraclavicular nerve, a Cervical Nerve Plexus, or any combination thereof.

21. The method of claim 20, wherein the one or more sites along the Supraclavicular nerve include one or more subcutaneous sites located at an apical ridge of a superior portion of a left Trapezius muscle or one or more subcutaneous sites located at an apical ridge of a superior portion of a right Trapezius muscle.

22. The method of claim 20, wherein the one or more sites along the Cervical Nerve Plexus include a subcutaneous site located above a cervical vertebrae insertion of a left Longissimus capitis muscle, a subcutaneous site located above a cervical vertebrae insertion of a left Longissimus cervicis muscle, a subcutaneous site located above a cervical vertebrae insertion of a right Longissimus capitis muscle, or a subcutaneous site located above a cervical vertebrae insertion of a right Longissimus cervicis muscle.

23. The method of claim 20, wherein each of the one or more sites along the Supraclavicular nerve and the Cervical Nerve Plexus is administered 5 units of the Botulinum toxin.

24. The method of claim 20, wherein the Botulinum toxin is administered in a concentration of 5 units/100 µL to each of the one or more sites along a Supraclavicular nerve, a Cervical Nerve Plexus, or any combination thereof.

25. The method of claim 20, wherein the Botulinum toxin is administered in a concentration of 5 units/200 µL to each of the one or more sites along a Supraclavicular nerve, a Cervical Nerve Plexus, or any combination thereof.

26. The method of claim 1, further comprising one or more additional administration sites peripheral to the left and right frontal nerve cluster zones (LZI and RZI), the left and right temporal nerve cluster zones (LZII and RZII), and/or the left and right occipital nerve cluster zones (LZIII and RZIII).

27. The method of claim 1, further comprising extramuscularly administering a Botulinum toxin to one or more sites of an epicranial aponeurosis.

28. The method of claim 27, wherein each of the one or more sites is administered 5 units of the Botulinum toxin.

29. The method of claim 27, wherein the Botulinum toxin is administered to each of the one or more sites of an epicranial aponeurosis in a concentration of 5 units/100 µL.

30. The method of claim 27, wherein the Botulinum toxin is administered to each of the one or more sites of an epicranial aponeurosis in a concentration of 5 units/200 µL.

31. The method of claim 1, further comprising intramuscularly administering a Botulinum toxin to one or more locations within the left and right Splenius Capitis muscle, the left and right Masseter muscles, the left and right Trapezius muscles, or any combination thereof.

32. The method of claim 31, wherein the one or more locations of the left and right Splenius Capitis muscles include an intramuscular site located above a soft triangular depression cranially to a superior edge of a left Splenius Capitis muscle or an intramuscular site located above a soft triangular depression cranially to a superior edge of a right Splenius Capitis muscle.

33. The method of claim 31, wherein the one or more locations of the left and right Masseter muscles include one or more intramuscular sites located above a left masseter muscle near an angle of a left mandibular ramus or one or more intramuscular sites located above a right masseter muscle near an angle of a right mandibular ramus.

34. The method of claim 31, wherein the one or more locations of the left and right Trapezius muscles include one or more intramuscular sites located at an apical ridge of a superior portion of a left Trapezius muscle or one or more intramuscular sites located at an apical ridge of a superior portion of a right Trapezius muscle.

35. The method of claim 1, wherein the individual was nonresponsive to another Botulinum toxin treatment.

* * * * *